United States Patent
Nagamine et al.

(10) Patent No.: US 9,671,690 B2
(45) Date of Patent: Jun. 6, 2017

(54) RESIST COMPOSITION, METHOD FOR FORMING RESIST PATTERN, PHOTO-REACTIVE QUENCHER AND COMPOUND

(71) Applicant: TOKYO OHKA KOGYO CO., LTD., Kawasaki-shi (JP)

(72) Inventors: Takashi Nagamine, Kawasaki (JP); Daichi Takaki, Kawasaki (JP); Miki Shinomiya, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/072,036

(22) Filed: Mar. 16, 2016

(65) Prior Publication Data
US 2016/0282717 A1     Sep. 29, 2016

(30) Foreign Application Priority Data
Mar. 24, 2015 (JP) ................ 2015-061286

(51) Int. Cl.
| | | |
|---|---|---|
| G03F 7/004 | (2006.01) |
| G03F 7/039 | (2006.01) |
| G03F 7/20 | (2006.01) |
| G03F 7/30 | (2006.01) |
| G03F 7/32 | (2006.01) |
| C07C 309/04 | (2006.01) |
| C07C 309/19 | (2006.01) |
| C07C 309/25 | (2006.01) |
| C07C 309/29 | (2006.01) |
| C07C 309/30 | (2006.01) |
| C07C 381/12 | (2006.01) |
| C07C 311/04 | (2006.01) |
| C07C 309/07 | (2006.01) |
| C07C 309/06 | (2006.01) |
| C07C 65/05 | (2006.01) |
| C07C 53/21 | (2006.01) |
| C07D 307/00 | (2006.01) |

(52) U.S. Cl.
CPC ............ *G03F 7/0045* (2013.01); *C07C 53/21* (2013.01); *C07C 65/05* (2013.01); *C07C 309/04* (2013.01); *C07C 309/06* (2013.01); *C07C 309/07* (2013.01); *C07C 309/19* (2013.01); *C07C 309/25* (2013.01); *C07C 309/29* (2013.01); *C07C 309/30* (2013.01); *C07C 311/04* (2013.01); *C07C 381/12* (2013.01); *C07D 307/00* (2013.01); *G03F 7/0046* (2013.01); *G03F 7/0397* (2013.01); *G03F 7/2041* (2013.01); *G03F 7/30* (2013.01); *G03F 7/322* (2013.01); *C07C 2102/42* (2013.01); *C07C 2103/74* (2013.01)

(58) Field of Classification Search
None
See application file for complete search history.

(56) References Cited

U.S. PATENT DOCUMENTS

| | | | | |
|---|---|---|---|---|
| 2004/0229162 A1* | 11/2004 | Ohsawa | ................ | C07C 381/12 430/270.1 |
| 2007/0105045 A1* | 5/2007 | Iwato | .................... | G03F 7/0392 430/270.1 |
| 2014/0163254 A1* | 6/2014 | Kinoshita | ............. | C07C 309/19 562/41 |

FOREIGN PATENT DOCUMENTS

JP        2014-115386 A      6/2014

* cited by examiner

*Primary Examiner* — Sin Lee
(74) *Attorney, Agent, or Firm* — Knobbe Martens Olson & Bear LLP

(57) ABSTRACT

A resist composition which generates an acid upon exposure and whose solubility in a developing solution changes under the action of an acid. The composition includes a base material component whose solubility in a developing solution changes under the action of an acid; an acid generator component which generates an acid upon exposure; and a photo-reactive quencher which contains a compound represented by the general formula shown below:

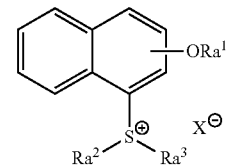

in which $Ra^1$ represents an alkyl group having 1 to 10 carbon atoms which may have a substituent; and $Ra^2$ and $Ra^3$ each independently represent an alkyl group having 1 to 10 carbon atoms which may have a substituent. $X^-$ represents a counter anion.

4 Claims, No Drawings

RESIST COMPOSITION, METHOD FOR FORMING RESIST PATTERN, PHOTO-REACTIVE QUENCHER AND COMPOUND

CROSS-REFERENCE TO RELATED APPLICATIONS

Priority is claimed on Japanese Patent Application No. 2015-061286, filed Mar. 24, 2015, the content of which is incorporated herein by reference.

BACKGROUND OF THE INVENTION

Field of the Invention

The present invention relates to a resist composition, a method for forming a resist pattern, a photo-reactive quencher, and a compound.

Background Art

In lithography techniques, for example, a resist film composed of a resist material is formed on a substrate, and the resist film is subjected to selective exposure of radiation such as light or electron beams through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (increasing the energy) of an exposure light source. Specifically, conventionally, ultraviolet radiation typified by g-line and i-line radiation has been used, but nowadays KrF excimer lasers and ArF excimer lasers are starting to be introduced in mass production of a semiconductor element. Furthermore, research is also being conducted into lithography techniques that use an exposure light source having a wavelength shorter (energy higher) than these excimer lasers, such as electron beams, extreme ultraviolet radiation (EUV), and X ray.

A typical resist composition includes an acid generator, and solubility of the composition in a developing solution changes under the action of an acid generated from the acid generator. The behavior of the acid generated from the acid generator has great influence on lithography properties. Therefore, a quencher component is used for the purpose of controlling a diffusion length of the acid. For example, Japanese Unexamined Patent Application, Publication No. 2014-115386 discloses a resist composition using a photo-reactive type quencher.

SUMMARY OF THE INVENTION

However, with respect to the invention disclosed in Japanese Unexamined Patent Application, Publication No. 2014-115386, there is still room for further improvements of the lithography properties.

The present invention has been made taking this problem into consideration and an object thereof is to provide a resist composition having excellent lithography properties and a method for forming a resist pattern using the resist composition.

According to a first aspect of the present invention, there is provided a resist composition which generates an acid upon exposure and whose solubility in a developing solution changes under the action of an acid, the composition including: a base material component (A) whose solubility in a developing solution changes under the action of an acid; an acid generator component (B) which generates an acid upon exposure; and a photo-reactive quencher (D0) which contains a compound (D0-1) represented by General formula (d0) shown below.

[Chemical formula 1]

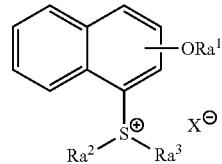

(d0)

In the formula, $Ra^1$ represents an alkyl group having 1 to 10 carbon atoms which may have a substituent; and $Ra^2$ and $Ra^3$ each independently represent an alkyl group having 1 to 10 carbon atoms which may have a substituent. $X^-$ represents a counter anion.

According to a second aspect of the invention, there is provided a method for forming a resist pattern including: forming a resist film using the resist composition according to the first aspect on a support; exposing the resist film to light; and developing the resist film to form a resist pattern.

According to a third aspect of the invention, there is provided a photo-reactive quencher including: a compound (D0-1) represented by general formula (d0) shown below.

[Chemical formula 2]

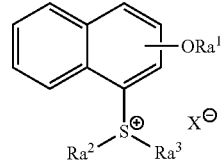

(d0)

In the formula, $Ra^1$ represents an alkyl group having 1 to 10 carbon atoms which may have a substituent; and $Ra^2$ and $Ra^3$ each independently represent an alkyl group having 1 to 10 carbon atoms which may have a substituent. $X^-$ represents a counter anion represented by any one of formulae (d1-1) to (d1-3) shown below.

[Chemical formula 3]

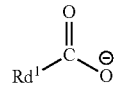

(d1-1)

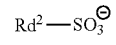

(d1-2)

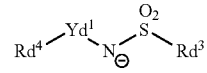

(d1-3)

In formulae (d1-1) to (d1-3), $Rd^1$ to $Rd^4$ represent a cyclic group which may have a substituent, a chain-like alkyl group which may have a substituent, or a chain-like alkenyl group which may have a substituent. However, two or more of fluorine atoms are not bonded to a carbon atom adjacent to an S atom in $Rd^2$ in formula (d1-2). $Yd^1$ represents a single bond or a divalent linking group.

According to a fourth aspect of the present invention, there is provided a compound represented by general formula (d0) shown below.

[Chemical formula 4]

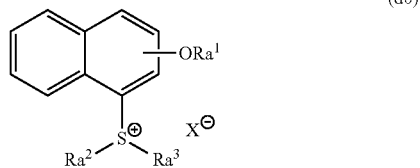

(d0)

In the formula, $Ra^1$ represents an alkyl group having 1 to 10 carbon atoms which may have a substituent; and $Ra^2$ and $Ra^3$ each independently represent an alkyl group having 1 to 10 carbon atoms which may have a substituent. $X^-$ represents a counter anion represented by any one of formulae (d1-1) to (d1-3) shown below.

[Chemical formula 5]

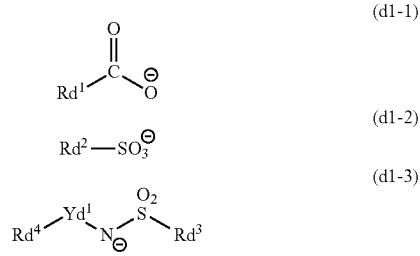

(d1-1)

(d1-2)

(d1-3)

In formulae (d1-1) to (d1-3), $Rd^1$ to $Rd^4$ represent a cyclic group which may have a substituent, a chain-like alkyl group which may have a substituent, or a chain-like alkenyl group which may have a substituent. However, two or more of fluorine atoms are not bonded to a carbon atom adjacent to an S atom in $Rd^2$ in formula (d1-2). $Yd^1$ represents a single bond or a divalent linking group.

According to the present invention, it is possible to provide a resist composition having excellent lithography properties and a method for forming a resist pattern using the resist composition.

DETAILED DESCRIPTION OF THE INVENTION

In the present description and claims, the term "aliphatic" is a relative concept used in relation to the term "aromatic", and defines a group or a compound that has no aromaticity.

The term "alkyl group" includes a linear, branched or cyclic, monovalent saturated hydrocarbon, unless otherwise specified. The same applies for the alkyl group within an alkoxy group.

The term "alkylene group" includes a linear, branched or cyclic, divalent saturated hydrocarbon group, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group is substituted with a fluorine atom.

The term "structural unit" refers to a monomer unit that contributes to the formation of a polymeric compound (resin, polymer, copolymer).

A "structural unit derived from an acrylic ester" refers to a structural unit that is formed by the cleavage of the ethylenic double bond of an acrylic ester.

An "acrylic ester" refers to a compound in which the terminal hydrogen atom of the carboxy group of acrylic acid ($CH_2$=CH—COOH) is substituted with an organic group.

With respect to the acrylic ester, the hydrogen atom bonded to the carbon atom present on the α-position may be substituted with a substituent. The substituent ($R^\alpha$) that may substitute the hydrogen atom bonded to the carbon atom present on the α-position is an atom other than a hydrogen atom or a group, and examples thereof include an alkyl group having 1 to 5 carbon atoms, a halogenated alkyl group having 1 to 5 carbon atoms and a hydroxyalkyl group. A carbon atom present on the α-position in an acrylic ester refers to the carbon atom bonded to the carbonyl group, unless specified otherwise.

Hereafter, an acrylic ester having a substituent which substitutes the hydrogen atom bonded to the carbon atom present on the α-position is sometimes referred to as "α-substituted acrylic ester". Further, acrylic esters and α-substituted acrylic esters are collectively referred to as "(α-substituted) acrylic ester".

A "structural unit derived from hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom bonded to the carbon atom present on the α-position of hydroxystyrene is substituted with a substituent such as an alkyl group or a halogenated alkyl group; and derivatives thereof. Examples of the derivatives thereof include a hydroxystyrene derivative in which the hydrogen atom of the hydroxy group is substituted with an organic group; and a hydroxystyrene derivative which has a substituent other than a hydroxy group besides a hydroxy group on the benzene ring, each with respect to a hydroxystyrene which may have a substituent which substitutes the hydrogen atom bonded to the carbon atom present on the α-position. Here, the α-position carbon atom (carbon atom on the α-position) refers to the carbon atom which is bonded to the benzene ring of the hydroxystyrene, unless specified otherwise.

As the substituent which substitutes the hydrogen atom on the α-position carbon atom of the hydroxystyrene, the same substituents as those described above for the substituent on the α-position carbon atom of the aforementioned α-substituted acrylic ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes a compound in which the hydrogen atom on the α-position carbon atom of vinylbenzoic acid is substituted with a substituent such as an alkyl group or a halogenated alkyl group; and derivatives thereof. Examples of the derivatives thereof include a benzoic acid derivative in which the hydrogen atom of the carboxy group is substituted with an organic group; and a benzoic acid derivative which has a substituent (other than a hydroxy group and a carboxy group) which is bonded to the benzene ring, each with respect to vinylbenzoic acid which may have a substituent which substitutes the hydrogen atom on the α-position carbon atom. Here, the α-position carbon atom (carbon atom on the α-position) refers to the carbon atom bonded to the benzene ring in the vinyl group of vinylbenzoic acid, unless specified otherwise.

A "styrene derivative" refers to a compound in which the hydrogen atom on the α-position carbon atom of styrene is substituted with a substituent such as an alkyl group, a halogenated alkyl group or the like.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position carbon, a linear or branched alkyl group is preferable, and specific examples include an alkyl group having 1 to 5 carbon atoms such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position carbon atom include a group in which part or all of the hydrogen atoms of the aforementioned "alkyl group as the substituent on the α-position carbon atom" are substituted with a halogen atom. Examples of the halogen atom include a fluorine atom, a chlorine atom, a bromine atom and an iodine atom, and a fluorine atom is particularly desirable.

Specific examples of the hydroxyalkyl group as the substituent on the α-position carbon atom include groups in which part or all of the hydrogen atoms of the aforementioned "alkyl group as the substituent on the α-position carbon atom" are substituted with a hydroxy group. The number of hydroxy groups within the hydroxyalkyl group is preferably 1 to 5, and most preferably 1.

A case with the description "may have a substituent" includes both of the case where the hydrogen atom (—H) is substituted with a monovalent group and the case where the methylene group (—CH$_2$—) is substituted with a divalent group.

The term "exposure" is used as a general concept that includes irradiation with any form of radiation.

Resist Composition

A first aspect of the present invention is a resist composition which generates an acid upon exposure and whose solubility in a developing solution changes under the action of an acid, the composition including: a base material component (A) whose solubility in a developing solution changes under the action of an acid; an acid generator component (B) which generates an acid upon exposure; and a photo-reactive quencher (D0) which contains a compound (D0-1) represented by general formula (d0) shown below.

In the present invention, the resist composition contains a base material component (A) whose solubility in a developing solution changes under the action of an acid (hereinafter, referred to as "component (A)").

If a resist film is formed using the resist composition and the resist film is selectively exposed, an acid is generated in the exposed portion, and solubility of the component (A) in a developing solution changes under the action of an acid, whereas solubility of the component (A) in a developing solution does not change in the unexposed portion. Thus, a difference in solubility in a developing solution is generated between the exposed portion and the unexposed portion. Therefore, if the resist film is developed, in the case of a positive-type resist composition, the exposed portion is dissolved and removed, thereby forming a positive-type resist pattern, and in the case of a negative-type resist composition, the unexposed portion is dissolved and removed, thereby forming a negative-type resist pattern.

In the present specification, the resist composition in which the exposed portion is dissolved and removed to form a positive-type resist pattern is referred to as a positive-type resist composition, and the resist composition in which the unexposed portion is dissolved and removed to form a negative-type resist pattern is referred to as a negative-type resist composition.

In the present invention, the resist composition may be the positive-type resist composition or the negative-type resist composition.

In addition, in the present invention, the resist composition may be used for an alkali developing process in which an alkali developing solution is used for a developing process when forming a resist pattern, and may be used for a solvent developing process in which a developing solution (organic developing solution) including an organic solvent is used for the developing process, and the resist composition is preferably used for the solvent developing process.

The resist composition for forming the resist pattern has an acid generating ability which generates an acid upon exposure, and the component (A) may generate an acid upon exposure or an additive component separately mixed with the component (A) may generate an acid upon exposure.

Specifically, in the present invention, (1) The resist composition may contain an acid generator component (B) (hereinafter, referred to as "component (B)") which generates an acid upon exposure;

(2) The component (A) may be a component which generates an acid upon exposure;

(3) The component (A) is a component which generates an acid upon exposure, and further the component (B) may be contained.

In other words, in cases of the aforementioned (2) and (3), the component (A) is a "base material component which generates an acid upon exposure and whose solubility in a developing solution changes under the action of an acid". In the case where the component (A) is the base material component which generates an acid upon exposure and whose solubility in a developing solution changes under the action of an acid, a component (A1) described below is preferably a polymer compound which generates an acid upon exposure and whose solubility in a developing solution changes under the action of an acid. As the polymer compound, a resin having a structural unit which generates an acid upon exposure can be used. As the structural unit which generates an acid upon exposure, the conventional structural units can be used.

In the present invention, as the resist composition, the aforementioned case (1) is particularly preferable.

Component (A)

In the present invention, the "base material component" is an organic compound having a film forming ability, and an organic compound having a molecular weight of 500 or more is preferably used. If the molecular weight of the organic compound is 500 or more, the film forming ability is enhanced and additionally a nano-level photosensitive resin pattern is easily formed.

The organic compound used as the base material component is largely classified into a non-polymer and a polymer.

The non-polymer whose molecular weight is 500 to less than 4,000 is commonly used. Hereinafter, a "low molecular weight compound" indicates a non-polymer whose molecular weight is 500 to less than 4,000.

The polymer whose molecular weight is 1,000 or more is commonly used. Hereinafter, a "resin" indicates a polymer whose molecular weight is 1,000 or more.

As the molecular weight of the polymer, a weight average molecular weight in terms of polystyrene determined by gel permeation chromatography (GPC) can be used.

For the component (A), the resin may be used, the low molecular weight compound may be used, or a combination thereof may be used.

The component (A) is a compound whose solubility in a developing solution increases under the action of an acid.

In addition, in the present invention, the component (A) may generate an acid upon exposure.

In the present invention, the component (A) preferably includes a polymer compound (A1) containing a structural unit having an acid decomposable group that exhibits increased polarity by the action of an acid (hereinafter, may be referred to as "structural unit (a1)"), a structural unit having a —SO$_2$-containing cyclic group, a lactone-containing cyclic group, a carbonate-containing cyclic group or a heterocyclic group other than these (hereinafter, may be referred to as "structural unit (a2)"), and a structural unit having a polar group-containing aliphatic hydrocarbon group (hereinafter, may be referred to as "structural unit (a3)").

Structural Unit (a1)

The structural unit (a1) is a structural unit containing an acid decomposable group that exhibits increased polarity by the action of an acid.

The term "acid decomposable group" refers to a group having acid decomposability, in which at least a part of the bond within the structure of the acid decomposable group is cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group (—SO$_3$H). Among these, a sulfo group or a polar group containing —OH in the structure thereof (hereinafter, referred to as "OH-containing polar group") is preferable, a sulfo group or a carboxy group or a hydroxy group is more preferable, and a carboxy group or a hydroxyl group is particularly preferable.

More specifically, as an acid decomposable group, a group in which the aforementioned polar group is protected with an acid dissociable group (such as a group in which the hydrogen atom of the OH-containing polar group is protected with an acid dissociable group), can be exemplified.

The "acid dissociable group" refers to both (i) a group having acid decomposability, in which the bond between the acid dissociable group and the adjacent atom is cleaved by the action of an acid; and (ii) a group in which one of the bonds is cleaved by the action of an acid, and then a decarboxylation reaction occurs, thereby cleaving the bond between the acid dissociable group and the adjacent atom.

It is necessary that the acid dissociable group that constitutes the acid decomposable group is a group which exhibits a lower polarity than the polar group generated by the dissociation of the acid dissociable group. Thus, when the acid dissociable group is dissociated by the action of an acid, a polar group exhibiting a higher polarity than that of the acid dissociable group is generated, thereby increasing the polarity. As a result, the polarity of the entire component (A1) is increased. By the increase in the polarity, the solubility in a developing solution relatively changes and, the solubility in an organic developing solution is relatively decreased.

The acid dissociable group is not particularly limited, and any of the groups that have been conventionally proposed as acid dissociable groups for the base resins of chemically amplified resists can be used.

Examples of the acid dissociable group for protecting the carboxy group or hydroxy group among the aforementioned polar group include the acid dissociable group represented by general formula (a1-r-1) shown below (hereinafter, for the sake of convenience, sometimes referred to as "acetal-type acid dissociable group").

[Chemical formula 6]

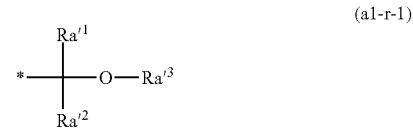

(a1-r-1)

In the formula, Ra'$^1$ and Ra'$^2$ represent a hydrogen atom or an alkyl group; Ra'$^3$ represents a hydrocarbon group; and Ra'$^3$ may be bonded to Ra'$^1$ or Ra'$^2$ to form a ring. * means a valence bond.

In formula (a1-r-1), as the alkyl group for Ra'$^1$ and Ra'$^2$, the same alkyl groups as those described above as the substituent which may be bonded to the carbon atom on the α-position of the aforementioned α-substituted acrylic ester can be used, although a methyl group or ethyl group is preferable, and a methyl group is most preferable.

The hydrocarbon group for Ra'$^3$ is preferably an alkyl group having 1 to 20 carbon atoms, more preferably an alkyl group having 1 to 10 carbon atoms, and still more preferably a linear or branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, a 1,1-dimethylethyl group, a 1,1-diethylpropyl group, a 2,2-dimethylpropyl group and a 2,2-dimethylbutyl group.

In the case where Ra'$^3$ represents a cyclic hydrocarbon group, the cyclic hydrocarbon group may be aliphatic or aromatic, and may be polycyclic or monocyclic. As the monocyclic aliphatic hydrocarbon group, a group in which one hydrogen atom is removed from monocycloalkane is preferable. The monocycloalkane preferably has 3 to 8 carbon atoms, and specific examples thereof include cyclopentane, cyclohexane and cyclooctane. As the polycyclic aliphatic hydrocarbon group, a group in which one hydrogen atom is removed from polycycloalkane is preferable, and the polycycloalkane preferably has 7 to 12 carbon atoms. Examples of the polycycloalkane include adamantane, norbornane, isobornane, tricyclodecane and tetracyclododecane.

In the case where the hydrocarbon group is an aromatic hydrocarbon group, examples of the aromatic ring contained in the aromatic hydrocarbon group include aromatic hydrocarbon rings, such as benzene, biphenyl, fluorene, naphthalene, anthracene and phenanthrene; and aromatic hetero rings in which a part of the carbon atoms constituting the aforementioned aromatic hydrocarbon rings is substituted with a hetero atom. Examples of the hetero atom within the aromatic hetero rings include an oxygen atom, a sulfur atom and a nitrogen atom.

Specific examples of the aromatic hydrocarbon group include a group in which one hydrogen atom is removed from the aforementioned aromatic hydrocarbon ring (aryl group); and a group in which one hydrogen atom of the aforementioned aryl group is substituted with an alkylene group (an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atoms, more preferably 1 or 2, and particularly preferably 1.

In the case where $Ra'^3$ is bonded to $Ra'^1$ or $Ra'^2$ to form a ring, the cyclic group is preferably a 4- to 7-membered ring, and more preferably a 4- to 6-membered ring. Specific examples of the cyclic group include a tetrahydropyranyl group and a tetrahydrofuranyl group.

Examples of the acid dissociable group for protecting the carboxy group among the aforementioned polar group include the acid dissociable group represented by general formula (a1-r-2) shown below (hereinafter, among the acid dissociable group represented by the following formula (a1-r-2), the acid dissociable group constituted of alkyl groups is referred to as "tertiary alkylester-type acid dissociable group").

[Chemical formula 7]

(a1-r-2)

In the formula, $Ra'^4$ to $Ra'^6$ each independently represent a hydrocarbon group; and $Ra'^5$ and $Ra'^6$ may be mutually bonded to form a ring. * means a valence bond.

As the hydrocarbon group for $Ra'^4$ to $Ra'^6$, the same groups as those described above for $Ra'^3$ can be exemplified. $Ra'^4$ is preferably an alkyl group having 1 to 5 carbon atoms. In the case where $Ra'^5$ and $Ra'^6$ are mutually bonded to form a ring, a group represented by general formula (a1-r2-1) shown below can be exemplified.

On the other hand, in the case where $Ra'^4$ to $Ra'^6$ are not mutually bonded and independently represent a hydrocarbon group, the group represented by general formula (a1-r2-2) shown below can be exemplified.

[Chemical formula 8]

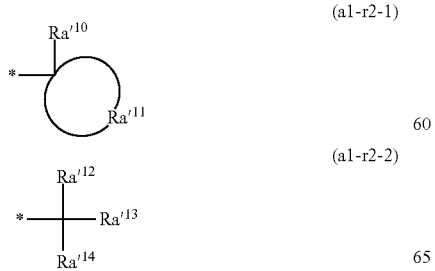

(a1-r2-1)

(a1-r2-2)

In the formulae, $Ra'^{10}$ represents an alkyl group having 1 to 10 carbon atoms; $Ra'^{11}$ is a group which forms an aliphatic cyclic group together with a carbon atom having $Ra'^{10}$ bonded thereto; and $Ra'^{12}$ to $Ra'^{14}$ each independently represent a hydrocarbon group. * means a valence bond.

In formula (a1-r2-1), as the alkyl group having 1 to 10 carbon atoms for $Ra'^{10}$, the same groups as described above for the linear or branched alkyl group for $Ra'^3$ in formula (a1-r-1) are preferable. In formula (a1-r2-1), as the aliphatic cyclic group which is formed by $Ra'^{11}$, the same groups as those described above for the cyclic alkyl group for $Ra'^3$ in formula (a1-r-1) are preferable.

In formula (a1-r2-2), it is preferable that $Ra'^{12}$ and $Ra'^{14}$ each independently represent an alkyl group having 1 to 10 carbon atoms, and it is more preferable that the alkyl group is the same group as the described above for the linear or branched alkyl group for $Ra'^3$ in formula (a1-r-1), it is still more preferable that the alkyl group is a linear alkyl group having 1 to 5 carbon atoms, and it is particularly preferable that the alkyl group is a methyl group or an ethyl group.

In formula (a1-r2-2), it is preferable that $Ra'^{13}$ is the linear, branched or cyclic alkyl group exemplified as the hydrocarbon group for $Ra'^3$ in formula (a1-r-1). Among these, the same cyclic alkyl group as those described above for $Ra'^3$ is more preferable.

Specific examples of formula (a1-r2-1) are shown below. In the formulae shown below, "*" represents a valence bond.

[Chemical formula 9]

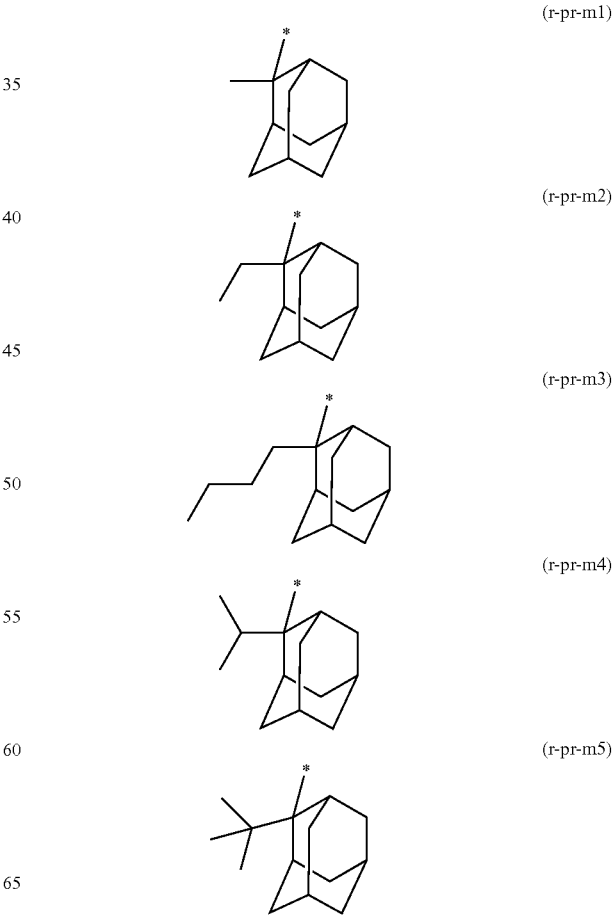

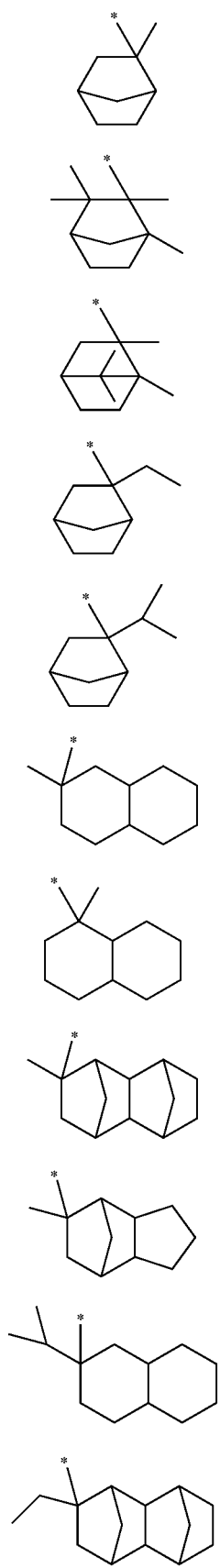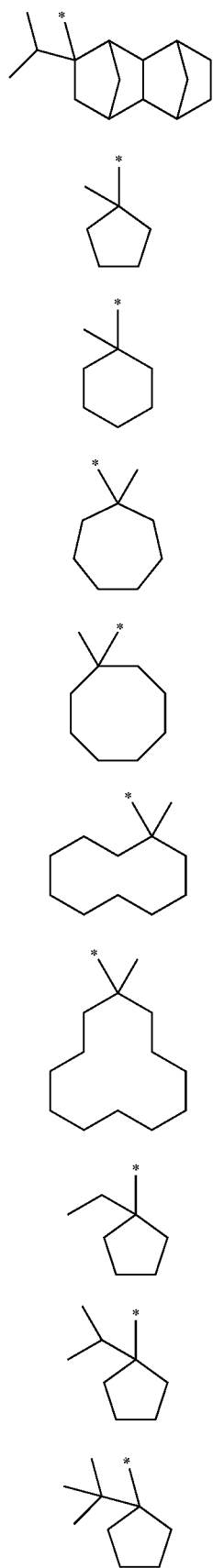

(r-pr-s10)
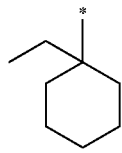
(r-pr-s11)
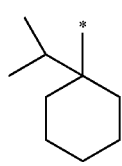
(r-pr-s12)
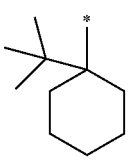
(r-pr-s13)
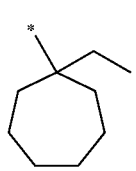
(r-pr-s14)
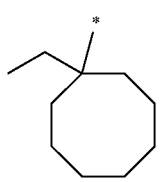
(r-pr-s15)
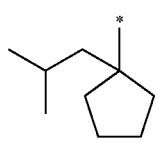
(r-pr-s16)
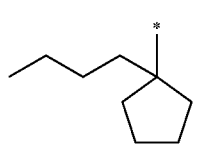
(r-pr-s17)
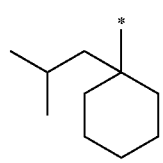
(r-pr-s18)
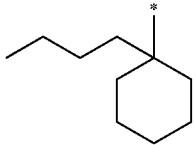
Specific examples of formula (a1-r2-2) are shown below.
[Chemical formula 10]
(r-pr-cm1)
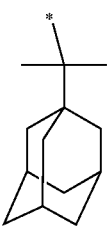
(r-pr-cm2)
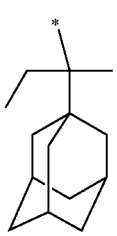
(r-pr-cm3)
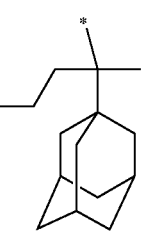
(r-pr-cm4)
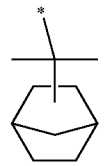
(r-pr-cm5)
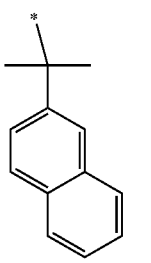

(r-pr-cm6) 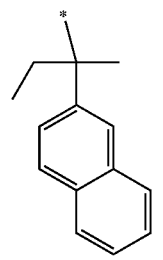

(r-pr-cm7) 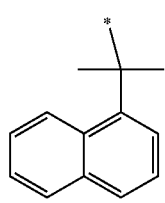

(r-pr-cm8) 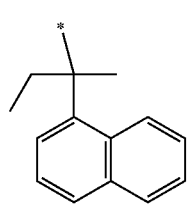

(r-pr-cs1) 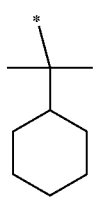

(r-pr-cs2) 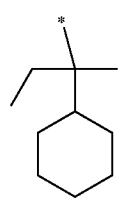

(r-pr-cs3) 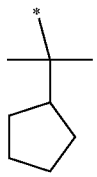

(r-pr-cs4) 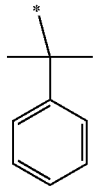

(r-pr-cs5) 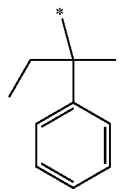

(r-pr-c1) 

(r-pr-c2) 

(r-pr-c3) 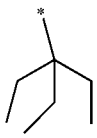

Examples of the acid dissociable group for protecting a hydroxy group among the aforementioned polar group include the acid dissociable group represented by general formula (a1-r-3) shown below (hereinafter, referred to as "tertiary alkyloxycarbonyl-type acid dissociable group").

[Chemical formula 11]

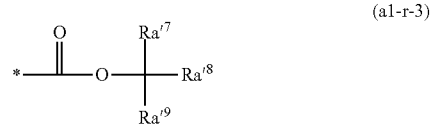

(a1-r-3)

In the formula, $Ra'^7$ to $Ra'^9$ each independently represent an alkyl group. * means a valence bond.

In formula (a1-r-3), $Ra'^7$ to $Ra'^9$ is preferably an alkyl group having 1 to 5 carbon atoms, and more preferably an alkyl group having 1 to 3 carbon atoms.

Further, the total number of carbon atoms within each alkyl group is preferably 3 to 7, more preferably 3 to 5, and most preferably 3 or 4.

Examples of the structural unit (a1) include a structural unit derived from an acrylic ester which may have a substutunet which substitutes the hydrogen atom bonded to the carbon atom on the α-position and contains an acid decomposable group which exhibits increased polarity by the action of an acid; a structural unit derived from hydroxystyrene or a hydroxystyrene derivative in which at least a part of the hydrogen atom of the hydroxy group is protected with a substituent containing an acid decomposable group; and a structural unit derived from vinylbenzoic acid or a vinylbenzoic acid derivative in which at least a part of the hydrogen atom within —C(=O)—OH is protected with a substituent containing an acid decomposable group.

As the structural unit (a1), among the above, a structural unit derived from acrylic ester in which the hydrogen atom bonded to the carbon atom on the α-position may be substituted with a substituent, is preferable.

As the structural unit (a1), a structural unit represented by general formula (a1-1) or (a1-2) shown below is preferable.

[Chemical formula 12]

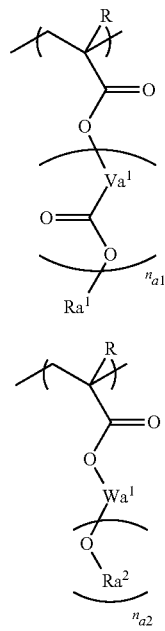

(a1-1)

(a1-2)

In the formulae, R represents a hydrogen atom, an alkyl group having 1 to 5 carbon atoms or a halogenated alkyl group having 1 to 5 carbon atoms. $Va^1$ represents a divalent hydrocarbon group which may have an ether bond, a urethane bond, or an amide bond; $n_{a1}$ is 0 to 2; and $Ra^1$ represents an acid dissociable group represented by formulae (a1-r-1) and (a1-r-2).

$Wa^1$ represents a hydrocarbon group having a valenccy of $n_{a2}+1$; $n_{a2}$ is 1 to 3; and $Ra^2$ represents an acid dissociable group represented by formula (a1-r-1) or (a1-r-3).

In general formula (a1-1), the alkyl group having 1 to 5 carbon atoms is preferably a linear or branched alkyl group having 1 to 5 carbon atoms, and specific examples thereof include a methyl group, an ethyl group, a propyl group, an isopropyl group, a n-butyl group, an isobutyl group, a tert-butyl group, a pentyl group, an isopentyl group, and a neopentyl group. The halogenated alkyl group having 1 to 5 carbon atoms is a group in which a part or all of the hydrogen atoms of the alkyl group having 1 to 5 carbon atoms are substituted with a halogen atom. Examples of the halogen atom include a fluorine atom, a chlorine atom, a bromine atom, and an iodine atom, and in particular, a fluorine atom is preferable.

As R, a hydrogen atom, an alkyl group having 1 to 5 carbon atoms, or a fluorinated alkyl group having 1 to 5 carbon atoms is preferable, and a hydrogen atom or a methyl group is most preferable in view of industrial availability.

A hydrocarbon group of $Va^1$ may be an aliphatic hydrocarbon group or an aromatic hydrocarbon group. The aliphatic hydrocarbon group means a group that has no aromaticity. The aliphatic hydrocarbon group as the divalent hydrocarbon group for $Va^1$ may be saturated or unsaturated, but commonly, is preferably saturated.

The specific examples of the aliphatic hydrocarbon group include a linear or branched aliphatic hydrocarbon group and an aliphatic hydrocarbon group including a ring in the structure thereof.

In addition, as $Va^1$, a group having the aforementioned divalent hydrocarbon group bonded thereto via an ether bond, a urethane bond, or an amide bond can be used.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group having 1 to 5 carbon atoms is preferable.

As the aliphatic hydrocarbon group containing a ring in the structure thereof, an alicyclic hydrocarbon group (a group in which two hydrogen atoms are removed from an aliphatic hydrocarbon ring), a group in which the alicyclic hydrocarbon group is bonded to the terminal of the aforementioned linear or branched aliphatic hydrocarbon group, and a group in which the alicyclic hydrocarbon group is interposed within the aforementioned linear or branched aliphatic hydrocarbon group, can be exemplified. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic alicyclic hydrocarbon group, a group in which two hydrogen atoms are removed from monocycloalkane is preferable. The monocycloalkane preferably has 3 to 6 carbon atoms, and specific examples thereof include cyclopentane and cyclohexane. As the polycyclic alicyclic hydrocarbon group, a group in which two hydrogen atoms are removed from polycycloalkane is preferable, and the polycycloalkane preferably has 7 to 12 carbon atoms. Specific examples of the polycycloalkane include adamantane, norbornane, isobornane, tricyclodecane and tetracyclododecane.

The aromatic hydrocarbon group is a hydrocarbon group having an aromatic ring.

The aromatic hydrocarbon group as the divalent hydrocarbon group for $Va^1$ preferably has 3 to 30 carbon atoms, more preferably 5 to 30, still more preferably 5 to 20, particularly preferably 6 to 15, and most preferably 6 to 10. Here, the number of carbon atoms within a substituent is not included in the number of carbon atoms of the aromatic hydrocarbon group.

Specific examples of the aromatic ring contained in the aromatic hydrocarbon group include aromatic hydrocarbon rings, such as benzene, biphenyl, fluorene, naphthalene, anthracene and phenanthrene; and aromatic hetero rings in which a part of the carbon atoms constituting the aforementioned aromatic hydrocarbon rings is substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms are removed from the aforementioned aromatic hydrocarbon ring (arylene group); and a group in which one hydrogen atom is removed from the aforementioned aromatic hydrocarbon ring (aryl group) and the one hydrogen atom is substituted with an alkylene group (a group in which one hydrogen atom is removed from an aryl group in an arylalkyl group such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atoms, more preferably 1 or 2, and particularly preferably 1.

In formula (a1-2), the hydrocarbon group for $Wa^1$ having a valency of $n_{a2}+1$ may be either an aliphatic hydrocarbon group or an aromatic hydrocarbon group. The aliphatic hydrocarbon group refers to a hydrocarbon group that has no aromaticity, and may be either saturated or unsaturated, but in general, is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As specific examples thereof, the same groups as those described above for $Va^1$ in formula (a1-1) can be exemplified.

The valency of $n_{a2}+1$ is preferably divalent, trivalent or tetravalent, and divalent or trivalent is more preferable.

As formula (a1-2), a structural unit represented by general formula (a1-2-01) shown below is particularly preferable.

[Chemical formula 13]

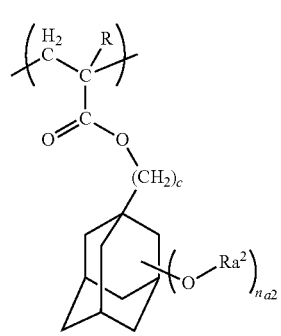

(a1-2-01)

In formula (a1-2-01), $Ra^2$ represents an acid dissociable group represented by formula (a1-r-1) or (a1-r-3); $n_{a2}$ is an integer of 1 to 3, preferably 1 or 2, and more preferably 1; c is an integer of 0 to 3, preferably 0 or 1, and more preferably 1; and R is the same as defined above.

Specific examples of formulae (a1-1) and (a1-2) are shown below. In the respective formulae shown below, $R^\alpha$ represents a hydrogen atom, a methyl group or a trifluoromethyl group.

[Chemical formula 14]

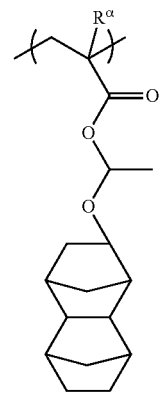

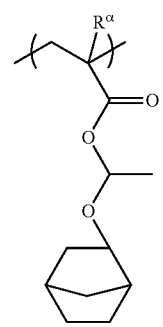

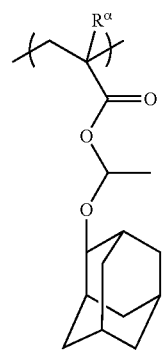

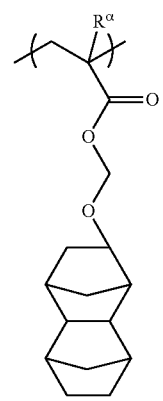

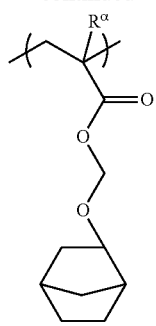
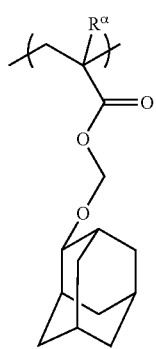
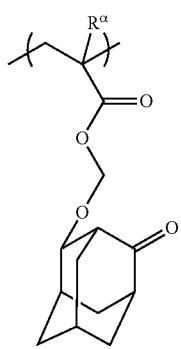
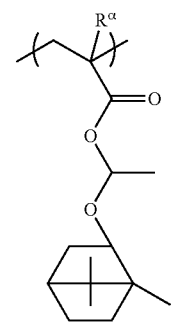
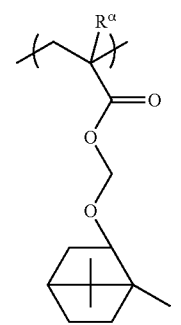
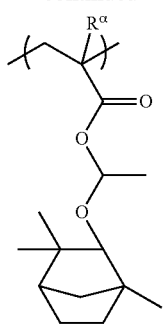
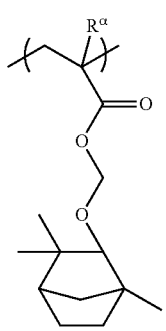
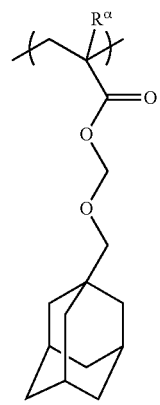
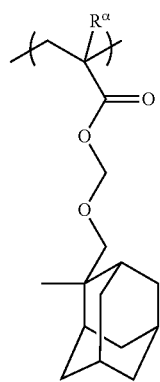

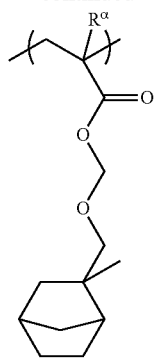
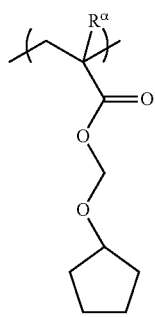
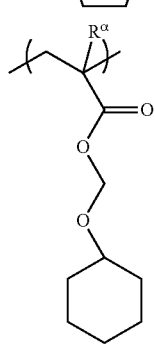
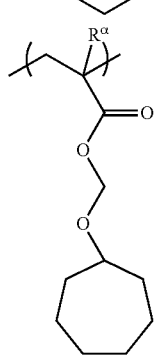
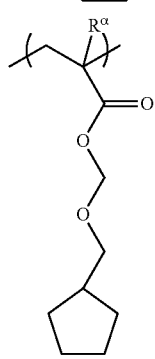
[Chemical formula 15]
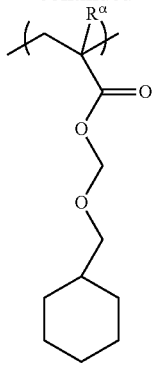
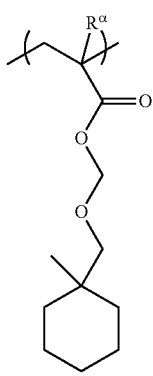
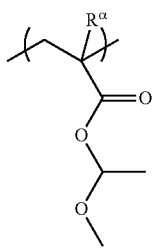
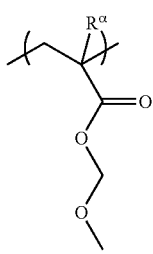
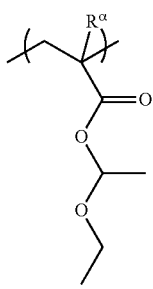

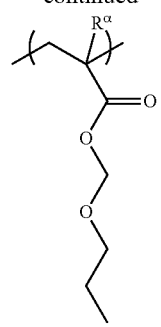
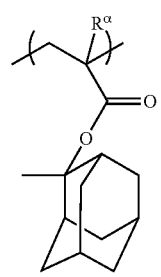
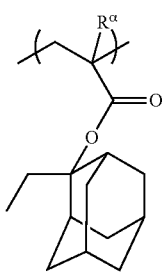
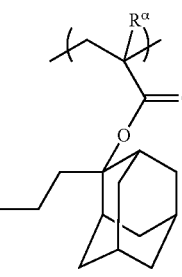
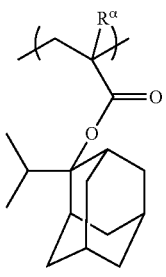
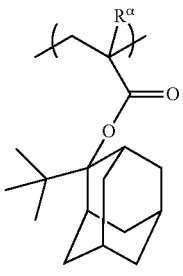
[Chemical formula 16]
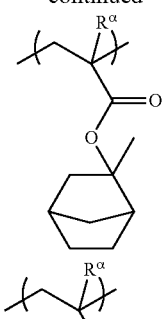
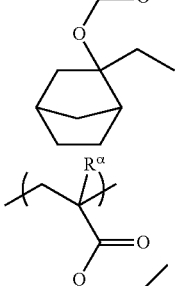
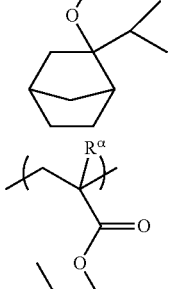
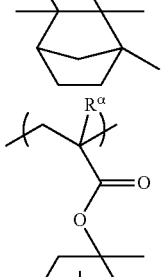
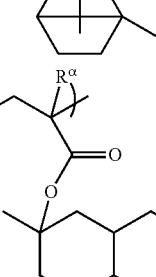
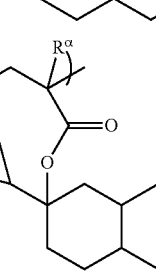

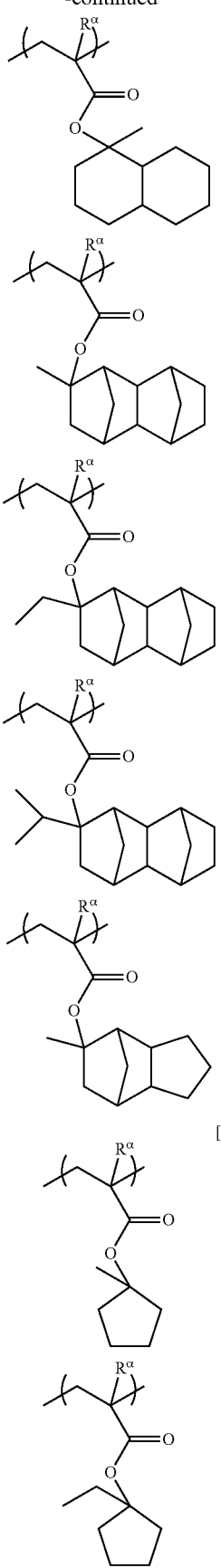
[Chemical formula 17]
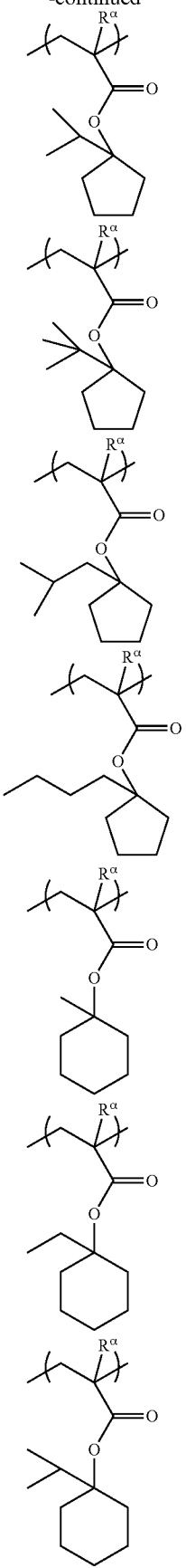

-continued
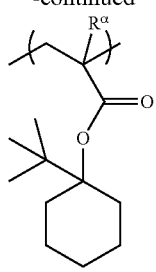
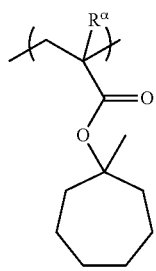
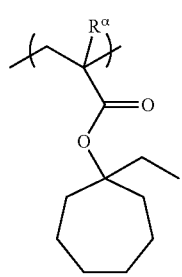
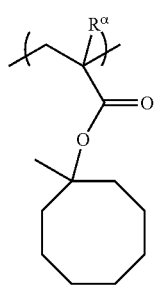
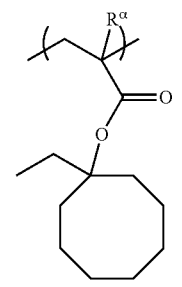
-continued
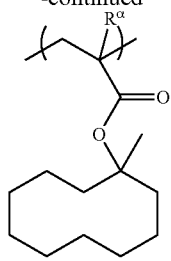
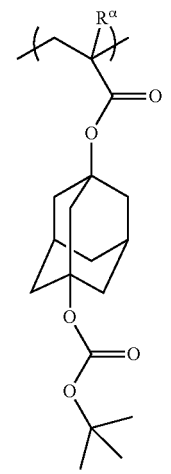
[Chemical formula 18]
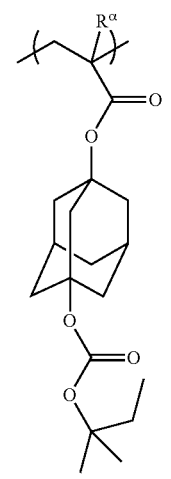

31
-continued
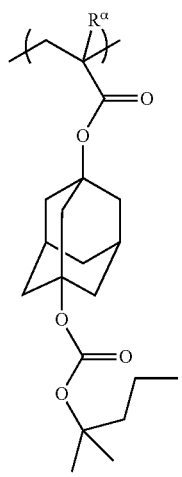
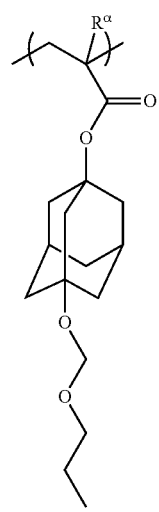
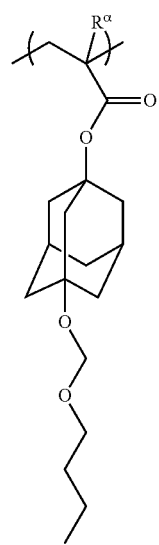
32
-continued
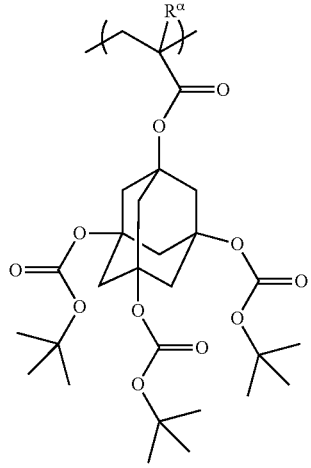
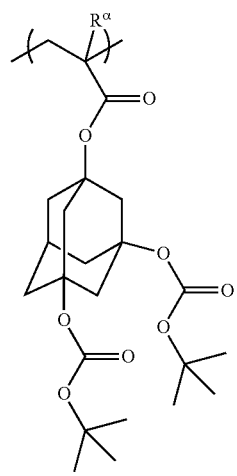
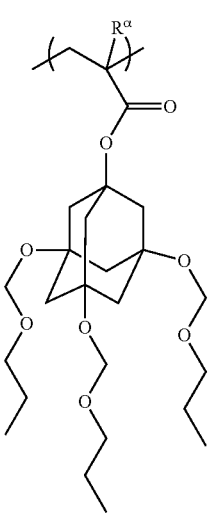

-continued

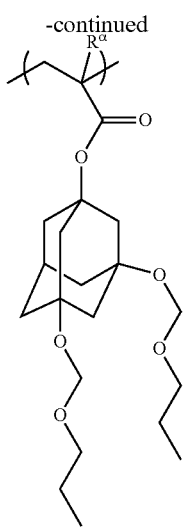

The ratio of the structural unit (a1) in the component (A) is preferably 20 mol % to 80 mol %, more preferably 20 mol % to 75 mol %, and still more preferably 25 mol % to 70 mol % with respect to all of the structural units constituting the component (A). By ensuring the lower limit, various lithography properties such as sensitivity, resolution and LWR are improved. On the other hand, if the amount of the structural unit (a1) is no more than the upper limit of the aforementioned range, a good balance can be achieved with the other structural units.

Structural Unit (a2)

In the present invention, the base material component preferably contains a structural unit (a2) having a $—SO_2$-containing cyclic group, a lactone-containing cyclic group, a carbonate-containing cyclic group, or a heterocyclic group other than the above groups.

The $—SO_2$-containing cyclic group, the lactone-containing cyclic group, the carbonate-containing cyclic group, or the heterocyclic group other than these in the structural unit (a2) is effective for increasing adhesiveness of the resist film to a substrate, in the case where the component (A) is used for forming a resist film.

In addition, in the case where the structural unit (a1) described below contains the $—SO_2$-containing cyclic group, the lactone-containing cyclic group, the carbonate-containing cyclic group, or the heterocyclic group other than these in the structure thereof, the structural unit corresponds to a structural unit (a2); however, such a structural unit corresponds to the structural unit (a1) not the structural unit (a2).

As the structural unit (a2), a structural unit represented by general formula (a2-1) shown below is preferable.

[Chemical formula 19]

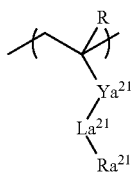

(a2-1)

In the formula, R represents a hydrogen atom, an alkyl group having 1 to 5 carbon atoms, or a halogenated alkyl group having 1 to 5 carbon atoms; $Ya^{21}$ represents a single bond or a divalent linking group; $La^{21}$ represents —O—, —COO—, —CON(R')—, —OCO—, —CONHCO—, or —CONHCS—; and R' represents a hydrogen atom or a methyl group. However, in the case where $La^{21}$ represents —O—, $Ya^{21}$ does not represent —CO—; and $Ra^{21}$ represents a $—SO_2$-containing cyclic group, a lactone-containing cyclic group, a carbonate-containing cyclic group or a heterocyclic group other than these.

The divalent linking group for $Ya^{21}$ is not particularly limited, and preferable examples thereof include a divalent hydrocarbon group which may have a substituent and a divalent linking group containing a hetero atom.

Divalent Hydrocarbon Group Which May Have a Substituent

The hydrocarbon group as a divalent linking group may be either an aliphatic hydrocarbon group or an aromatic hydrocarbon group.

An aliphatic hydrocarbon group refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof. Specifically, groups exemplified above for $Va^1$ in formula (a1-1) can be exemplified.

The linear or branched aliphatic hydrocarbon group may or may not have a substituent. Examples of the substituent include a fluorine atom, a fluorinated alkyl group having 1 to 5 carbon atoms which is substituted with a fluorine atom, and a carbonyl group.

As the aliphatic hydrocarbon group containing a ring in the structure thereof, a cyclic aliphatic hydrocarbon group containing a hetero atom in the ring structure thereof and may have a substituent (a group in which two hydrogen atoms are removed from an aliphatic hydrocarbon ring), a group in which the cyclic aliphatic hydrocarbon group is bonded to the terminal of the aforementioned linear or branched aliphatic hydrocarbon group, and a group in which the cyclic aliphatic group is interposed within the aforementioned linear or branched aliphatic hydrocarbon group, can be exemplified. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

Specific examples of the cyclic aliphatic hydrocarbon group include the same group as exemplified above for $Va^1$ in formula (a1-1).

The cyclic aliphatic hydrocarbon group may or may not have a substituent. Examples of the substituent include an alkyl group, an alkoxy group, a halogen atom, a halogenated alkyl group, a hydroxy group and a carbonyl group.

The alkyl group as the substituent is preferably an alkyl group having 1 to 5 carbon atoms, and a methyl group, an ethyl group, a propyl group, an n-butyl group or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom for the substituent include a fluorine atom, a chlorine atom, a bromine atom and an iodine atom, and a fluorine atom is preferable.

Examples of the halogenated alkyl group for the substituent include groups in which a part or all of the hydrogen atoms within the aforementioned alkyl groups are substituted with the aforementioned halogen atoms.

The cyclic aliphatic hydrocarbon group may have a part of the carbon atoms constituting the ring structure thereof substituted with a substituent containing a hetero atom. As the substituent containing a hetero atom, —O—, —C(=O)—O—, —S—, —S(=O)$_2$— or —S(=O)$_2$—O— is preferable.

Specific examples of the aromatic hydrocarbon group as a divalent hydrocarbon group include the same group as exemplified above for Va$^1$ in formula (a1-1).

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxy group.

The alkyl group as the substituent is preferably an alkyl group having 1 to 5 carbon atoms, and a methyl group, an ethyl group, a propyl group, an n-butyl group or a tert-butyl group is most preferable.

As the alkoxy group, the halogen atom and the halogenated alkyl group for the substituent, the same groups exemplified as the aforementioned substituents for substituting a hydrogen atom within the cyclic aliphatic hydrocarbon group can be used.

Divalent Linking Group Containing a Hetero Atom

With respect to a divalent linking group containing a hetero atom, a hetero atom is an atom other than a carbon atom and a hydrogen atom, and examples thereof include an oxygen atom, a nitrogen atom, a sulfur atom and a halogen atom.

In the case where Ya$^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (wherein H may be substituted with a substituent such as an alkyl group or an acyl group), —S—, —S(=O)$_2$—, —S(=O)$_2$—O—, a group represented by general formula —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m'}$—Y$^{22}$— or —Y$^{21}$—O—C(=O)—Y$^{22}$—. In the formulae, Y$^{21}$ and Y$^{22}$ each independently represent a divalent hydrocarbon group which may have a substituent, and O represents an oxygen atom; and m' represents an integer of 0 to 3.

In the case where the divalent linking group containing a hetero atom represents —C(=O)—NH—, —NH—, or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8, and particularly preferably 1 to 5.

In formula —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m'}$—Y$^{22}$— or —Y$^{21}$—O—C(=O)—Y$^{22}$—, Y$^{21}$ and Y$^{22}$ each independently represent a divalent hydrocarbon group which may have a substituent. Examples of the divalent hydrocarbon group include the same groups as those described above as the "divalent hydrocarbon group which may have a substituent" in the explanation of the aforementioned divalent linking group.

As Y$^{21}$, a linear aliphatic hydrocarbon group is preferable, a linear alkylene group is more preferable, a linear alkylene group having 1 to 5 carbon atoms is still more preferable, and a methylene group or an ethylene group is particularly preferable.

As Y$^{22}$, a linear or branched aliphatic hydrocarbon group is preferable, and a methylene group, an ethylene group or an alkylmethylene group is more preferable. The alkyl group within the alkylmethylene group is preferably a linear alkyl group having 1 to 5 carbon atoms, more preferably a linear alkyl group having 1 to 3 carbon atoms, and most preferably a methyl group.

In the group represented by formula —[Y$^{21}$—C(=O)—O]$_{m'}$—Y$^{22}$—, m' represents an integer of 0 to 3, preferably an integer of 0 to 2, more preferably 0 or 1, and most preferably 1. Namely, it is particularly preferable that the group represented by formula —[Y$^{21}$—C(=O)—O]$_{m'}$—Y$^{22}$— is a group represented by formula —Y$^{21}$—C(=O)—O—Y$^{22}$—. Among these, a group represented by formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

In the present invention, Ya$^{21}$ preferably represents a single bond, an ester bond [—C(=O)—O—], an ether bond (—O—), a linear or branched alkylene group, or a combination of these.

In formula (a2-1), Ra$^{21}$ represents a —SO$_2$-containing cyclic group, a lactone-containing cyclic group, a heterocyclic group, or a carbonate-containing cyclic group.

The "—SO$_2$-containing cyclic group" refers to a cyclic group including a ring having —SO$_2$— in the ring skeleton thereof, and specifically, a cyclic group in which a sulfur atom (S) within —SO$_2$— forms a part of the ring skeleton of the cyclic group. If the ring having —SO$_2$— in the ring skeleton thereof is counted as a first ring, in the case where the group has only that ring, the group is referred to as a monocyclic group, and in the case where the group has other ring structures, the group is referred to as a polycyclic group regardless of its structure. The —SO$_2$-containing cyclic group may be monocyclic or polycyclic.

The —SO$_2$-containing cyclic group is particularly preferably a cyclic group including —O—SO$_2$— in its ring skeleton, that is, a cyclic group including a sultone ring in which —O—S— in —O—SO$_2$— forms a part of the ring skeleton. The specific examples of the —SO$_2$-containing cyclic group include each group represented by general formulae (a5-r-1) to (a5-r-4) shown below.

[Chemical formula 20]

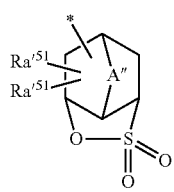

(a5-r-1)

(a5-r-2)

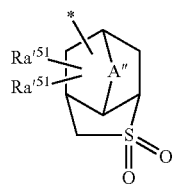

(a5-r-3)

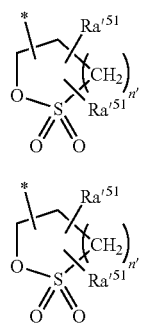

(a5-r-4)

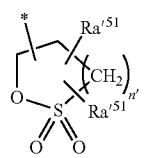

In the formula, each $Ra'^{51}$ independently represents a hydrogen atom, an alkyl group, an alkoxy group, a halogen atom, a halogenated alkyl group, a hydroxy group, —COOR", —OC(=O)R", a hydroxyalkyl group, or a cyano group; R" represents a hydrogen atom or an alkyl group; A" represents an oxygen atom, a sulfur atom, or an alkylene group having 1 to 5 carbon atoms which may have an oxygen atom or a sulfur atom; and n' is an integer of 0 to 2.

In general formulae (a5-r-1) to (a5-r-4), A" is the same as A" in general formulae (a2-r-1) to (a2-r-7) shown below. An alkyl group, an alkoxy group, a halogen atom, a halogenated alkyl group, —COOR", —OC(=O)R", and a hydroxyalkyl group for $Ra'^{51}$ are the same as those of $Ra'^{21}$ in general formulae (a2-r-1) to (a2-r-7) shown below.

Specific examples of each group represented by the following general formulae (a5-r-1) to (a5-r-4) are shown. "Ac" in the formulae represents an acetyl group.

[Chemical formula 21]

(r-s1-1-1)

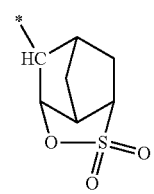

(r-s1-1-2)

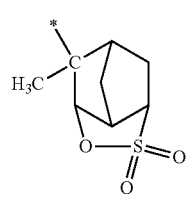

(r-s1-1-3)

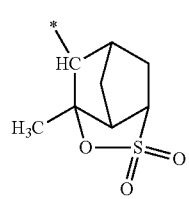

(r-s1-1-4)

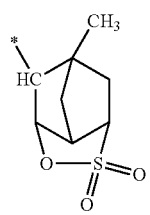

(r-s1-1-5)

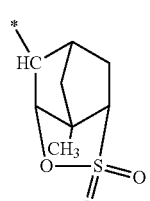

(r-s1-1-6)

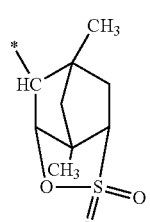

(r-s1-1-7)

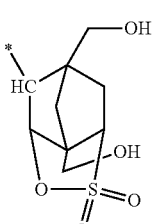

(r-s1-1-8)

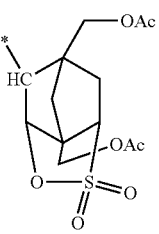

(r-s1-1-9)

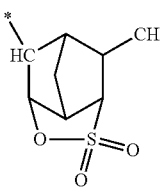

(r-s1-1-10)

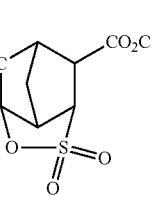

-continued
(r-s1-1-11)
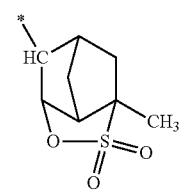
(r-s1-1-12)
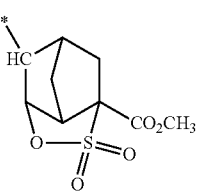
(r-s1-1-13)
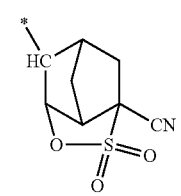
(r-s1-1-14)
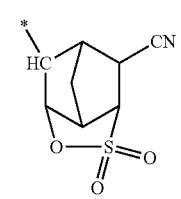
(r-s1-1-15)
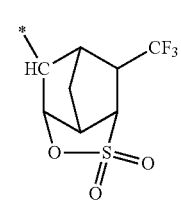
(r-s1-1-16)
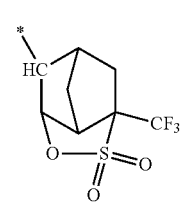
(r-s1-1-17)
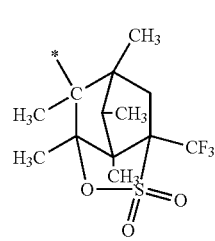
(r-s1-1-18)
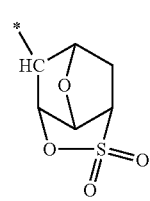
-continued
(r-s1-1-19)
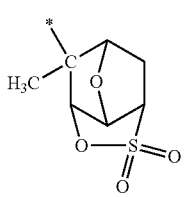
(r-s1-1-20)
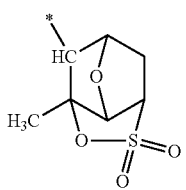
(r-s1-1-21)
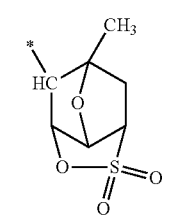
[Chemical formula 22]
(r-s1-1-22)
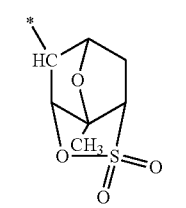
(r-s1-1-23)
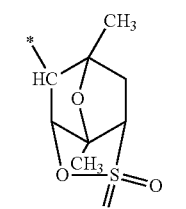
(r-s1-1-24)
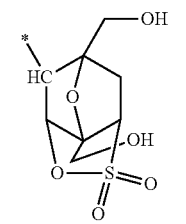
(r-s1-1-25)
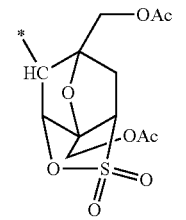

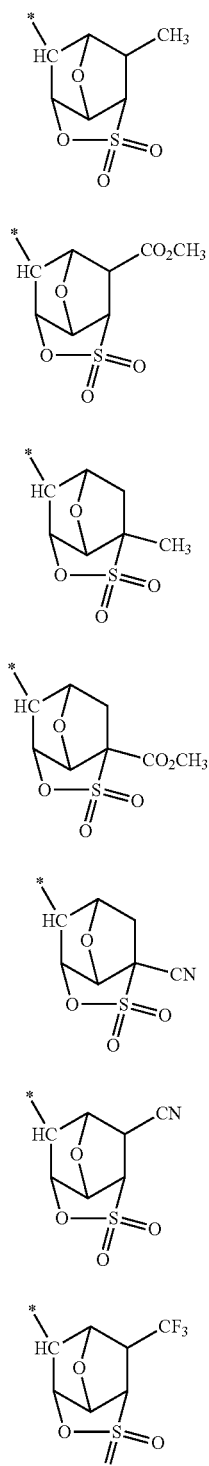

In the present invention, in the case where the structural unit (a2) contains a —SO$_2$-containing cyclic group, the structural unit is not particularly limited, as long as a log P value of an acrylic ester monomer including a —SO$_2$-containing cyclic group is less than 1.2. Among the above, the group represented by general formula (a5-r-1) is preferable, at least one group selected from the group consisting of groups represented by any one of Chemical formulae (r-sl-1-1), (r-sl-1-18), (r-sl-3-1), and (r-sl-4-1) is more preferably used, and the group represented by Chemical formula (r-sl-1-1) is most preferable.

The "lactone-containing cyclic group" refers to a cyclic group including a ring (lactone ring) having —O—C(=O)— in the ring skeleton thereof. If the ring having a lactone ring in the ring skeleton thereof is counted as a first ring, in the case where the group has only the lactone ring, the group is referred to as a monocyclic group, and in the case where the group has other ring structures, the group is referred to as a polycyclic group regardless of its structure. The lactone-containing cyclic group may be monocyclic or polycyclic.

The lactone-containing cyclic group is not particularly limited, and an arbitrary group can be used. Specifically, each group represented by general formulae (a2-r-1) to (a2-r-7) shown below can be exemplified. Hereinafter, "*" represents a valence bond.

[Chemical formula 24]

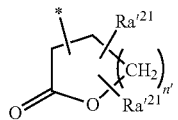

(a2-r-2)
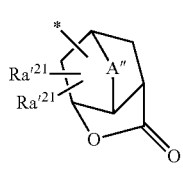

(a2-r-3)
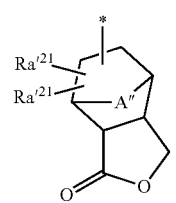

(a2-r-4)
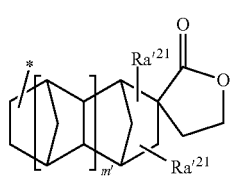

(a2-r-5)
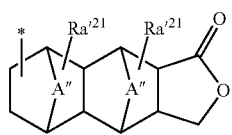

(a2-r-6)
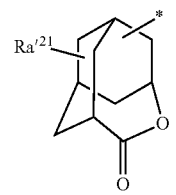

(a2-r-7)
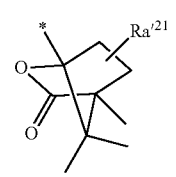

In the formulae, each Ra'$^{21}$ independently represents a hydrogen atom, an alkyl group, an alkoxy group, a halogen atom, a halogenated alkyl group, a hydroxy group, —COOR", —OC(═O) R", a hydroxyalkyl group, or a cyano group; R" represents a hydrogen atom or an alkyl group; A" represents an alkylene group having 1 to 5 carbon atoms which may have an oxygen atom or a sulfur atom, an oxygen atom, or a sulfur atom; n' is an integer of 0 to 2; and m' is 0 or 1.

In general formulae (a2-r-1) to (a2-r-7), A" represents an alkylene group having 1 to 5 carbon atoms which may have an oxygen atom (—O—) or a sulfur atom (—S—), an oxygen atom, or a sulfur atom. As the alkylene group having 1 to 5 carbon atoms for A", a linear or branched alkylene group is preferable, and examples thereof include a methylene group, an ethylene group, an n-propylene group, and an isopropylene group. In the case where the alkylene group includes an oxygen atom or a sulfur atom, specific examples thereof include groups in which —O— or —S— is interposed within the aforementioned alkylene group terminal or carbon atom such as —O—CH$_2$—, —CH$_2$—O—CH$_2$—, —S—CH$_2$—, and —CH$_2$—S—CH$_2$—. As A", the alkylene group having 1 to 5 carbon atoms or —O— is preferable, the alkylene group having 1 to 5 carbon atoms is more preferable, and the methylene group is most preferable. Each Ra'$^{21}$ independently represents an alkyl group, an alkoxy group, a halogen atom, a halogenated alkyl group, —COOR", —OC(═O)R", a hydroxyalkyl group, or a cyano group.

As the alkyl group for Ra'$^{21}$, an alkyl group having 1 to 5 carbon atoms is preferable.

As the alkoxy group for Ra'$^{21}$, an alkoxy group having 1 to 6 carbon atoms is preferable.

The alkoxy group is preferable linear or branched. Specifically, a group in which the alkyl group mentioned as the alkyl group for Ra'$^{21}$ and an oxygen atom (—O—) are linked to each other can be exemplified.

As the halogen atom for Ra'$^{21}$, examples thereof include a fluorine atom, a chlorine atom, a bromine atom, and an iodine atom, and a fluorine atom is preferable.

As the halogenated alkyl group for Ra'$^{21}$, a group in which a part or all of the hydrogen atoms of an alkyl group for Ra'$^{21}$ are substituted with the halogen atom can be exemplified. As the halogenated alkyl group, a fluorinated alkyl group is preferable and a perfluoroalkyl group is particularly preferable.

Specific examples of the each group represented by the following general formulae (a2-r-1) to (a2-r-7) are shown.

[Chemical formula 25]

(r-Ic-1-1)
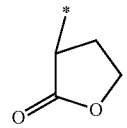

(r-Ic-1-2)
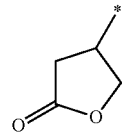

(r-Ic-1-3)
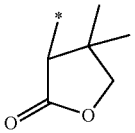

(r-Ic-1-4)
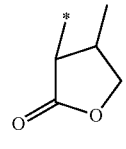

(r-Ic-1-5)
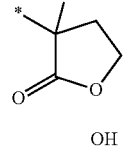

(r-Ic-1-6)
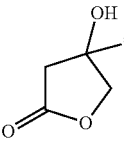

(r-Ic-1-7)
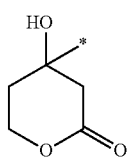
(r-Ic-2-1)
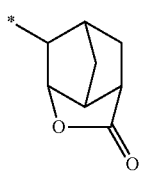
(r-Ic-2-2)
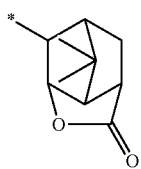
(r-Ic-2-3)
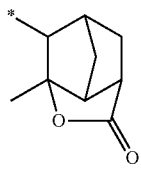
(r-Ic-2-4)
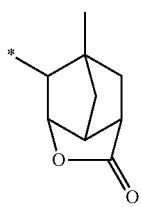
(r-Ic-2-5)
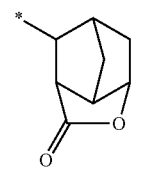
(r-Ic-2-6)
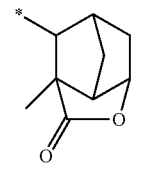
(r-Ic-2-7)
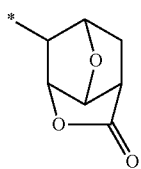
(r-Ic-2-8)
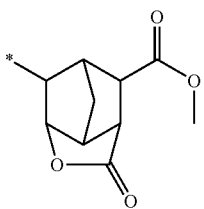
(r-Ic-2-9)
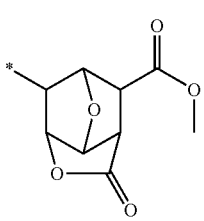
(r-Ic-2-10)
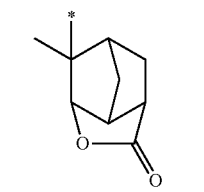
(r-Ic-2-11)
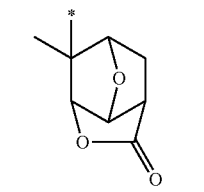
(r-Ic-2-12)
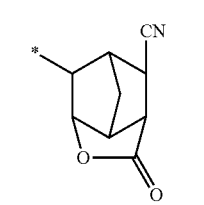
(r-Ic-2-13)
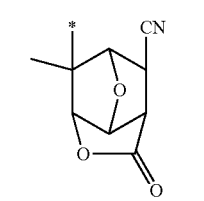
(r-Ic-3-1)
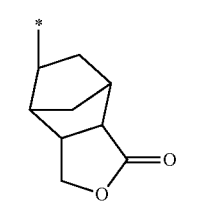
(r-Ic-3-2)
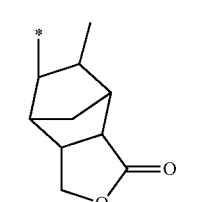

47
-continued
(r-Ic-3-3)
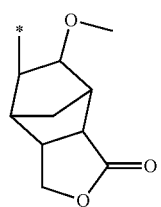
(r-Ic-3-4)
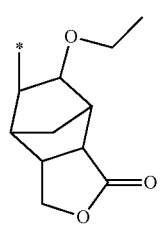
(r-Ic-3-5)
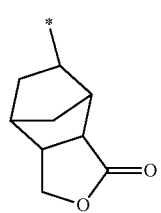
(r-Ic-4-1)
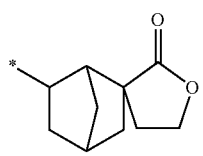
(r-Ic-4-2)
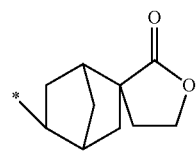
(r-Ic-4-3)
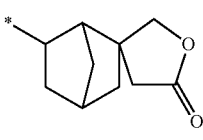
(r-Ic-4-4)
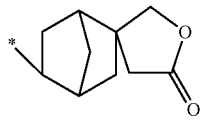
(r-Ic-4-5)
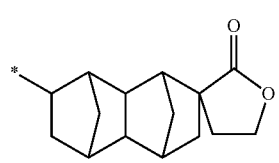
(r-Ic-4-6)
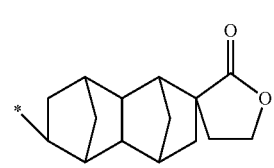
48
-continued
(r-Ic-4-7)
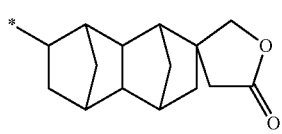
(r-Ic-4-8)
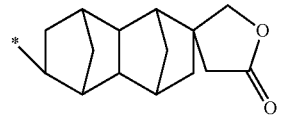
(r-Ic-4-9)
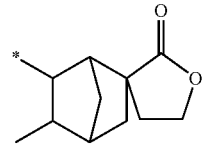
(r-Ic-5-1)
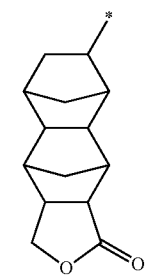
(r-Ic-5-2)
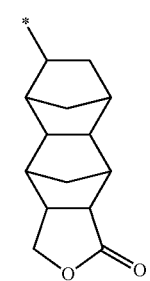
(r-Ic-5-3)
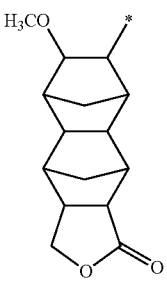
(r-Ic-5-4)
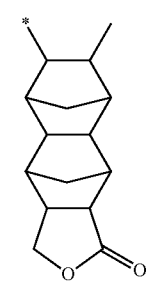

(r-Ic-6-1)

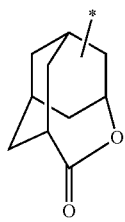

(r-Ic-7-1)

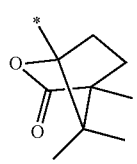

In the present invention, as the structural unit (a2), each group represented by general formula (a2-r-1) or (a2-r-2) is preferable, and each group represented by Chemical formula (r-lc-1-1) or (r-lc-2-7) is more preferable.

The "carbonate-containing cyclic group" refers to a cyclic group including a ring (carbonate ring) having —O—C(=O)—O— in the ring skeleton thereof. If the ring having a carbonate ring in the ring skeleton thereof is counted as a first ring, in the case where the group has only the carbonate ring, the group is referred to as a monocyclic group, and in the case where the group has other ring structures, the group is referred to as a polycyclic group regardless of its structure. The carbonate-containing cyclic group may be monocyclic or polycyclic.

The carbonate-containing cyclic group as the cyclic hydrocarbon group for $R^1$ is not particularly limited, and an arbitrary group may be used. Specific examples include groups represented by general formulae (ax3-r-1) to (ax3-r-3) shown below.

[Chemical formula 26]

(ax3-r-1)

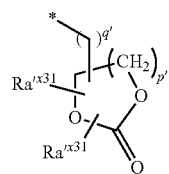

(ax3-r-2)

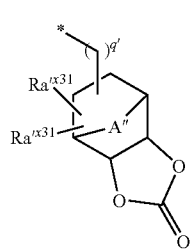

(ax3-r-3)

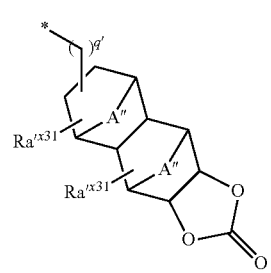

In the formulae, each $Ra'^{x31}$ independently represents a hydrogen atom, an alkyl group, an alkoxy group, a halogen atom, a halogenated alkyl group, a hydroxy group, —COOR″, —OC(=O)R″, a hydroxyalkyl group or a cyano group; R″ represents a hydrogen atom or an alkyl group; A″ represents an alkylene group of 1 to 5 carbon atoms which may have an oxygen atom or a sulfur atom, an oxygen atom, or a sulfur atom; and q' represents 0 or 1.

In general formulae (ax3-r-1) to (ax3-r-3), A″ is the same as defined for A″ in general formula (a2-r-1).

Examples of the alkyl group, alkoxy group, halogen atom, halogenated alkyl group, —COOR″, —OC(=O)R″ and hydroxyalkyl group for $Ra'^{31}$ include the same groups as those described above in the explanation of $Ra'^{21}$ in general formulae (a2-r-1) to (a2-r-7), respectively.

Specific examples of the groups represented by general formulae (ax3-r-1) to (ax3-r-3) are shown below.

[Chemical formula 27]

(r-cr-1-1)

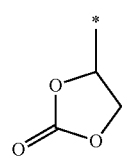

(r-cr-1-2)

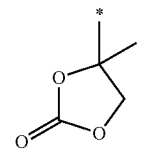

(r-cr-1-3)

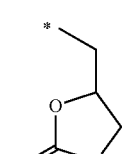

(r-cr-1-4)

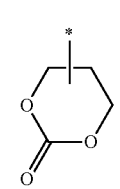

(r-cr-1-5)
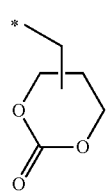
(r-cr-1-6)
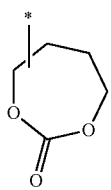
(r-cr-1-6)
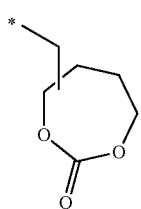
(r-cr-2-1)
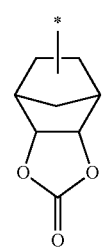
(r-cr-2-2)
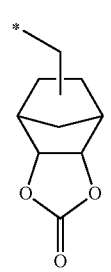
(r-cr-2-3)
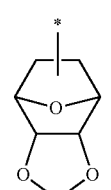
(r-cr-2-4)
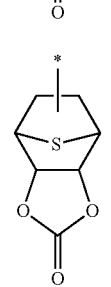
(r-cr-3-1)
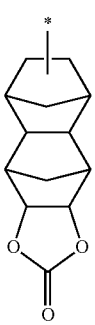
(r-cr-3-2)
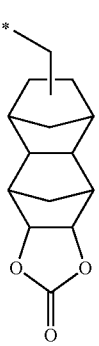
(r-cr-3-3)
(r-cr-3-4)
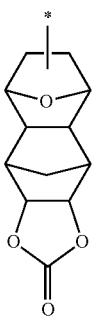
(r-cr-3-5)
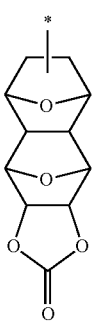

The "heterocyclic group" refers to a cyclic group including a carbon atom and at least one atom other than a carbon atom, and examples thereof include each heterocyclic group represented by (r-hr-1) to (r-hr-16) shown below and a nitrogen-containing heterocyclic group. As the nitrogen-containing heterocyclic group, a cycloalkyl group having 3 to 8 carbon atoms which may be substituted with one or two oxo groups can be exemplified. Preferred examples of the cycloalkyl group include 2,5-dioxopyrrolidine and 2,6-dioxopiperidine.

As the structural unit (a2) contained in the component (A1), one type of structural unit may be used, or two or more types may be used.

In the case where the component (A1) contains the structural unit (a2), the ratio of the structural unit (a2) is preferably 1 mol % to 80 mol %, more preferably 5 mol % to 70 mol %, still more preferably 10 mol % to 65 mol %, and particularly preferably 10 mol % to 60 mol % with respect to the total of all structural units constituting the component (A). If the ratio of the structural unit (a2) is equal to or more than the lower limit of the aforementioned range, the effect of using the structural unit (a2) can be sufficiently obtained, and if the ratio of the structural unit (a2) is equal to or less than the upper limit of the aforementioned range, a good balance can be achieved with the other structural units, and various lithography properties and pattern shape can be improved.

Structural Unit (a3)

The structural unit (a3) is a structural unit containing a polar group-containing aliphatic hydrocarbon group (however, the structural units that corresponds to the definition of structural units (a1) and (a2) are excluded).

If the component (A1) includes the structural unit (a3), it is presumed that the hydrophilicity of the component (A) is enhanced, thereby contributing to improvement in resolution.

Examples of the polar group include a hydroxy group, cyano group, carboxyl group, or hydroxyalkyl group in which part of the hydrogen atoms of the alkyl group are substituted with fluorine atoms, and a hydroxy group is particularly preferable.

Examples of the aliphatic hydrocarbon group include linear or branched hydrocarbon groups (preferably alkylene groups) having 1 to 10 carbon atoms, and cyclic aliphatic hydrocarbon groups (cyclic groups). These cyclic groups may be a monocyclic group or a polycyclic group, and can be selected appropriately from the multiple groups that have been proposed for the resins of resist compositions designed for use with ArF excimer lasers. The cyclic group is preferably a polycyclic group and more preferably has 7 to 30 carbon atoms.

Among the above, structural units derived from an acrylic ester that includes an aliphatic polycyclic group that contains a hydroxy group, a cyano group, a carboxyl group or a hydroxyalkyl group in which part of the hydrogen atoms of the alkyl group are substituted with a fluorine atom are more preferable. Examples of the polycyclic group include groups in which two or more hydrogen atoms are removed from bicycloalkane, tricycloalkane, tetracycloalkane or the like. Specific examples include groups in which two or more hydrogen atoms are removed from polycycloalkane such as adamantane, norbornane, isobornane, tricyclodecane or tetracyclododecane. Among these polycyclic groups, groups in which two or more hydrogen atoms are removed from adamantane, norbornane or tetracyclododecane are preferred industrially.

As the structural unit (a3), there is no particular limitation as long as the structural unit is a structural unit containing a polar group-containing aliphatic hydrocarbon group, and an arbitrary structural unit may be used.

The structural unit (a3) is preferably a structural unit which is derived from an acrylic ester, which may have a substituent substituting the hydrogen atom bonded to the carbon atom on the α-position, and which contains a polar group-containing aliphatic hydrocarbon group.

When the hydrocarbon group within the polar group-containing aliphatic hydrocarbon group is a linear or branched hydrocarbon group having 1 to 10 carbon atoms, the structural unit (a3) is preferably a structural unit derived from a hydroxyethyl ester of acrylic acid. When the hydrocarbon group is a polycyclic group, structural units represented by formulae (a3-1), (a3-2) and (a3-3) shown below are preferable.

[Chemical formula 28]

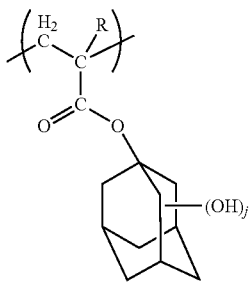

(a3-1)

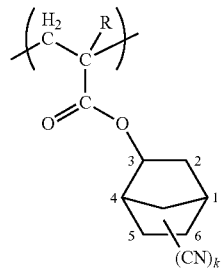

(a3-2)

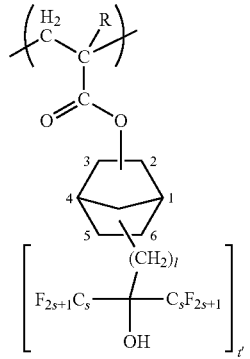

(a3-3)

In the formulae, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. In the case where j is 2, it is preferable that the hydroxy groups are bonded to the 3rd and 5th positions of the adamantyl group. In the case where j is 1, it is preferable that the hydroxy group is bonded to the 3rd position of the adamantyl group.

j is preferably 1, and it is particularly preferable that the hydroxy group is bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group is bonded to the terminal of the carboxy group of the acrylic acid. The fluorinated alkyl alcohol is preferably bonded to the 5th or 6th position of the norbornyl group.

As the structural unit (a3) contained in the component (A1), one type of structural unit may be used, or two or more types may be used.

The ratio of the structural unit (a3) within the component (A1) is preferably 5 mol % to 50 mol %, more preferably 5 mol % to 40 mol %, and still more preferably 5 mol % to 25 mol % with respect to the total of all structural units constituting the resin component (A1).

If the ratio of the structural unit (a3) is equal to or more than the lower limit of the aforementioned range, the effect of using the structural unit (a3) can be sufficiently obtained. On the other hand, if the ratio of the structural unit (a3) is equal to or less than the upper limit of the aforementioned range, a good balance can be achieved with the other structural units.

The component (A1) may have the following structural unit (a4) other than the aforementioned structural units (a1), (a2), and (a3).

Structural Unit (a4)

The structural unit (a4) is a structural unit containing an acid non-dissociable cyclic group. If the component (A1) includes the structural unit (a4), dry etching resistance of the resist pattern to be formed is improved. Further, the hydrophobicity of the component (A1) is further improved. It is considered that increase in the hydrophobicity contributes to improvement in terms of resolution, shape of the resist pattern and the like, particularly in an organic solvent developing process.

An "acid non-dissociable cyclic group" in the structural unit (a4) refers to a cyclic group which is not dissociated by the action of an acid generated from the component (B) described later upon exposure, and remains in the structural unit.

As the structural unit (a4), a structural unit which contains a non-acid-dissociable aliphatic cyclic group, and is also derived from an acrylic ester is preferable. Examples of this cyclic group include the same groups as those described above in relation to the aforementioned structural unit (a1), and any of the multiple conventional groups used within the resin component of resist compositions for ArF excimer lasers or KrF excimer lasers (and preferably for ArF excimer lasers) can be used.

In consideration of industrial availability and the like, at least one selected from the group consisting of a tricyclodecyl group, an adamantyl group, a tetracyclododecyl group, an isobornyl group, and a norbornyl group is particularly preferable. These polycyclic groups may be substituted with a linear or branched alkyl group having 1 to 5 carbon atoms.

Specific examples of the structural unit (a4) include structural units with structures represented by general formulae (a4-1) to (a4-7) shown below.

[Chemical formula 29]

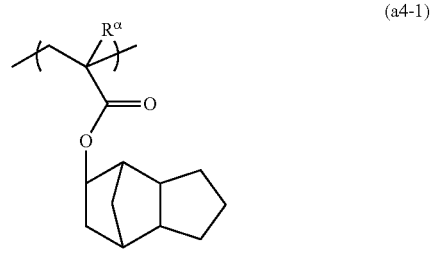

(a4-1)

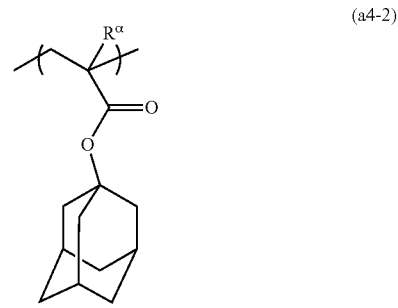

(a4-2)

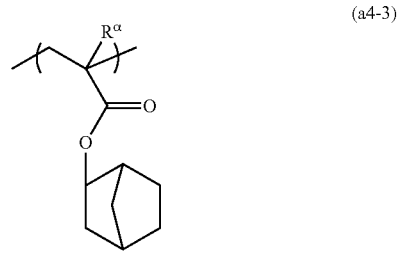

(a4-3)

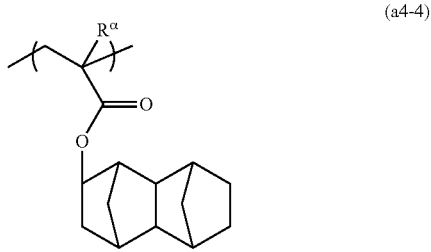

(a4-4)

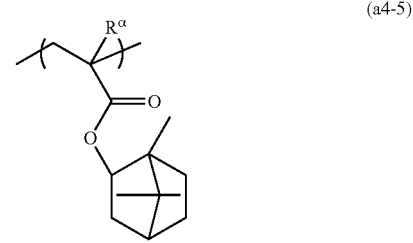

(a4-5)

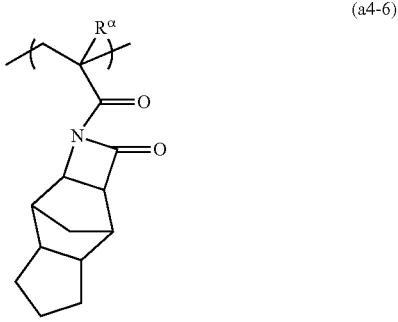

(a4-6)

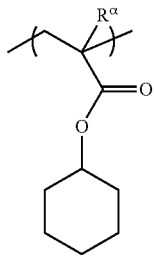

(a4-7)

In the formulae, $R^\alpha$ represents a hydrogen atom, a methyl group or a trifluoromethyl group.

As the structural unit (a4) contained in the component (A1), one type of structural unit may be used, or two or more types may be used.

In the case where the structural unit (a4) is included in the component (A1), the ratio of the structural unit (a4) is preferably within the range from 1 mol % to 30 mol % and more preferably from 10 mol % to 20 mol % with respect to the total of all the structural units that constitute the component (A1).

The component (A1) is preferably a copolymer containing (a1), (a2) and (a3).

The component (A1) can be obtained by performing polymerization, for example, the conventional radial polymerization which polymerizes a monomer deriving the respective structural units with a radical polymerization initiator such as azobisisobutyronitrille (AIBN) and azobisisobutyric acid dimethyl ester.

In addition, at the time of performing the aforementioned polymerization, by using a chain-transfer agent such as HS—CH$_2$—CH$_2$—CH$_2$—C(CF$_3$)$_2$—OH in combination, a —C(CF$_3$)$_2$—OH group may be introduced to the terminal of the component (A1). As such, a copolymer having the hydroxyalkyl group, in which part of the hydrogen atoms of an alkyl group are substituted with a fluorine atom, introduced thereto, is effective for reducing developing defects or LER (line edge roughness: nonuniform irregularities of the line side wall).

In the present invention, the weight average molecular weight (Mw) (in terms of the polystyrene determined by gel permeation chromatography) of the component (A1) is not particularly limited, but is preferably 1,000 to 50,000, more preferably 1,500 to 30,000, and most preferably 2,000 to 20,000. If the weight average molecular weight is equal to or less than the upper limit of the aforementioned range, the resist composition exhibits a satisfactory solubility in a resist solvent. If the weight average molecular weight is equal to or more than lower limit of the aforementioned range, dry etching resistance and the cross-sectional shape of the resist pattern becomes satisfactory.

As the component (A1), one type of the compound may be used alone, or two or more types thereof may be used in combination.

The ratio of the component (A1) in the base material component (A) is preferably 25 mass % or more, more preferably 50 mass %, still more preferably 75 mass %, and may be 100 mass % with respect to the total mass of the base material component (A). If the ratio is 25 mass % or more, the lithography properties are further improved.

In the present invention, as the component (A), one type of the compound may be used alone, or two or more types thereof may be used in combination.

In the present invention, the content of the component (A) can be adjusted depending on the thickness of the resist film to be formed, and the like.

Acid Generator Component; a Component (B)

The resist composition of the present invention contains an acid generator component (B) which generates an acid upon exposure (hereinafter, referred to as a component (B)). The component (B) is not particularly limited, and the components which have been proposed so far as the acid generator for a chemically amplified type resist can be used.

Examples of the acid generator include various acid generators including an onium salt-based acid generator such as an iodonium salt and a sulfonium salt, an oxime sulfonate-based acid generator, a diazomethane-based acid generator such as bisalkyl or bisaryl sulfonyl diazomethanes and poly(bissulfonyl)diazomethanes, a nitrobenzyl sulfonate-based acid generator, an iminosulfonate-based acid generator, and a disulfone-based acid generator. Among these, an onium salt-based acid generator is preferably used.

As the onium salt-based acid generator, for example, a compound represented by general formula (b-1) shown below (hereinafter, referred to as "component (b-1)"), a compound represented by general formula (b-2) (hereinafter, referred to as "component (b-2)"), or a compound represented by general formula (b-3) (hereinafter, referred to as "component (b-3)") can be used.

[Chemical formula 30]

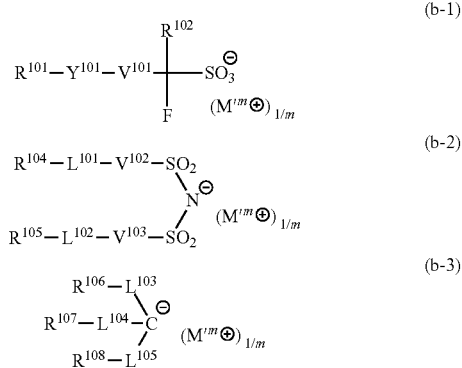

In the formulae, $R^{101}$, $R^{104}$ to $R^{108}$ each independently represent a cyclic group which may have a substituent, a chain-like alkyl group which may have a substituent, or a chain-like alkenyl group which may have a substituent. $R^{104}$ and $R^{105}$ may be bonded to each other to form a ring. Two of either $R^{106}$ or $R^{107}$ may be bonded to each other to form a ring. $R^{102}$ represents a fluorine atom or a fluorinated alkyl group having 1 to 5 carbon atoms. $Y^{101}$ represents a single bond or a divalent linking group including an oxygen atom. $V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO—, or —SO$_2$—. $M^{m+}$ represents an organic cation having a valency of m.

Anion Moiety

Anion Moiety of Component (b-1)

In formula (b-1), $R^{101}$ represents a cyclic group which may have a substituent, a chain-like alkyl group which may have a substituent, or a chain-like alkenyl group which may have a substituent.

Cyclic Group which may have a Substituent for $R^{101}$

The cyclic group is preferably a cyclic hydrocarbon group, and the cyclic hydrocarbon group may be an aromatic hydrocarbon group or an aliphatic hydrocarbon group.

Examples of the aromatic hydrocarbon group for $R^{101}$ include an aryl group in which one hydrogen atom is removed from an aromatic compound including two or more aromatic rings or an aromatic hydrocarbon ring mentioned as the divalent aromatic hydrocarbon group for $Va^1$ in formula (a1-1), and a phenyl group or naphthyl group is preferable.

Examples of the cyclic aliphatic hydrocarbon group for $R^{101}$ include a group in which one hydrogen atom is removed from monocycloalkane or polycycloalkane mentioned as the divalent aliphatic hydrocarbon group for $Va^1$ in formula (a1-1), and an adamantyl group or a norbornyl group is preferable.

In addition, the cyclic hydrocarbon group for $R^{101}$ may include a hetero atom such as a heterocyclic ring, and specific examples thereof include each lactone-containing cyclic group represented by general formulae (a2-r-1) to (a2-r-7), each —$SO_2$-containing cyclic group represented by general formulae (a5-r-1) to (a5-r-4), and additionally heterocyclic groups represented by (r-hr-1) to (r-hr-16) shown below.

[Chemical formula 31]

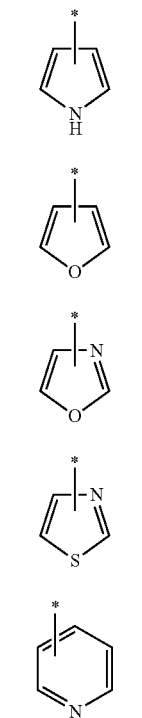

(r-hr-1)

(r-hr-2)

(r-hr-3)

(r-hr-4)

(r-hr-5)

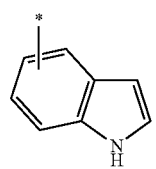

(r-hr-6)

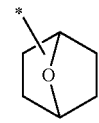

(r-hr-7)

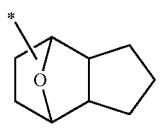

(r-hr-8)

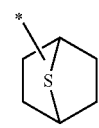

(r-hr-9)

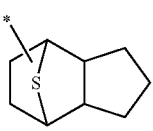

(r-hr-10)

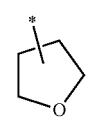

(r-hr-11)

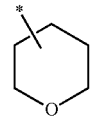

(r-hr-12)

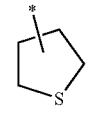

(r-hr-13)

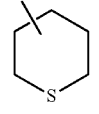

(r-hr-14)

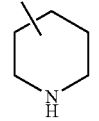

(r-hr-15)

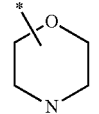

(r-hr-16)

Examples of the substituent in the cyclic hydrocarbon group for $R^{101}$ include an alkyl group, an alkoxy group, a halogen atom, a halogenated alkyl group, a hydroxy group, a carbonyl group, and a nitro group.

As an alkyl group for the substituent, an alkyl group having 1 to 5 carbon atoms is preferable, and a methyl group, an ethyl group, a propyl group, an n-butyl group, and a tert-butyl group are most preferable.

As an alkoxy group for the substituent, an alkoxy group having 1 to 5 carbon atoms is preferable, a methoxy group, an ethoxy group, an n-propoxy group, an iso-propoxy group, an n-butoxy group, and a tert-butoxy group are more preferable, and a methoxy group and an ethoxy group are most preferable.

As a halogen atom for the substituent, examples thereof include a fluorine atom, a chlorine atom, a bromine atom, and an iodine atom, and a fluorine atom is preferable.

As a halogenated alkyl group for the substituent, examples thereof include a group in which a part or all of the hydrogen atoms of the alkyl group having 1 to 5 carbon atoms, such as a methyl group, an ethyl group, a propyl group, an n-butyl group, and a tert-butyl group, are substituted with a halogen atom.

Chain-like Alkyl Group which may have a Substituent for $R^{101}$

The chain-like alkyl group for $R^{101}$ may be linear or branched.

The linear alkyl group preferably has 1 to 20 carbon atoms, more preferably 1 to 15 carbon atoms, and most preferably 1 to 10 carbon atoms. Specific examples thereof include a methyl group, an ethyl group, a propyl group, a butyl group, a pentyl group, a hexyl group, a heptyl group, an octyl group, a nonyl group, a decyl group, a undecyl group, a dodecyl group, a tridecyl group, a isotridecyl group, a tetradecyl group, a pentadecyl group, a hexadecyl group, an isohexadecyl group, a heptadecyl group, an octadecyl group, a nonadecyl group, an icosyl group, a henicosyl group, and a docosyl group.

The branched alkyl group preferably has 3 to 20 carbon atoms, more preferably 3 to 15 carbon atoms, and most preferably 3 to 10 carbon atoms. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain-like Alkenyl Group which may have a Substituent for $R^{101}$

The chain-like alkenyl group for $R^{101}$ may be linear or branched, preferably has 2 to 10 carbon atoms, more preferably 2 to 5 carbon atoms, still more preferably 2 to 4 carbon atoms, and particularly preferably 3 carbon atoms. Examples of the linear alkenyl group include a vinyl group, a propenyl group (allyl group), and a butynyl group. Examples of the branched alkenyl group include a 1-methylpropenyl group and a 2-methylpropenyl group.

As the chain-like alkenyl group, among the above, a propenyl group is particularly preferable.

As a substituent of the chain-like alkyl group or the alkenyl group for $R^{101}$, examples thereof include an alkoxy group, a halogen atom, a halogenated alkyl group, a hydroxy group, a carbonyl group, a nitro group, an amino group, and a cyclic group for $R^{101}$.

Among the above, $R^{101}$ is preferably a cyclic group which may have a substituent, and more preferably a cyclic hydrocarbon group which may have a substituent. As specific examples, a phenyl group, a naphthyl group, a group in which at least one hydrogen atom is removed from polycycloalkane, each lactone-containing cyclic group represented by formulae (a2-r-1) to (a2-r-7), and each —SO$_2$-containing cyclic group represented by general formulae (a5-r-1) to (a5-r-4) is preferable.

In formula (b-1), $Y^{101}$ represents a divalent linking group including a single bond or an oxygen atom.

In the case where $Y^{101}$ is a divalent linking group including an oxygen atom, the $Y^{101}$ may contain an atom other than the oxygen atom. Examples of the atom other than the oxygen atom include a carbon atom, a hydrogen atom, a sulfur atom, and a nitrogen atom.

Examples of the divalent linking group including the oxygen atom include nonhydrocarbon-based oxygen atom-containing linking groups such as an oxygen atom (ether bond: —O—), an ester bond (—C(=O)—O—), an oxycarbonyl group (—O—C(=O)—), an amide bond (—C(=O)—NH—), a carbonyl group (—C(=O)—), and a carbonate bond (—O—C(=O)—O—); and combinations of the nonhydrocarbon-based oxygen atom-containing linking groups with an alkylene group. Further, a sulfonyl group (—SO$_2$—) may be linked to the combinations. Examples of the combinations include each linking group represented by formulae (y-al-1) to (y-al-7) shown below.

[Chemical formula 32]

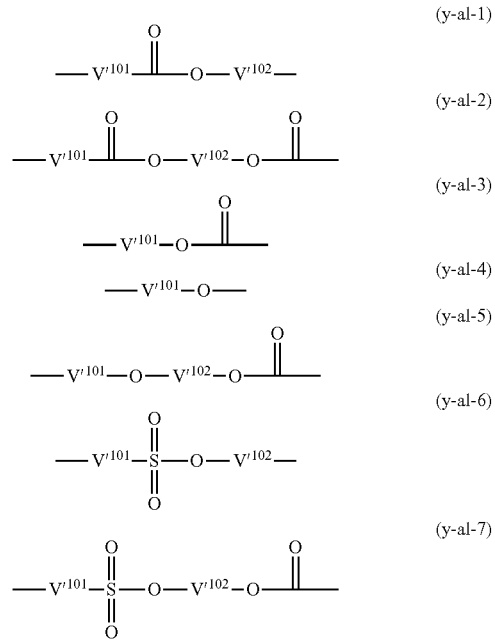

In the formulae, $V'^{101}$ represents a single bond or an alkylene group having 1 to 5 carbon atoms; and $V'^{102}$ represents a divalent saturated hydrocarbon group having 1 to 30 carbon atoms.

The divalent saturated hydrocarbon group for V'102 is preferably an alkylene group having 1 to 30 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—CH$_2$—]; an alkylmethylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an ethylene group [—CH$_2$CH$_2$—]; an alkylethylene group such as —CH(CH$_3$)CH$_2$—, —CH(CH$_3$)CH(CH$_3$)—, —C(CH$_3$)$_2$CH$_2$—, and —CH(CH$_2$CH$_3$)CH$_2$—; a trimethylene group (n-propylene group) [—CH$_2$CH$_2$CH$_2$—]; an alkyltrimethylene group such as —CH(CH$_3$)CH$_2$CH$_2$— and —CH$_2$CH(CH$_3$)CH$_2$—; a tetramethylene group [—CH$_2$CH$_2$CH$_2$CH$_2$—]; an alkyltetramethylene group such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

In addition, a part of the methylene group in the alkylene group for $V'^{101}$ or $V'^{102}$ may be substituted with a divalent aliphatic cyclic group having 5 to 10 carbon atoms. As the aliphatic cyclic group, a divalent group in which one hydrogen atom is removed from a cyclic aliphatic hydrocarbon group for $Ra^{t3}$ in formula (a1-r-1) is preferable, and a cyclohexylene group, a 1,5-adamantylene group, and a 2,6-adamantylene group are more preferable.

$Y^{101}$ is preferably a divalent linking group including an ester bond or ether bond, and each linking group represented by formulae (y-al-1) to (y-al-5) is preferable.

In formula (b-1), $V^{101}$ represents a single bond, an alkylene group, or a fluorinated alkylene group. The alkylene group or a fluorinated alkylene group for $V^{101}$ preferably has 1 to 4 carbon atoms. Examples of the fluorinated alkylene group for $V^{101}$ include groups in which a part or all of the hydrogen atoms of the alkylene group for $V^{101}$ are substituted with a fluorine atom. Among these, $V^{101}$ is preferably a single bond or a fluorinated alkylene group having 1 to 4 carbon atoms.

In formula (b-1), $R^{102}$ represents a fluorine atom or a fluorinated alkyl group having 1 to 5 carbon atoms. $R^{102}$ is preferably a fluorine atom or a perfluoroalkyl group having 1 to 5 carbon atoms, and more preferably a fluorine atom.

Specific examples of the anion moiety of the component (b-1) include a fluorinated alkyl sulfonate anion such as a trifluoromethane sulfonate anion and perfluorobutane sulfonate anion, in the case where $Y^{101}$ is a single bond; and an anion represented by any one of formulae (an-1) to (an-3) shown below, in the case where $Y^{101}$ is a divalent linking group including an oxygen atom.

[Chemical formula 33]

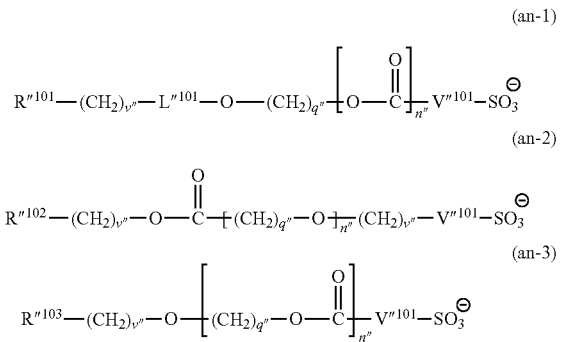

In the formulae, $R''^{101}$ represents an aliphatic cyclic group which may have a substituent, each group represented by formulae (r-hr-1) to (r-hr-6), or a chain-like alkyl group which may have a substituent; $R''^{102}$ represents an aliphatic cyclic group which may have a substituent, each lactone-containing cyclic group represented by formulae (a2-r-1) to (a2-r-7), or each —$SO_2$-containing cyclic group represented by general formulae (a5-r-1) to (a5-r-4); $R''^{103}$ represents an aromatic cyclic group which may have a substituent, an aliphatic cyclic group which may have a substituent, or a chain-like alkenyl group which may have a substituent; $V'''^{101}$ represents a fluorinated alkylene group; $L''^{101}$ represents —C(=O)— or —$SO_2$—; each v" independently is an integer of 0 to 3, each q" independently is an integer of 1 to 20; and n" is 0 or 1.

The aliphatic cyclic group which may have a substituent for $R''^{101}$, $R''^{102}$, and $R''^{103}$ is preferably a group exemplified as the cyclic aliphatic hydrocarbon group for $R^{101}$.

Examples of the substituent include the same substituents with which the cyclic aliphatic hydrocarbon group for $R^{101}$ may be substituted.

The aromatic cyclic group which may have a substituent for $R'''^{103}$ is preferably a group exemplified as the aromatic hydrocarbon group in the cyclic hydrocarbon group for $R^{101}$. Examples of the substituent include the same substituents with which the aromatic hydrocarbon group for $R^{101}$ may be substituted.

The chain-like alkyl group which may have a substituent for $R''^{101}$ is preferably a group exemplified as the chain-like alkyl group for $R^{101}$. The chain-like alkenyl group which may have a substituent for $R''^{103}$ is preferably a group exemplified as the chain-like alkenyl group for $R^{101}$. $V'''^{101}$ is preferably a fluorinated alkylene group having 1 to 3 carbon atoms, and particularly preferably —$CF_2$—, —$CF_2CF_2$—, —$CHFCF_2$—, —$CF(CF_3)CF_2$—, or —$CH(CF_3)CF_2$—.

Anion Moiety of Component (b-2)

In formula (b-2), $R^{104}$ and $R^{105}$ each independently represent a cyclic group which may have a substituent, a chain-like alkyl group which may have a substituent, or a chain-like alkenyl group which may have a substituent, and respective examples thereof include the same groups as those exemplified for $R^{101}$ in formula (b-1). However, $R^{104}$ and $R^{105}$ may be bonded to each other to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. As the carbon number of the chain-like alkyl group for $R^{104}$ and $R^{105}$ is smaller within the aforementioned range of the carbon number, it is more preferable because solubility in a resist solvent is excellent. In addition, as the number of carbon atoms substituted with a fluorine atom in the chain-like alkyl group for $R^{104}$ and $R^{105}$ is greater, it is more preferable, because the acid strength becomes greater and transparency is improved with respect to high energy light equal to or lower than 200 nm or electron beams. The ratio of the fluorine atom in the chain-like alkyl group, that is, a fluorination rate, is preferably 70% to 100%, more preferably 90% to 100%, and most preferably a perfluoroalkyl group in which all of the hydrogen atoms are substituted with a fluorine atom.

In formula (b-2), $V^{102}$ and $V^{103}$ each independently represent a single bond, an alkylene group, or a fluorinated alkylene group, and respective examples thereof include the same groups as those exemplified for $V^{101}$ in formula (b-1).

In formula (b-2), $L^{101}$ to $L^{102}$ each independently represent a single bond or an oxygen atom.

Anion Moiety of Component (b-3)

In formula (b-3), $R^{106}$ to $R^{108}$ each independently represent acyclic group which may have a substituent, a chain-like alkyl group which may have a substituent, or a chain-like alkenyl group which may have a substituent, and respective examples thereof include the same groups as those exemplified for $R^{101}$ in formula (b-1).

$L^{103}$ to $L^{105}$ each independently represent a single bond, —CO— or —$SO_2$—.

Cation Moiety

In formulae (b-1), (b-2), and (b-3), $M'^{m+}$ represents an organic cation having a valency of m, among these, a sulfonium cation or iodonium cation is preferable, and each cation represented by general formulae (ca-1) to (ca-4) shown below is particularly preferable.

[Chemical formula 34]

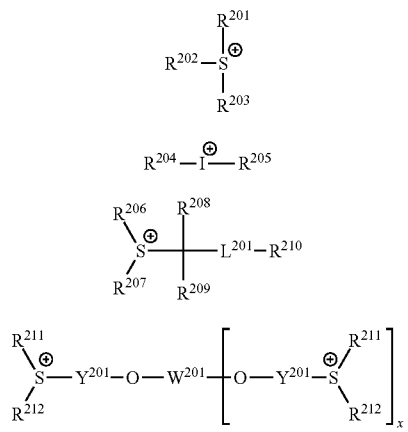

(ca-1)
(ca-2)
(ca-3)
(ca-4)

In the formulae, $R^{201}$ to $R^{207}$, and $R^{211}$ to $R^{212}$ each independently represent an aryl group which may have a substituent, an alkyl group, or an alkenyl group; and $R^{201}$ to $R^{203}$, $R^{206}$ to $R^{207}$, and $R^{211}$ to $R^{212}$ may be bonded to each other to form a ring with a sulfur atom in the formula. $R^{208}$ to $R^{209}$ each independently represent a hydrogen atom or an alkyl group having 1 to 5 carbon atoms; $R^{210}$ represents an aryl group which may have a substituent, an alkyl group, an alkenyl group, or a —$SO_2$-containing cyclic group; $L^{201}$ represents —C(=O)— or —C(=O)—O—; each $Y^{201}$ independently represents an arylene group, an alkylene group, or an alkenylene group; x is 1 or 2; and $W^{201}$ represents a linking group having a valency of (x+1).

Examples of the aryl group for $R^{201}$ to $R^{207}$ and $R^{211}$ to $R^{212}$ include unsubstituted aryl groups having 6 to 20 carbon atoms, and a phenyl group or a naphthyl group is preferable.

The alkyl group for $R^{201}$ to $R^{207}$ and $R^{211}$ to $R^{212}$ may be a chain-like or cyclic alkyl group, and preferably has 1 to 30 carbon atoms.

The alkenyl group for $R^{201}$ to $R^{207}$ and $R^{211}$ to $R^{212}$ preferably has 2 to 10 carbon atoms.

Examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, an arylthio group, and each group represented by formulae (ca-r-1) to (ca-r-7) shown below.

Examples of the aryl group in the arylthio group as the substituent include the same groups as those exemplified for $R^{101}$, and specifically, a phenylthio group or a biphenylthio group can be exemplified.

[Chemical formula 35]

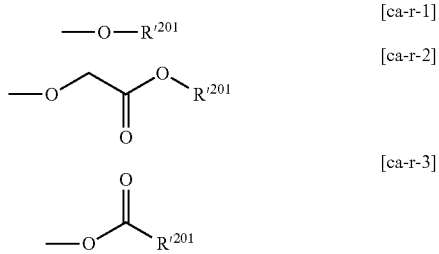

[ca-r-1]
[ca-r-2]
[ca-r-3]

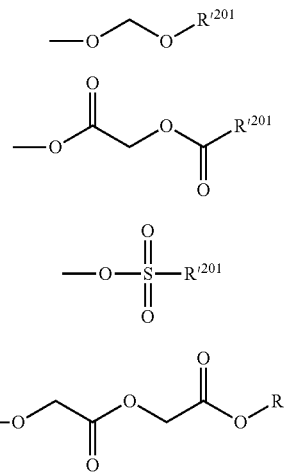

[ca-r-4]
[ca-r-5]
[ca-r-6]
[ca-r-7]

In the formulae, each $R'^{201}$ independently represents a hydrogen atom, a cyclic group which may have a substituent, a chain-like alkyl group, or a chain-like alkenyl group.

Examples of the cyclic group which may have a substituent, a chain-like alkyl group which may have a substituent, or a chain-like alkenyl group which may have a substituent for $R'^{201}$ include the same groups as those exemplified for $R^{101}$ in formula (b-1), and additionally, examples of the cyclic group which may have a substituent or the chain-like alkyl group which may have a substituent include the same group as the acid dissociable group represented by formula (a1-r-2).

In the case where $R^{201}$ to $R^{203}$, $R^{206}$ to $R^{207}$, and $R^{211}$ to $R^{212}$ are bonded to each other to form a ring with a sulfur atom in the formula, they may be bonded to each other via a hetero atom such as a sulfur atom, an oxygen atom, and a nitrogen atom, or a functional group such as a carbonyl group, —SO—, —$SO_2$—, —$SO_3$—, —COO—, —CONH— and —N($R_N$)— ($R_N$ represents an alkyl group having 1 to 5 carbon atoms). As the ring to be formed, one ring including a sulfur atom in the formula in its ring skeleton is preferably a 3- to 10-membered ring and particularly preferably 5- to 7-membered ring, including a sulfur atom. Specific examples of the ring to be formed include a thiophene ring, a thiazole ring, a benzothiophene ring, a thianthrene ring, a benzothiophene ring, a dibenzothiophene ring, a 9H-thioxanthene ring, a thioxanthone ring, a thianthrene ring, a phenoxanthine ring, a tetrahydrothiophenium ring, and a tetrahydrothiopyranium ring.

$R^{208}$ to $R^{209}$ each independently represent a hydrogen atom or an alkyl group having 1 to 5 carbon atoms, and a hydrogen atom or an alkyl group having 1 to 3 carbon atoms is preferable, and $R^{208}$ to $R^{209}$ may be bonded to each other to form a ring in the case where $R^{208}$ to $R^{209}$ represent an alkyl group.

$R^{210}$ represents an aryl group which may have a substituent, an alkyl group which may have a substituent, an alkenyl group which may have a substituent, or a —$SO_2$-containing cyclic group which may have a substituent.

Examples of the aryl group for $R^{210}$ include unsubstituted aryl groups having 6 to 20 carbon atoms, and a phenyl group or a naphthyl group is preferable.

The alkyl group for $R^{210}$ may be a chain-like or cyclic alkyl group, and preferably has 1 to 30 carbon atoms.

The alkenyl group for $R^{210}$ preferably has 2 to 10 carbon atoms.

Examples of the —SO$_2$-containing cyclic group which may have a substituent for R$^{210}$ include the same "—SO$_2$-containing cyclic group" as that exemplified for Ra$^{21}$ in general formula (a2-1), and a group represented by general formula (a5-r-1) is preferable.

Each Y$^{201}$ independently represents an arylene group, an alkylene group or an alkenylene group.

Examples of the arylene group for Y$^{201}$ include a group in which one hydrogen atom is removed from the aryl group exemplified as the aromatic hydrocarbon group for R$^{101}$ in formula (b-1).

Examples of the alkylene group and alkenylene group for Y$^{201}$ include the same group as the aliphatic hydrocarbon group as the divalent hydrocarbon group for Va$^1$ in general formula (a1-1).

In formula (ca-4), x is 1 or 2.

W$^{201}$ represents a linking group having a valency of (x+1), that is divalent or trivalent.

As the divalent linking group for W$^{201}$, a divalent hydrocarbon group which may have a substituent is preferable, and the same hydrocarbon group for Ya$^{21}$ in general formula (a2-1) can be exemplified. The divalent linking group for W$^{201}$ may be linear, branched, or cyclic, and is preferably cyclic. Among these, a group in which two carbonyl groups are combined to the both terminals of an arylene group is preferable. Examples of the arylene group include a phenylene group and a naphtylene group, and a phenylene group is particularly preferable.

Examples of the trivalent linking group for W$^{201}$ include a group in which one hydrogen atom is removed from the divalent linking group for the W$^{201}$ and a group in which the divalent linking group is further bonded to the divalent linking group. As the trivalent linking group for W$^{201}$, a group in which two carbonyl groups are bonded to an arylene group is preferable.

Preferred specific examples of cation represented by formula (ca-1) include each cation represented by formulae (ca-1-1) to (ca-1-63) shown below.

[Chemical formula 36]

(ca-1-1)

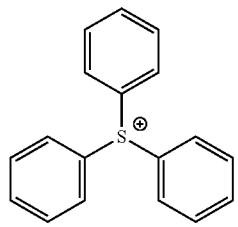

(ca-1-2)

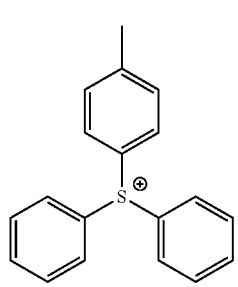

(ca-1-3)

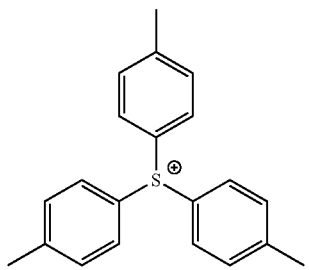

(ca-1-4)

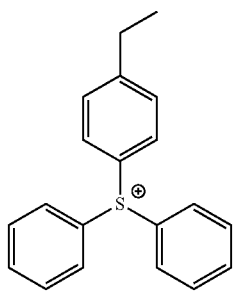

(ca-1-5)

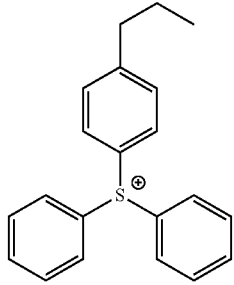

(ca-1-6)

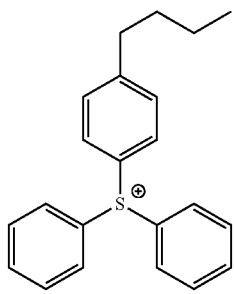

(ca-1-7)

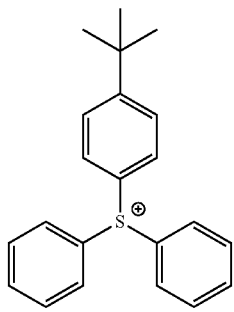

(ca-1-8)
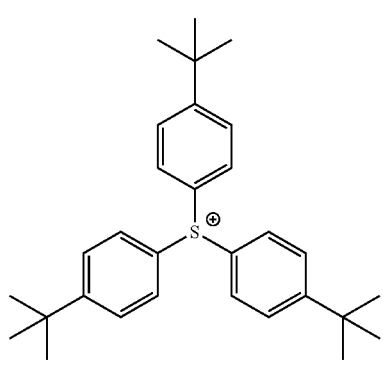
(ca-1-9)
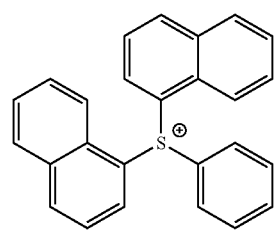
(ca-1-10)
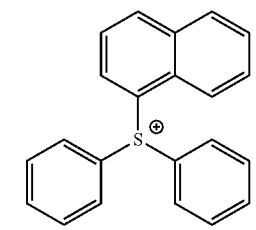
(ca-1-11)
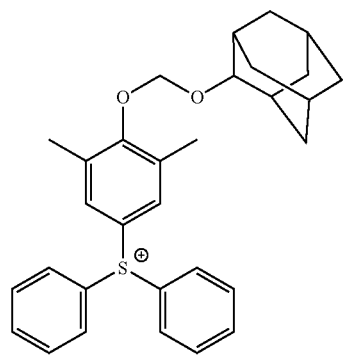
(ca-1-12)
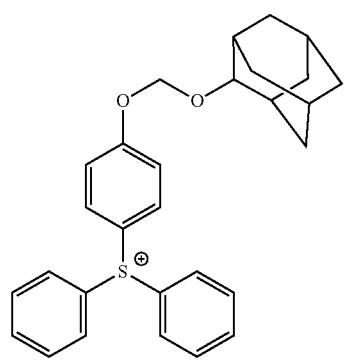
(ca-1-13)
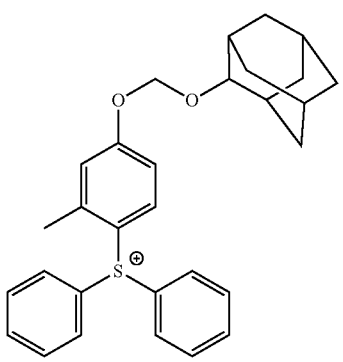
(ca-1-14)
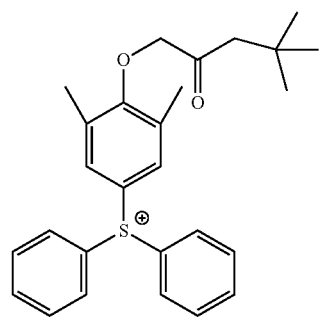
(ca-1-15)
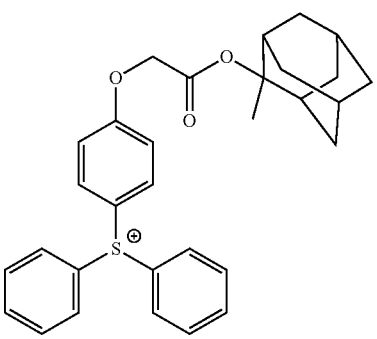
(ca-1-16)
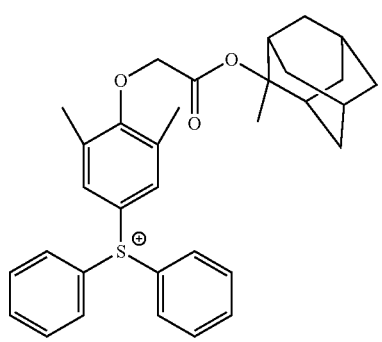

[Chemical formula 37]
(ca-1-17)
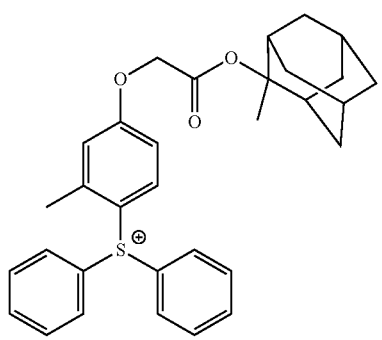
(ca-1-18)
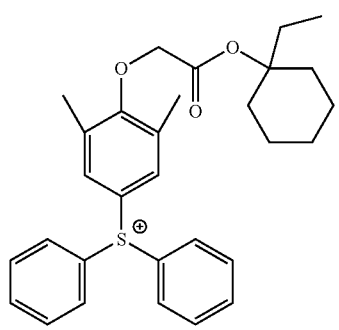
(ca-1-19)
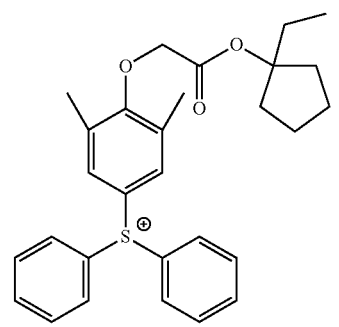
(ca-1-20)
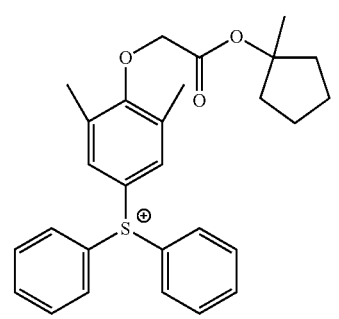
(ca-1-21)
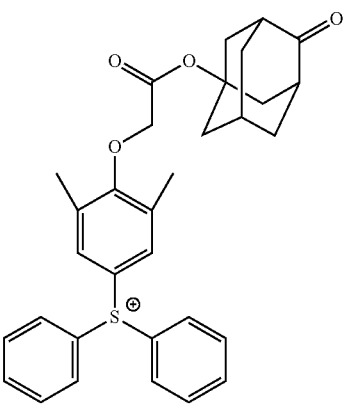
(ca-1-22)
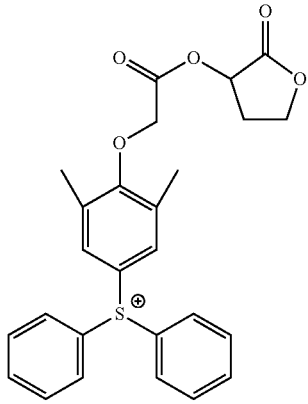
(ca-1-23)
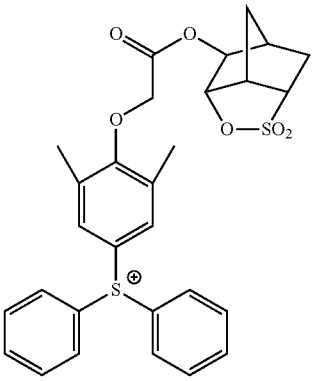
(ca-1-24)
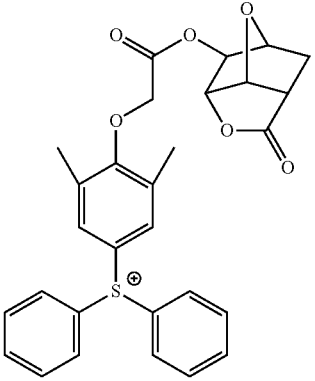

(ca-1-25) 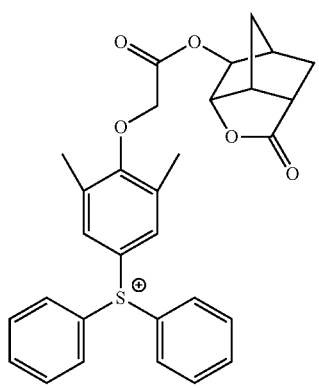
(ca-1-26) 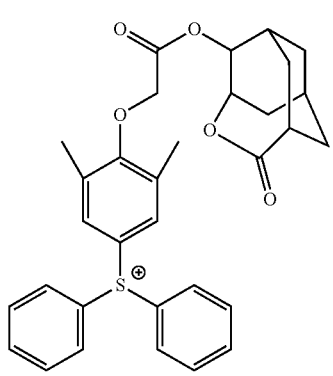
(ca-1-27) 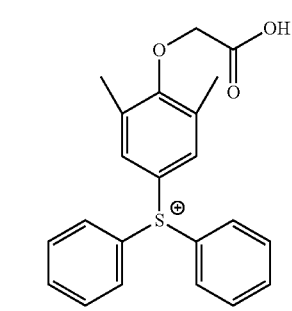
(ca-1-28) 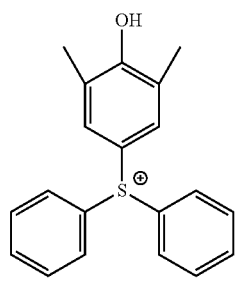
(ca-1-29) 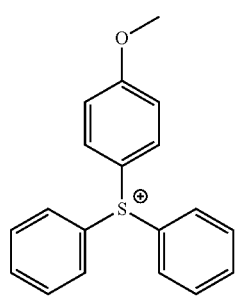
(ca-1-30) 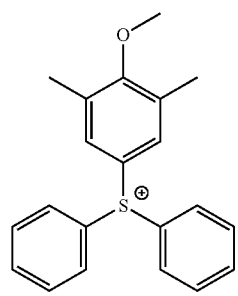
(ca-1-31) 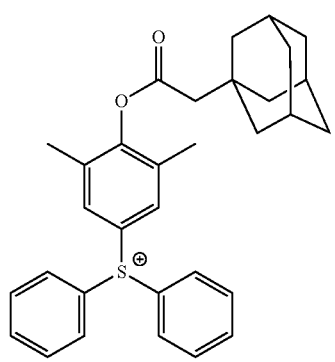
(ca-1-32) 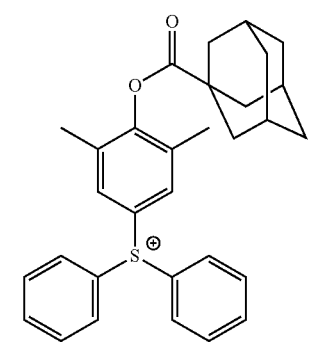
(ca-1-33) 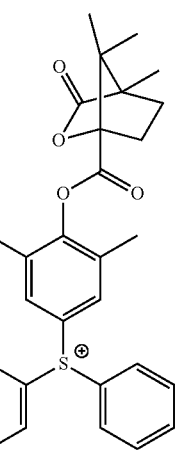

[Chemical formula 38]
(ca-1-34)
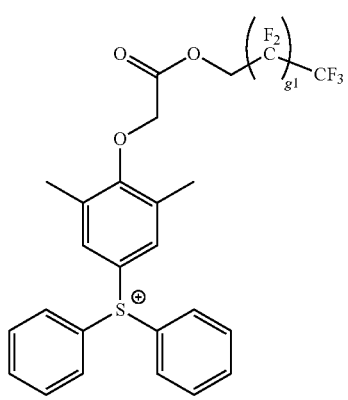
(ca-1-35)
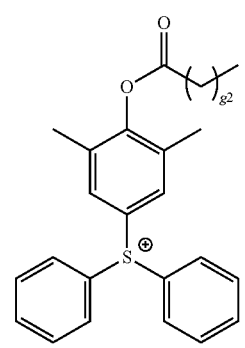
(ca-1-36)
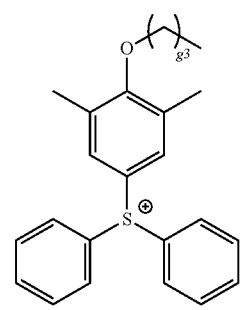
(ca-1-37)
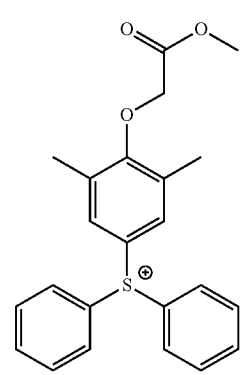
(ca-1-38)
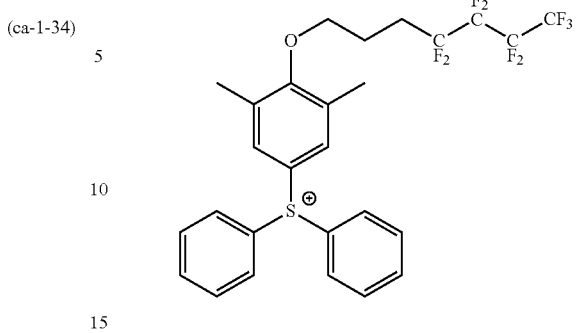
(ca-1-39)
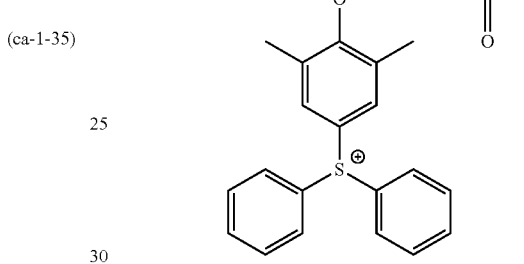
(ca-1-40)
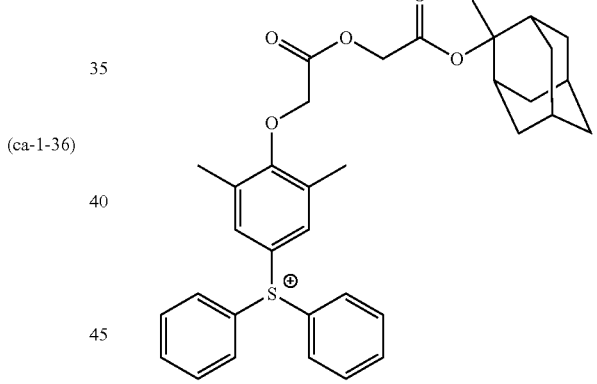
(ca-1-41)
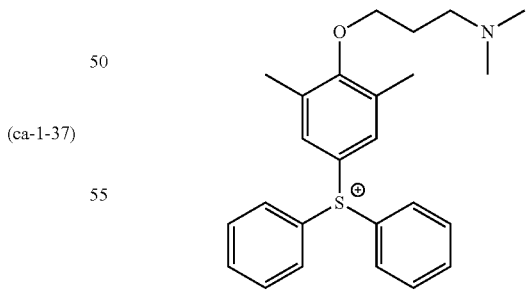
(ca-1-42)
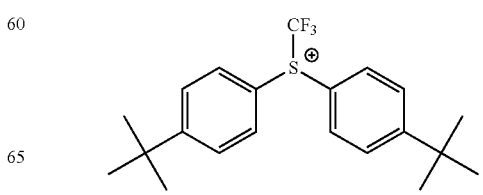

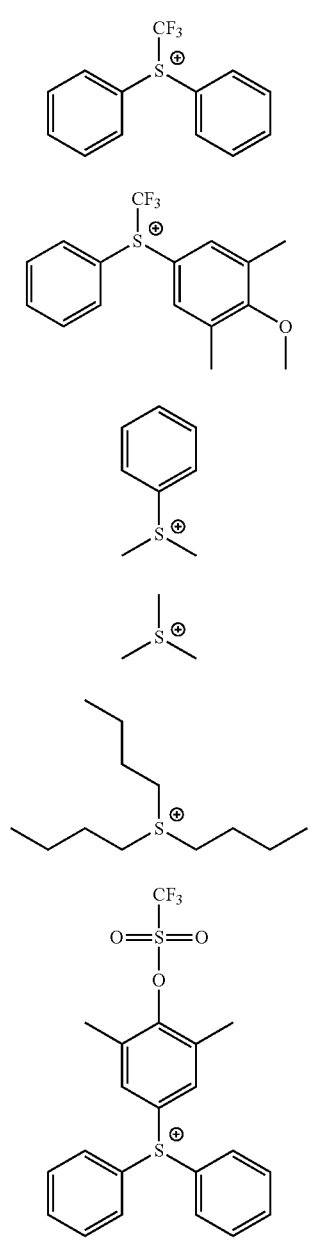
(ca-1-43)
(ca-1-44)
(ca-1-45)
(ca-1-46)
(ca-1-47)
(ca-1-48)
In the formulae, g1, g2, and g3 represent a repeating number; g1 is an integer of 1 to 5; g2 is an integer of 0 to 20; and g3 is an integer of 0 to 20.
[Chemical formula 39]
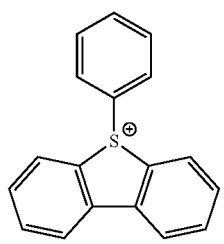
(ca-1-49)
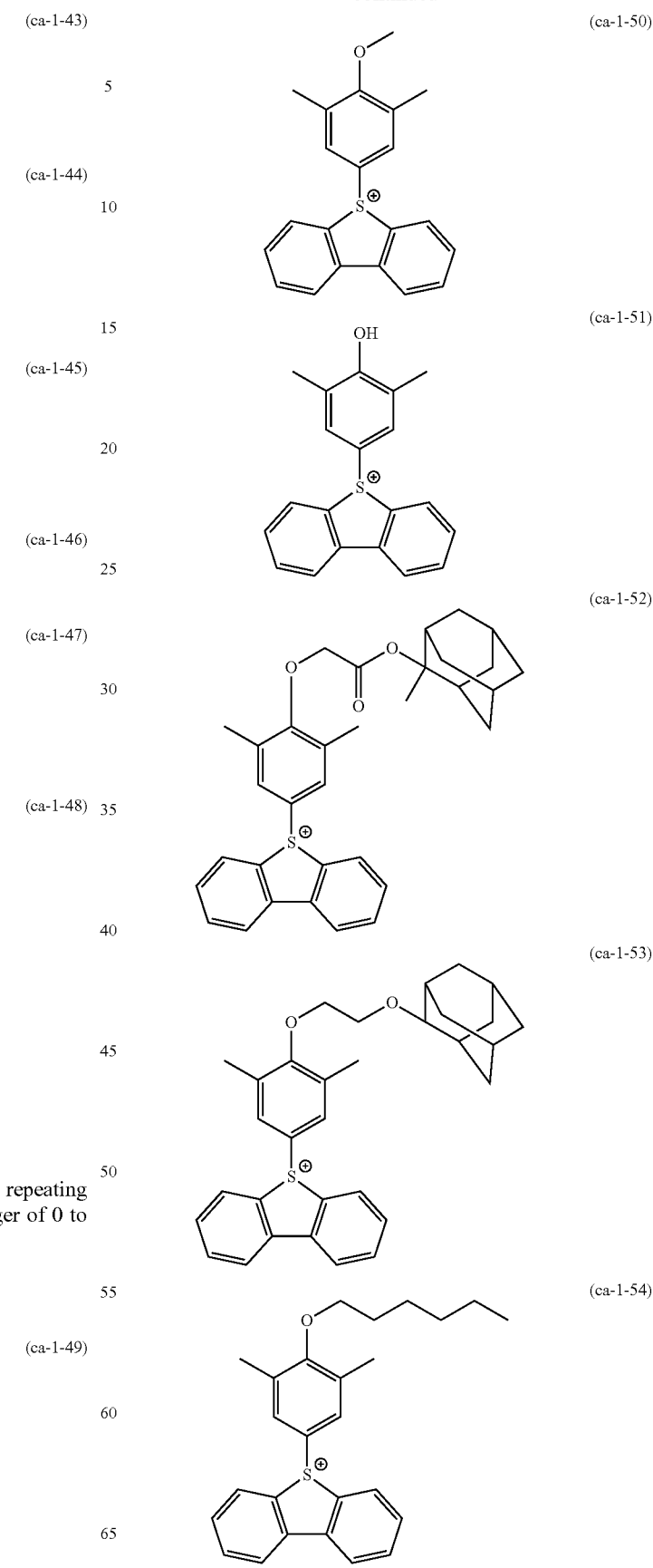
(ca-1-50)
(ca-1-51)
(ca-1-52)
(ca-1-53)
(ca-1-54)

(ca-1-55) 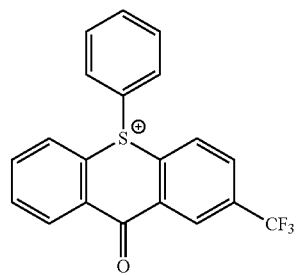
(ca-1-56) 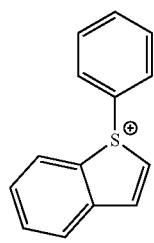
(ca-1-57) 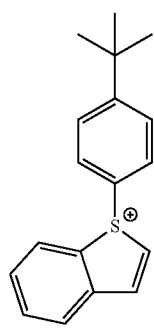
(ca-1-58) 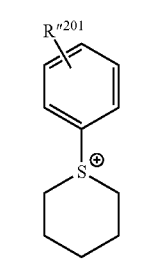
(ca-1-59) 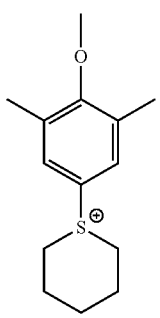
(ca-1-60) 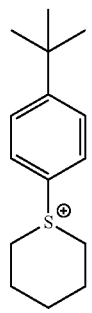
(ca-1-61) 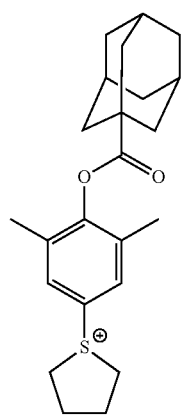
(ca-1-62) 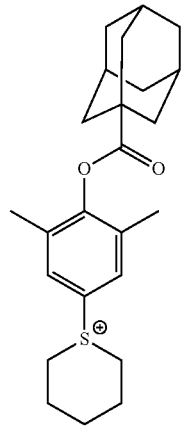
(ca-1-63) 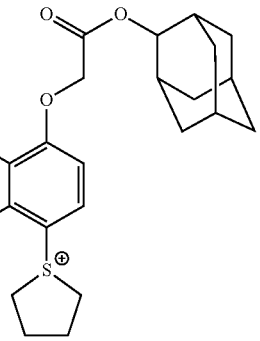
In the formulae, $R''^{201}$ represents a hydrogen atom or a substituent; and examples of the substituent include the same substituents as those which $R^{201}$ to $R^{207}$ and $R^{210}$ to $R^{212}$ may have.

Preferred specific examples of the cation represented by formula (ca-3) include each cation represented by formulae (ca-3-1) to (ca-3-6) shown below.

[Chemical formula 40]

(ca-3-1)
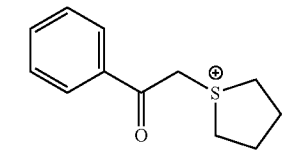

(ca-3-2)
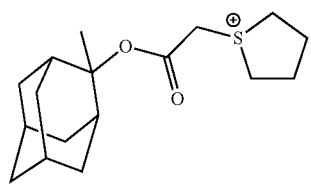

(ca-3-3)
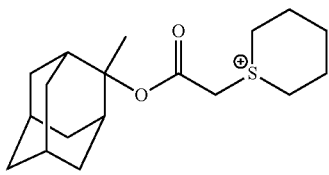

(ca-3-4)
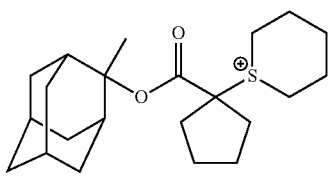

(ca-3-5)
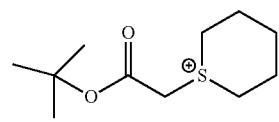

(ca-3-6)
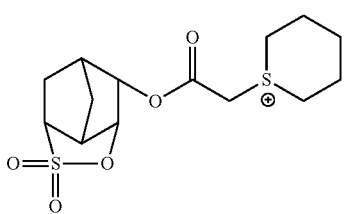

Preferred specific examples of the cation represented by formula (ca-4) include each cation represented by formulae (ca-4-1) to (ca-4-2) shown below.

[Chemical formula 41]

(ca-4-1)
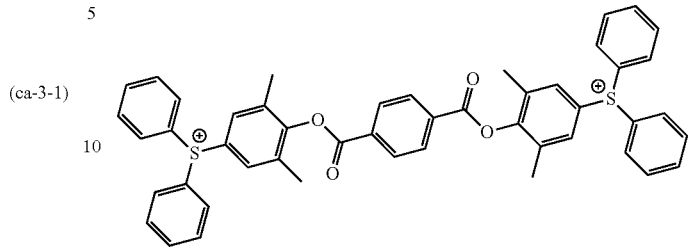

(ca-4-2)
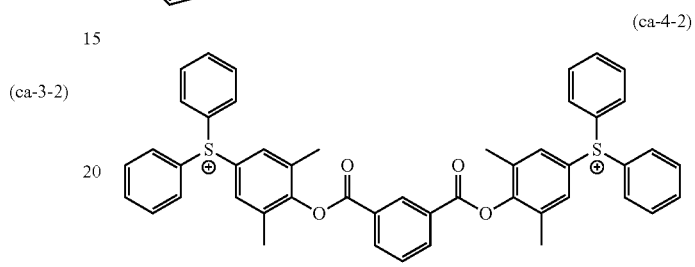

As the component (B), one type of the aforementioned acid generator may be used alone, or two or more types thereof may be used in combination.

In the present invention, in the case where the resist composition contains a component (B), the content of the component (B) is preferably 0.5 parts by mass to 60 parts by mass, more preferably 1 part by mass to 50 parts by mass, and still more preferably 1 part by mass to 40 parts by mass with respect to 100 parts by mass of the component (A). If the content of the component (B) is set to the aforementioned range, a pattern is sufficiently formed. Also, when respective components of the resist composition are dissolved in an organic solvent, a uniform solution is obtained, and storage stability becomes excellent, which is preferable.

Photo-reactive Quencher; Component (D0)

The resist composition of the present invention contains a photo-reactive quencher (D0) (hereinafter, may be referred to as "component (D0)").

A "quencher" is an acid diffusion control agent, in other words, an agent which traps an acid generated from the component (B) upon exposure.

The "photo-reactive quencher" acts as a quencher which traps an acid before exposure (or at the unexposed portion), and is decomposed upon exposure, thereby losing a function as a quencher after exposure (or at the exposed portion).

The resist composition of the present invention contains at least compound (D0-1) represented by general formula (d0) shown below as a component (D0). According to this, a resist pattern formed by using the resist composition of the present invention has excellent lithography properties, and additionally, the quality stability of the resist composition can be improved.

[Chemical formula 42]

(d0)
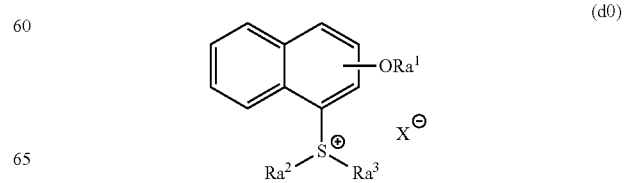

In the formula, $Ra^1$ represents an alkyl group having 1 to 10 carbon atoms which may have a substituent; and $Ra^2$ and $Ra^3$ each independently represent an alkyl group having 1 to 10 carbon atoms which may have a substituent. $X^-$ represents a counter anion.

In formula (d0), $Ra^1$ to $Ra^3$ each independently represent an alkyl group having 1 to 10 carbon atoms which may have a substituent.

The alkyl group having 1 to 10 carbon atoms for $Ra^1$ to $Ra^3$ may be linear or branched, and specific examples of the linear alkyl group include a methyl group, an ethyl group, a propyl group, an n-butyl group, a pentyl group, a hexyl group, an octyl group, a nonyl group, and a decyl group.

Examples of the branched alkyl group include an isopropyl group, an isobutyl group, a tert-butyl group, an isopentyl group, a neopentyl group, a 1,1-dimethylethyl group, a 1,1-diethylpropyl group, a 2,2-dimethylpropyl group, and a 2,2,-dimethylbutyl group.

In formula (d0), $Ra^1$ to $Ra^3$ are preferably a linear alkyl group.

Examples of the substituent which $Ra^1$ to $Ra^3$ may have include an alkyl group, an alkoxy group, a hydroxy group, and a carbonyl group.

As the alkyl group for the substituent, an alkyl group having 1 to 5 carbon atoms can be exemplified, and preferred examples thereof include a methyl group, an ethyl group, a propyl group, an n-butyl group, and a tert-butyl group.

As the alkoxy group for the substituent, an alkoxy group having 1 to 5 carbon atoms can be exemplified, and a methoxy group, an ethoxy group, an n-propoxy group, an iso-propoxy group, an n-butoxy group, or a tert-butoxy group is preferable, and a methoxy group or an ethoxy group is more preferable.

A part of carbon atom constituting $Ra^1$ to $Ra^3$ may be substituted with a substituent including a hetero atom. As the substituent including the hetero atom, —O—, —C(=O)—O—, —S—, —S(=O)$_2$—, or —S(=O)$_2$—O— is preferable.

In the present invention, $Ra^1$ to $Ra^3$ may have a substituent or may have not, but no substitution is preferable.

Hereinafter, specific examples of the cation moiety of formula (d0) will be described.

[Chemical formula 43]

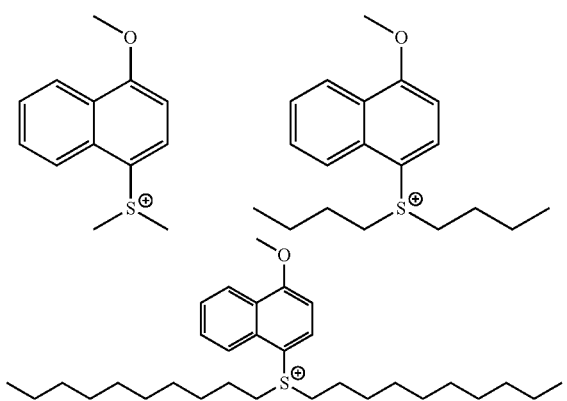

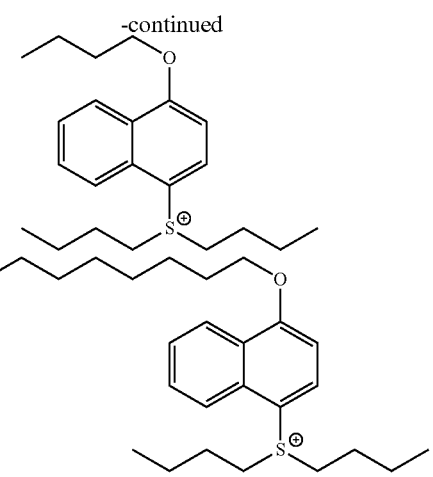

In formula (d0), $X^-$ is a counter anion.

The counter anion represented by $X^-$ is preferably anions represented by any one of general formulae (d1-1) to (d1-3) shown below.

[Chemical formula 44]

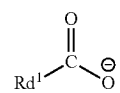
(d1-1)

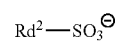
(d1-2)

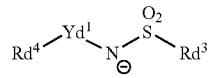
(d1-3)

In formulae (d1-1) to (d1-3), $Rd^1$ to $Rd^4$ represent a cyclic group which may have a substituent, a chain-like alkyl group which may have a substituent, or a chain-like alkenyl group which may have a substituent. However, a fluorine atom bonded to a carbon atom adjacent to a sulfur atom in $Rd^2$ of formula (d1-2) is no more than two. $Yd^1$ represents a single bond or a divalent linking group.

In formula (d1-1), $Rd^1$ represents a cyclic group which may have a substituent, a chain-like alkyl group which may have a substituent, or a chain-like alkenyl group which may have a substituent, and examples thereof include the same groups as those exemplified for $R^{101}$ in general formula (b-1).

Among these, as $Rd^1$, an aromatic hydrocarbon group which may have a substituent, an aliphatic cyclic group which may have a substituent, or a chain-like hydrocarbon group which may have a substituent is preferable. As the substituent which these groups may have, a hydroxy group, a fluorine atom or a fluorinated alkyl group is preferable.

As the aromatic hydrocarbon group, a phenyl group or a naphthyl group is more preferable.

As the aliphatic cyclic group, a group in which at least one hydrogen atom is removed from polycycloalkane such as adamantane, norbornane, isobornane, tricyclodecane and tetracyclododecane, is more preferable.

As the chain-like hydrocarbon group, a chain-like alkyl group is preferable. The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl group, and a decyl group; and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

In the case where the chain-like alkyl group is a fluorinated alkyl group having a fluorine atom or a fluorinated alkyl group as a substituent, the fluorinated alkyl group preferably has 1 to 11 carbon atoms, more preferably 1 to 8 carbon atoms, and still more preferably 1 to 4 carbon atoms, and the fluorinated alkyl group may contain an atom other than the fluorine atom. Examples of the atom other than the fluorine atom include an oxygen atom, a carbon atom, a hydrogen atom, a sulfur atom, and a nitrogen atom.

$Rd^1$ is preferably a fluorinated alkyl group in which a part or all of the hydrogen atoms constituting the linear alkyl group are substituted with a fluorine atom, or a fluorinated alkyl group (linear perfluoroalkyl group) in which all of the hydrogen atoms constituting the linear alkyl group are substituted with a fluorine atom.

Preferred specific examples of the anion moiety represented by the following (d1-1) are shown below.

[Chemical formula 45]

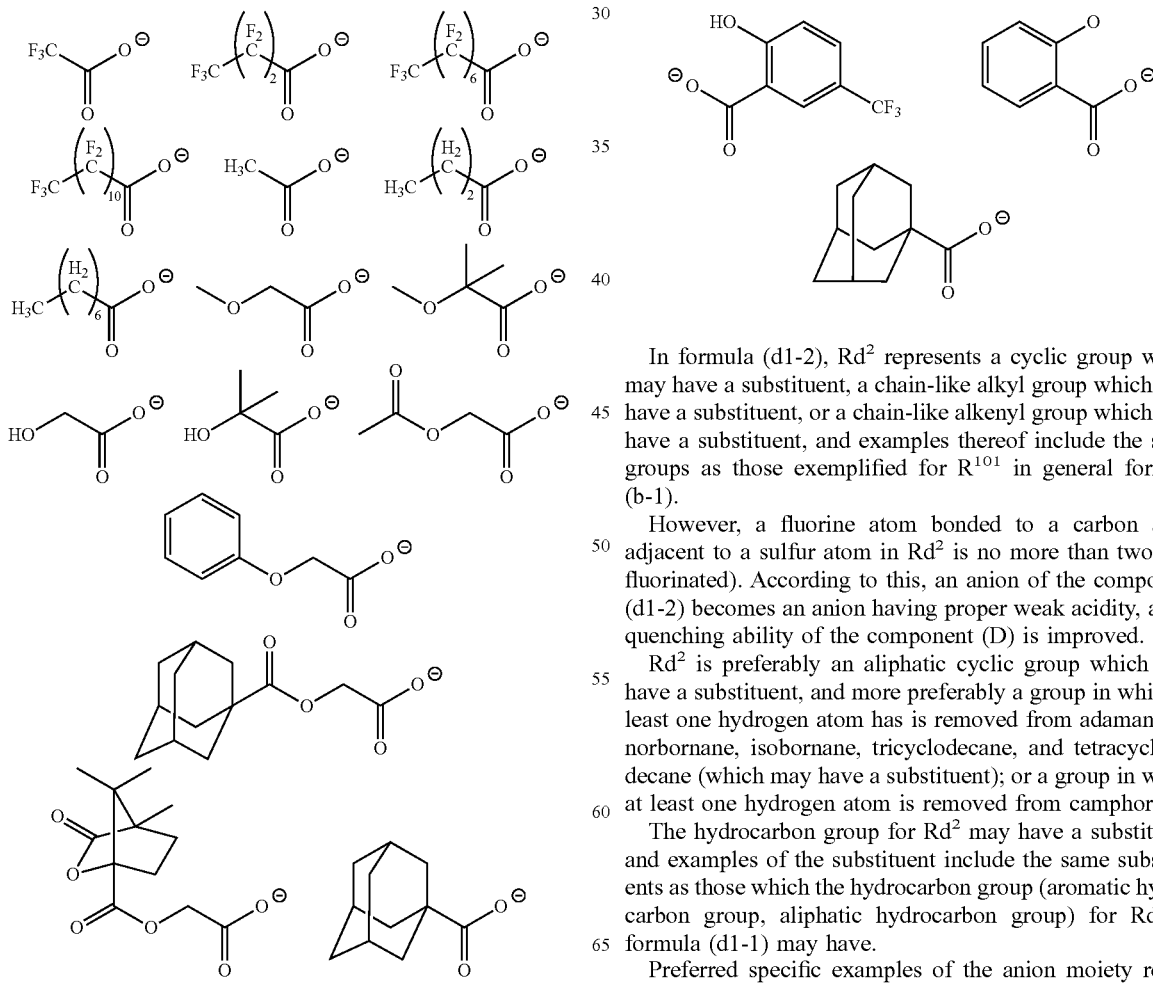

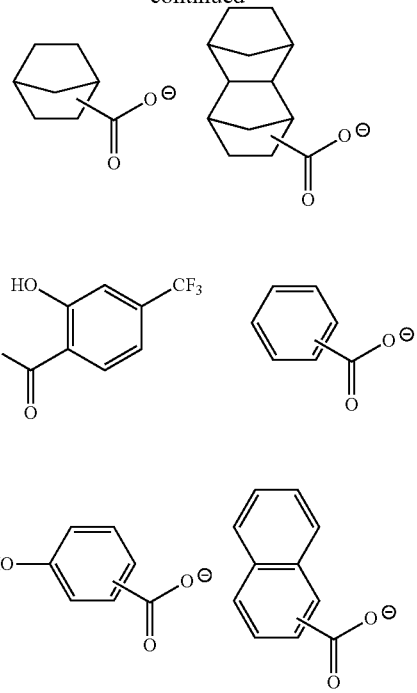

In formula (d1-2), $Rd^2$ represents a cyclic group which may have a substituent, a chain-like alkyl group which may have a substituent, or a chain-like alkenyl group which may have a substituent, and examples thereof include the same groups as those exemplified for $R^{101}$ in general formula (b-1).

However, a fluorine atom bonded to a carbon atom adjacent to a sulfur atom in $Rd^2$ is no more than two (not fluorinated). According to this, an anion of the component (d1-2) becomes an anion having proper weak acidity, and a quenching ability of the component (D) is improved.

$Rd^2$ is preferably an aliphatic cyclic group which may have a substituent, and more preferably a group in which at least one hydrogen atom has is removed from adamantane, norbornane, isobornane, tricyclodecane, and tetracyclododecane (which may have a substituent); or a group in which at least one hydrogen atom is removed from camphor.

The hydrocarbon group for $Rd^2$ may have a substituent, and examples of the substituent include the same substituents as those which the hydrocarbon group (aromatic hydrocarbon group, aliphatic hydrocarbon group) for $Rd^1$ in formula (d1-1) may have.

Preferred specific examples of the anion moiety represented by the following (d1-2) are shown.

[Chemical formula 46]

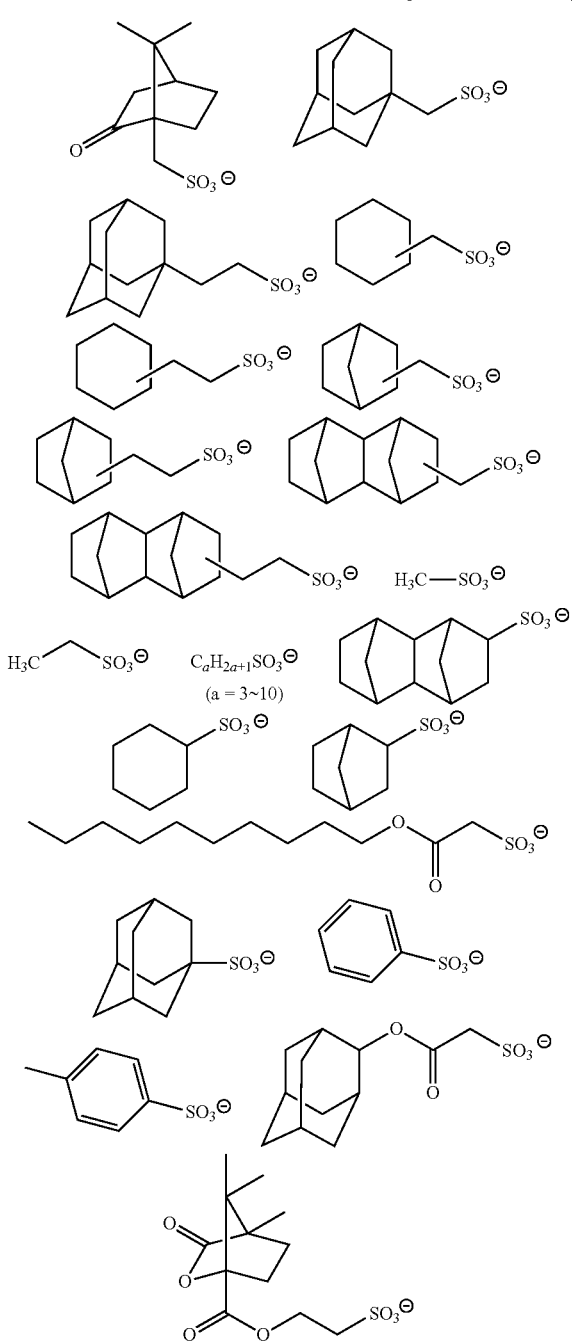

In formula (d1-3), $Rd^3$ represents a cyclic group which may have a substituent, a chain-like alkyl group which may have a substituent, or a chain-like alkenyl group which may have a substituent, examples thereof include the same groups as those exemplified for $R^{101}$, and a cyclic group including a fluorine atom, a chain-like alkyl group, or a chain-like alkenyl group is preferable. Among these, a fluorinated alkyl group is preferable and the fluorinated alkyl group as exemplified for $Rd^1$ is more preferable.

In formula (d1-3), $Rd^4$ represents a cyclic group which may have a substituent, a chain-like alkyl group which may have a substituent, or a chain-like alkenyl group which may have a substituent, and examples thereof include the same groups as exemplified for $R^{101}$.

Among these, an alkyl group which may have a substituent, an alkoxy group, an alkenyl group, or a cyclic group is preferable.

The alkyl group for $Rd^4$ is preferably a linear alkyl group having 1 to 5 carbon atoms or branched alkyl group, and specific examples thereof include a methyl group, an ethyl group, a propyl group, an isopropyl group, an n-butyl group, an isobutyl group, a tert-butyl group, a pentyl group, an isopentyl group, and a neopentyl group. A part of the hydrogen atom of the alkyl group for $Rd^4$ may be substituted with a hydroxy group, a cyano group or the like.

The alkoxy group for $Rd^4$ is preferably an alkoxy group having 1 to 5 carbon atoms, and specific examples of the alkoxy group having 1 to 5 carbon atoms include a methoxy group, an ethoxy group, an n-propoxy group, an iso-propoxy group, an n-butoxy group, and a tert-butoxy group. Among these, a methoxy group or an ethoxy group is preferable.

Examples of the alkenyl group for $Rd^4$ include the same groups as those exemplified for $R^{101}$, and a vinyl group, a propenyl group (allyl group), a 1-methylpropenyl group, or a 2-methylpropenyl group is preferable. These groups may further have an alkyl group having 1 to 5 carbon atoms or a halogenated alkyl group having 1 to 5 carbon atoms as a substituent.

Examples of the cyclic group for $Rd^4$ include the same groups as those exemplified for $R^{101}$, and an alicyclic group in which at least one hydrogen atom is removed from cycloalkane such as cyclopentane, cyclohexane, adamantane, norbornane, isobornane, tricyclodecane, and tetracyclododecane; or an aromatic group such as a phenyl group and a naphthyl group is preferable. In the case where $Rd^4$ is an alicyclic group, the resist composition dissolves in an organic solvent satisfactorily, thereby obtaining the excellent lithography properties. In addition, in the case where $Rd^4$ is an aromatic group, the resist composition has excellent light absorption efficiency, thereby obtaining the excellent sensitivity or lithography properties, in the lithography using EUV as a light source for exposure.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, aromatic hydrocarbon group) which may have a substituent and a divalent linking group including a hetero atom. Examples of these groups respectively include the same groups as those exemplified in the explanation of the divalent linking group for $Ya^{21}$ in formula (a2-1).

$Yd^1$ is preferably a carbonyl group, an ester bond, an amide bond, an alkylene group, or a combination thereof. The alkylene group is more preferably a linear or branched alkylene group, and still more preferably a methylene group or an ethylene group.

Preferred specific examples of the anion moiety represented by the following formula (d1-3) are shown.

[Chemical formula 47]

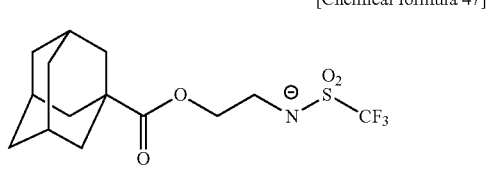

89
-continued
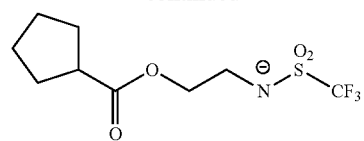
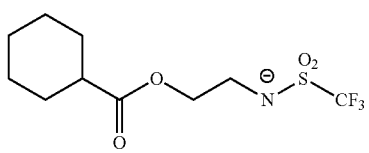
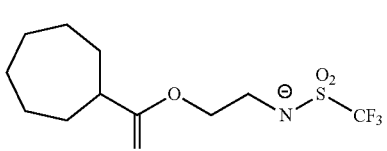
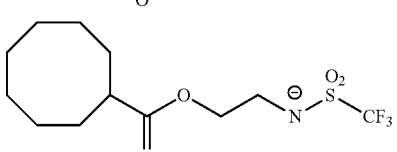
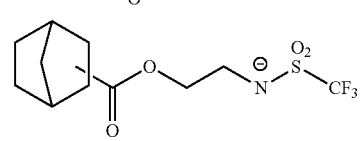
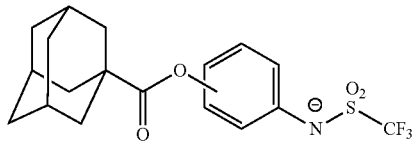
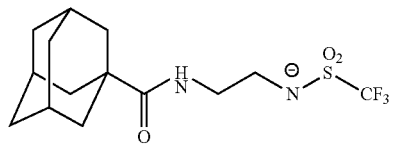
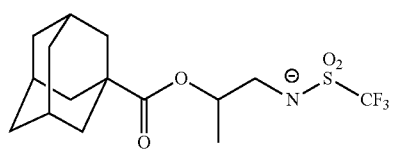
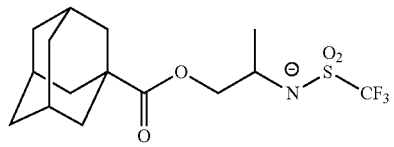
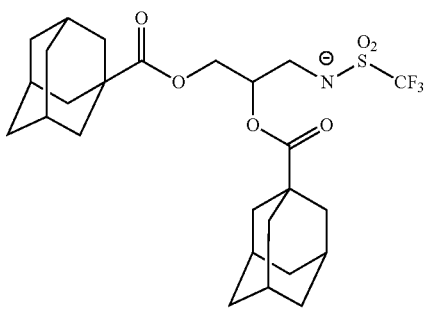
90
-continued
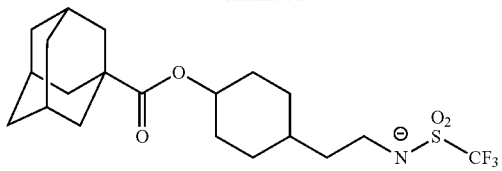
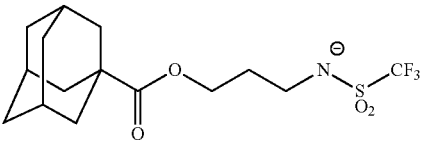
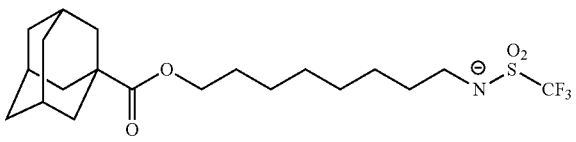
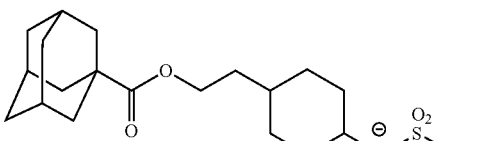
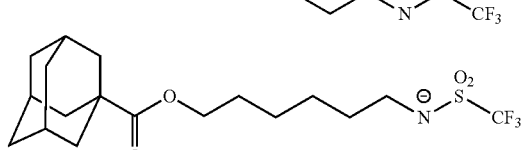
[Chemical formula 48]
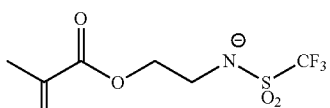
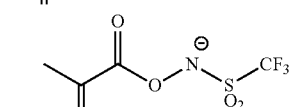
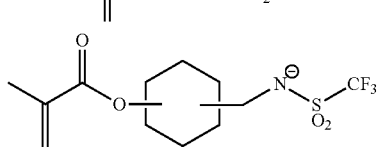
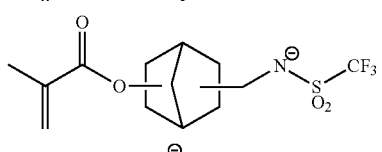
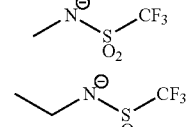
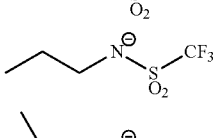
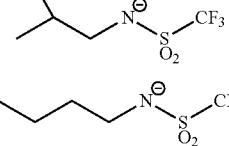

91
-continued
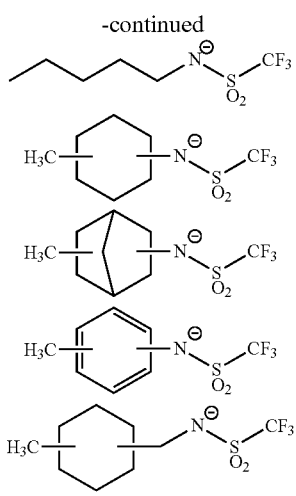
92
-continued
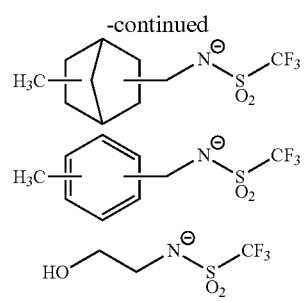
In the present invention, among the above, the anion moiety of the compound (D0-1) represented by general formula (d0) is preferably an anion moiety represented by general formula (d1-1) or (d1-2).
Hereinafter, specific examples of the compound (D0-1) will be described.
[Chemical formula 49]
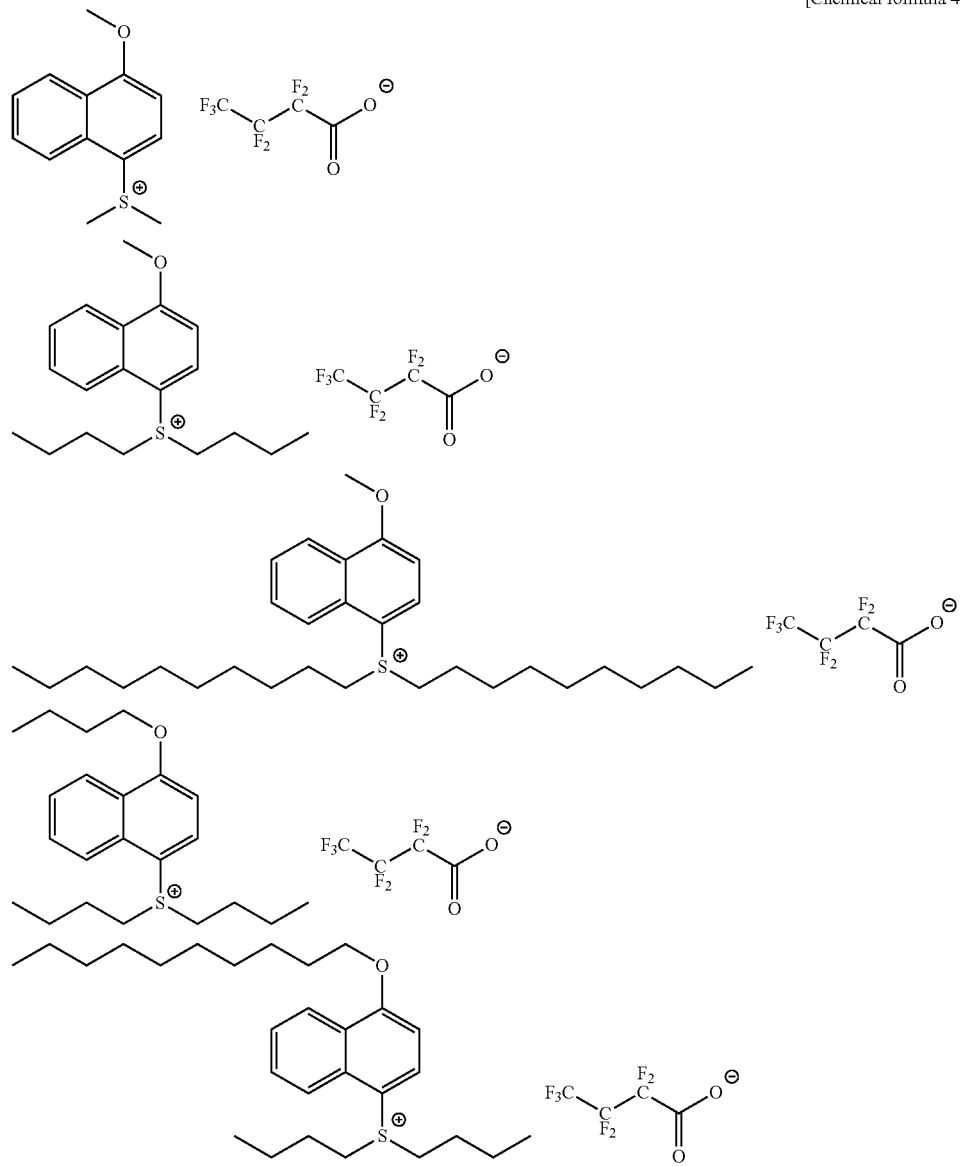

[Chemical formula 50]

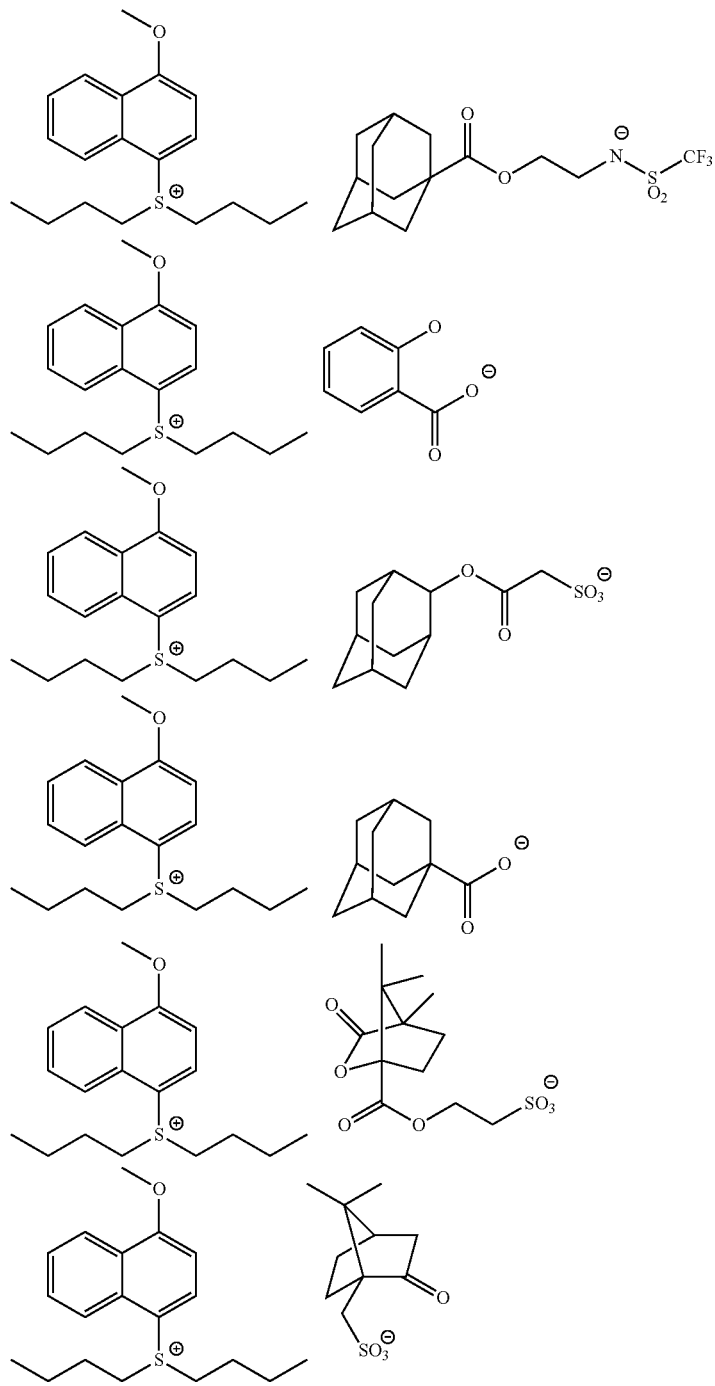

The component (D0) may use one type of the compound represented by general formula (d0), or may use two or more types thereof in combination.

The content of the component (D0) is preferably 0.5 parts by mass to 10.0 parts by mass, more preferably 0.5 parts by mass to 8.0 parts by mass, and still more preferably 1.0 part by mass to 8.0 parts by mass with respect to 100 parts by mass of the component (A). If the content is equal to or more than the lower limit of the aforementioned range, in particular, the excellent lithography properties and the excellent resist pattern shape can be obtained. If the content is equal to or less than the upper limit of the aforementioned range, the sensitivity can be maintained satisfactorily and a throughput is excellent.

The resist pattern formed by using the resist composition of the present invention has the excellent lithography properties. The reason is assumed to be as follows.

The quencher contained in the resist composition of the present invention contains the compound (D0-1) represented by general formula (d0). The compound (D0-1) has one alkoxy group represented by —ORa¹, as represented by general formula (d0) described above. It is considered that since the compound (D0-1) has one alkoxy group, the solubility in a developing solution of the compound can be appropriate and the excellent lithography properties can be obtained.

In addition, in the case where the compound (D0-1) has a predetermined cation moiety, it is considered that since the compound does not contain an unstable skeleton, the compound can contribute to the quality stability.

Component (D2)

The component (D) may contain a nitrogen-containing organic compound (hereinafter, referred to as component (D2)) which does not correspond to the component (D0).

The component (D2) acts as an acid diffusion control agent, and is not particularly limited as long as the component (D2) does not correspond to the component (D0), and the conventional components may be arbitrarily used. Among these, aliphatic amine, in particular, secondary aliphatic amine or tertiary aliphatic amine is preferable.

The aliphatic amine is amine having at least one aliphatic group and the aliphatic group preferably has 1 to 12 carbon atoms.

Examples of the aliphatic amine include amine in which at least one hydrogen atom of ammonia $NH_3$ is substituted with an alkyl group having equal to or less than 12 carbon atoms or a hydroxyalkyl group (alkylamine or alkyl alcohol amine) and cyclic amine.

Specific examples of the alkylamine and alkyl alcohol amine include monoalkylamine such as n-hexylamine, n-heptylamine, n-octylamine, n-nonylamine, and n-decylamine; dialkylamine such as diethylamine, di-n-propylamine, di-n-heptylamine, and di-n-octylamine, dicyclohexylamine; trialkylamine such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, and tri-n-dodecylamine; alkyl alcohol amine such as diethanolamine, triethanolamine, diisopropanolamine, triisopropanolamine, di-n-octanolamine, and tri-n-octanolamine. Among these, trialkylamine having 5 to 10 carbon atoms is still more preferable and tri-n-pentylamine or tri-n-octylamine is particularly preferable.

Examples of the cyclic amine include a heterocyclic compound including a nitrogen atom as a hetero atom. The heterocyclic compound may be monocyclic (aliphatic monocyclic amine) or polycyclic (aliphatic polycyclic amine).

Specific examples of the aliphatic monocyclic amine include piperidine, piperazine and the like.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylene tetramine, and 1,4-diazabicyclo[2.2.2]octane.

Other examples of the aliphatic amine include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, and triethanolamine triacetate, and triethanolamine triacetate is preferable.

In addition, aromatic amine may be used as the component (D2).

Examples of the aromatic amine include aniline, pyridine, 4-dimethylaminopyridine, pyrrole, indole, pyrazole, imidazole, or a derivative thereof, diphenylamine, triphenylamine, tribenzylamine, 2,6-diisopropylaniline, and N-tert-butoxycarbonylpyrrolidine.

The component (D2) may be used alone or two or more thereof may be used in combination.

The component (D2) is commonly used within a range of 0.01 parts by mass to 5.0 parts by mass with respect to 100 parts by mass of the component (A). If the component (D2) is used within the aforementioned range, the resist pattern shape and post-exposure temporal stability are improved.

As the component (D), one type of the compound may be used alone, or two or more types thereof may be used in combination.

In the case where the resist composition of the present invention contains the component (D), the content of the component (D) is preferably 0.1 parts by mass to 15 parts by mass, more preferably 0.3 parts by mass to 12 parts by mass, and still more preferably 0.5 parts by mass to 12 parts by mass with respect to 100 parts by mass of the component (A). If the content of the component (D) is equal to or more than the lower limit of the aforementioned range, when the component is used for the resist composition, the lithography properties such as LWR are improved. In addition, more excellent resist pattern shape can be obtained. If the content of the component (D) is equal to or less than the upper limit of the aforementioned range, the sensitivity can be maintained satisfactorily and a throughput is excellent.

Optional Components

Component (E)

In the present invention, the resist composition can contain at least one compound (E) (hereinafter, referred to as component (E)) selected from the group consisting of organic carboxylic acid, oxo acid of phosphorus, and a derivative thereof as an optional component, for the purpose of preventing deterioration of sensitivity, and improving the resist pattern shape and post-exposure temporal stability.

Preferred examples of the organic carboxylic acid include acetic acid, malonic acid, citric acid, malic acid, succinic acid, benzoic acid, and salicylic acid.

Examples of the oxo acid of phosphorus include phosphoric acid, phosphonic acid, and phosphinic acid, and among these, phosphonic acid is particularly preferable.

Examples of the derivative of the oxo acid of phosphorus include esters in which a hydrogen atom of the oxo acid is substituted with a hydrocarbon group, and examples of the hydrocarbon group include an alkyl group having 1 to 5 carbon atoms and an aryl group having 6 to 15 carbon atoms.

Examples of the phosphoric acid include phosphate such as phosphoric acid di-n-butylester and phosphoric acid diphenyl ester.

Examples of the derivative of the phosphonic acid include phosphonate such as phosphonic acid dimethyl ester, phosphonic acid-di-n-butylester, phenyl phosphonic acid, phosphonic acid diphenyl ester, and phosphonic acid dibenzyl ester.

Examples of the derivative of the phosphinic acid include phosphinate and phenyl phosphinic acid.

As the component (E), one type of the compound may be used alone, or two or more thereof may be used in combination.

The component (E) is commonly used within the range of 0.01 parts by mass to 5.0 parts by mass with respect to 100 parts by mass of the component (A).

Component (F)

In the present invention, the resist composition may contain a fluorine additive (hereinafter, referred to as "component (F)") in order to impart water repellency to a resist film.

As the component (F), for example, a fluorine-containing polymer compound disclosed in Japanese Unexamined Patent Application, Publication No. 2010-002870, Japanese Unexamined Patent Application, Publication No. 2010-032994, Japanese Unexamined Patent Application, Publication No. 2010-277043, Japanese Unexamined Patent Application, Publication No. 2011-13569, and Japanese Unexamined Patent Application, Publication No. 2011-128226 can be used.

Specific examples of the component (F) include a polymer having a structural unit (f1) represented by formula (f1-1) shown below. As the polymer, a polymer (homopolymer) only composed of a structural unit (f1) represented by formula (f1-1) shown below; a copolymer of the structural unit (f1) represented by formula (f1-1) shown below and the structural unit (a1); or a copolymer of the structural unit (f1) represented by formula (f1-1) shown below, a structural unit derived from acrylic acid or methacrylic acid, and the structural unit (a1) is preferable. Here, as the structural unit (a1) copolymerized with the structural unit (f1) represented by formula (f1-1) shown below, 1-ethyl-1-cyclooctyl(meth)acrylate or a structural unit represented by formula (a1-2-01) is preferable.

[Chemical formula 51]

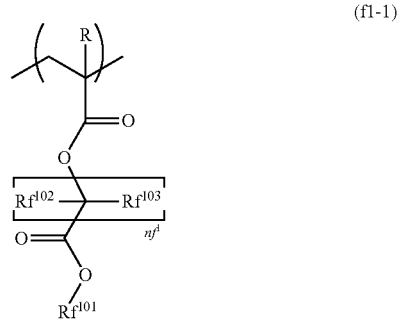

(f1-1)

In the formula, R represents the same as described above, $Rf^{102}$ and $Rf^{103}$ each independently represent a hydrogen atom, a halogen atom, an alkyl group having 1 to 5 carbon atoms, or a halogenated alkyl group having 1 to 5 carbon atoms; and $Rf^{102}$ and $Rf^{103}$ may be the same as or different from each other. $nf^1$ is an integer of 1 to 5; and $Rf^{101}$ is an organic group including a fluorine atom.

In formula (f1-1), R represents the same as described above. R is preferably a hydrogen atom or a methyl group.

In formula (f1-1), examples of the halogen atom for $Rf^{102}$ and $Rf^{103}$ include a fluorine atom, a chlorine atom, a bromine atom, and an iodine atom, and a fluorine atom is particularly preferable. Examples of the alkyl group having 1 to 5 carbon atoms for $Rf^{102}$ and $Rf^{103}$ include the same alkyl group having 1 to 5 carbon atoms exemplified for R, and a methyl group or an ethyl group is preferable. Specific examples of the halogenated alkyl group having 1 to 5 carbon atoms for $Rf^{102}$ and $Rf^{103}$ include groups in which a part or all of the hydrogen atoms of the alkyl group having 1 to 5 carbon atoms are substituted with a halogen atom. Examples of the halogen atom include a fluorine atom, a chlorine atom, a bromine atom, and an iodine atom, and a fluorine atom is particularly preferable. Among these, as $Rf^{102}$ and $Rf^{103}$, a hydrogen atom, a fluorine atom, or an alkyl group having 1 to 5 carbon atoms is preferable, a hydrogen atom, a fluorine atom, a methyl group, or an ethyl group is preferable.

In formula (f1-1), $nf^1$ is an integer of 1 to 5, preferably an integer of 1 to 3, and more preferably 1 or 2.

In formula (f1-1), $Rf^{101}$ represents an organic group including a fluorine atom, and preferably a hydrocarbon group including a fluorine atom.

The hydrocarbon group including a fluorine atom may be linear, branched, or cyclic, and preferably has 1 to 20 carbon atoms, more preferably 1 to 15 carbon atoms, and particularly preferably 1 to 10 carbon atoms.

In addition, in the hydrocarbon group including a fluorine atom, 25% or more of hydrogen atoms in the hydrocarbon group are preferably fluorinated, 50% or more thereof are more preferably fluorinated, and 60% or more thereof are particularly preferably fluorinated, in order to increase hydrophobicity of the resist film at the time of immersion exposure.

Among these, as $Rf^{101}$, a fluorinated hydrocarbon group having 1 to 5 carbon atoms is particularly preferable, and a methyl group, —$CH_2$—$CF_3$, —$CH_2$—$CF_2$—$CF_3$, —CH($CF_3$)$_2$, —$CH_2$—$CH_2$—$CF_3$, or —$CH_2$—$CH_2$—$CF_2$—$CF_2$—$CF_2$—$CF_3$ is most preferable.

The weight average molecular weight (Mw) in terms of polystyrene determined by gel permeation chromatography of the component (F) is preferably 1,000 to 50,000, more preferably 5,000 to 40,000, and most preferably 10,000 to 30,000. If the weight average molecular weight is equal to or less than the upper limit of the aforementioned range, sufficient solubility to a resist solvent are obtained in use of the component (F) for the resist, and if the weight average molecular weight is equal to or more than the lower limit of the aforementioned range, dry etching resistance or cross-sectional shape of the resist pattern is satisfactory.

The dispersivity (Mw/Mn) of the component (F) is preferably 1.0 to 5.0, more preferably 1.0 to 3.0, and most preferably 1.2 to 2.5.

As the component (F), one type of the compound may be used alone, or two or more thereof may be used in combination.

The component (F) is commonly used in a ratio of 0.5 parts by mass to 10 parts by mass with respect to 100 parts by mass of the component (A).

In the present invention, further, miscible additives, for example, an additive resin for improving properties of the resist film, a dissolution inhibitor, a plasticizer, a stabilizer, a colorant, a halation inhibitor, or dye can be appropriately added to the resist composition according to the desire.

Component (S)

In the present invention, the resist composition can be produced by dissolving a material in an organic solvent (hereinafter, may be referred to as component (S)).

The component (S) may be any organic solvent which can dissolve the respective components to be used to give a uniform solution, and one or more of any organic solvent can be appropriately selected from those which have been conventionally known as solvents for a chemically amplified resist.

Examples thereof include lactones such as γ-butyrolactone; ketones such as acetone, methyl ethyl ketone (MEK), cyclohexanone, methyl-n-pentyl ketone (2-heptanone) and methyl isopentyl ketone; polyhydric alcohols, such as ethylene glycol, diethylene glycol, propylene glycol and dipropylene glycol; polyhydric alcohol derivatives including compounds having an ester bond, such as ethylene glycol monoacetate, diethylene glycol monoacetate, propylene glycol monoacetate, and dipropylene glycol monoacetate, and compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These organic solvents may be used alone, or two or more thereof may be used in combination as a mixed solvent.

Among these, PGMEA, PGME, γ-butyrolactone, or EL is preferable.

In addition, a mixed solvent obtained by mixing PGMEA with a polar solvent is preferable. The mixing ratio (mass ratio) of the mixed solvent can be appropriately determined, taking into consideration the compatibility of the PGMEA with the polar solvent, but is preferably in the range of 1:9 to 9:1, and more preferably from 2:8 to 8:2.

Specifically, in the case where EL or cyclohexanone is mixed as the polar solvent, the PGMEA:EL or cyclohexanone mass ratio is preferably from 1:9 to 9:1, and more preferably from 2:8 to 8:2. Alternatively, in the case where PGME is mixed as the polar solvent, the PGMEA:PGME mass ratio is preferably from 1:9 to 9:1, more preferably from 2:8 to 8:2, and still more preferably 3:7 to 7:3.

Further, as the component (S), in addition to the above, a mixed solvent of at least one of PGMEA and EL with γ-butyrolactone is also preferable. In this case, the mixing ratio (former:latter) of such a mixed solvent is preferably from 70:30 to 95:5.

The use amount of the component (S) is not particularly limited, and is appropriately set to a concentration which enables coating to a substrate, according to the thickness of the coated film. In general, the organic solvent is used such that the solid content of the resist composition is 1 mass % to 20 mass %, and preferably from 2 mass % to 15 mass %.

Method for Forming a Resist Pattern

In the present invention, a resist pattern can be formed by forming a resist film on a support using the resist composition, exposing the resist film, and developing the resist film.

A method for forming a resist pattern can be carried out for example, as follows.

First, the aforementioned resist composition is applied onto the support by a spinner, and subjected to a baking treatment (post applied bake (PAB)), for example, at temperature conditions of 80° C. to 150° C. for 40 seconds to 120 seconds, preferably 60 seconds to 90 seconds to form a resist film.

Next, after selective exposure of the resist film is carried out, either by exposure through a mask having a predetermined pattern formed thereon (mask pattern) using an exposure apparatus such as an ArF exposure apparatus, an electron beam lithography apparatus or an EUV exposure apparatus, or by patterning via direct irradiation with an electron beam without using a mask pattern, baking treatment (post exposure baking (PEB)) is carried out under temperature conditions of 80° C. to 150° C. for 40 seconds to 120 seconds, and preferably 60 seconds to 90 seconds.

Next, the resist film is subjected to a developing treatment.

The developing treatment is carried out using an alkali developing solution in the case of an alkali developing process, and a developing solution containing an organic solvent (organic developing solution) in the case of a solvent developing process.

After the developing treatment, it is preferable to conduct a rinse treatment. The rinse treatment is preferably conducted using pure water in the case of an alkali developing process, and a rinse solution containing an organic solvent in the case of a solvent developing process.

In the case of a solvent developing process, after the developing treatment or the rinse treatment, the developing solution or the rinse liquid attached on the pattern can be removed by a treatment using a supercritical fluid.

After the developing treatment or the rinse treatment, drying is conducted. If desired, baking treatment (post bake) can be conducted following the developing treatment. In this manner, a resist pattern can be obtained.

The developing process of the present invention may be an alkali developing process or a solvent developing process.

Support

The support is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the support, an inorganic and/or organic film may be provided on the substrate as described above. As the inorganic film, an inorganic antireflection film (inorganic BARC) can be used. As the organic film, an organic antireflection film (organic BARC) and an organic film such as a lower-layer organic film used in a multilayer resist method can be used.

Here, a multilayer resist method is a method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beams (EB), X-rays, and soft X-rays. The resist composition is effective to KrF excimer laser, ArF excimer laser, EB or EUV.

The exposure of the resist film can be either a general exposure (dry exposure) conducted in air or an inert gas such as nitrogen, or liquid immersion exposure (liquid immersion lithography).

In liquid immersion lithography, the region between the resist film and the lens at the lowermost point of the exposure apparatus is pre-filled with a solvent (liquid immersion medium) that has a larger refractive index than the refractive index of air, and the exposure (liquid immersion exposure) is conducted in this state.

The liquid immersion medium preferably exhibits a refractive index larger than the refractive index of air but smaller than the refractive index of the resist film to be exposed. The refractive index of the solvent is not particularly limited as long as the index satisfies the aforementioned range.

Examples of this liquid immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point preferably within a range from 70° C. to 180° C. and more preferably from 80° C. to 160° C. A fluorine-based inert liquid having a boiling point within the aforementioned range is preferable in that the removal of the liquid immersion medium after the exposure can be conducted by a simple method.

As a fluorine-based inert liquid, a perfluoroalkyl compound in which all of the hydrogen atoms of the alkyl group are substituted with fluorine atoms is particularly preferable. Examples of these perfluoroalkyl compounds include perfluoroalkylether compounds and perfluoroalkylamdne compounds.

Specifically, one example of the perfluoroalkylether compound is perfluoro(2-butyl-tetrahydrofuran) (boiling point 102° C.), and an example of the perfluoroalkylamine compound is perfluorotributylamine (boiling point 174° C.)

As the liquid immersion medium, water is preferably used in terms of cost, safety, environment and versatility.

As the alkali developing solution used in an alkali developing process, a 0.1 mass % to 10 mass % aqueous solution of tetramethylammonium hydroxide (TMAH) can be exemplified.

As the organic solvent contained in the organic developing solution used in a solvent developing process, any of the conventional organic solvents can be used as long as the organic solvent is capable of dissolving the component (A) (component (A) prior to exposure). Specific examples of the organic solvent include polar solvents such as ketone-based solvents, ester-based solvents, alcohol-based solvents, amide-based solvents and ether-based solvents, and hydrocarbon-based solvents.

If necessary, the organic developing solution may have a conventional additive mixed. Examples of the additive include surfactants. The surfactant is not particularly limited, and for example, an ionic or non-ionic fluorine-based and/or silicon-based surfactant can be used.

In the case where a surfactant is added, the mixing amount thereof is commonly 0.001 mass % to 5 mass %, preferably 0.005 mass % to 2 mass %, and more preferably 0.01 mass % to 0.5 mass % with respect to the total amount of the organic developing solution.

The developing treatment can be performed by a conventional developing method. Examples thereof include a method in which the support is immersed in the developing solution for a predetermined time (a dip method), a method in which the developing solution is cast up on the surface of the support by surface tension and maintained for a predetermined period (a puddle method), a method in which the developing solution is sprayed onto the surface of the support (spray method), and a method in which the developing solution is continuously ejected from a developing solution ejecting nozzle while scanning at a constant rate to apply the developing solution to the support while rotating the support at a constant rate (dynamic dispense method).

The rinse treatment using a rinse liquid (washing treatment) can be conducted by a conventional rinse method. Examples of the rinse method include a method in which the rinse liquid is continuously applied onto the support while rotating the support at a constant rate (rotational coating method), a method in which the support is immersed in the rinse liquid for a predetermined time (dip method), and a method in which the rinse liquid is sprayed onto the surface of the support (spray method).

Photo-Reactive Quencher

The third aspect of the present invention is a photo-reactive quencher which contains a compound (D0-1) represented by general formula (d0) shown below.

[Chemical formula 52]

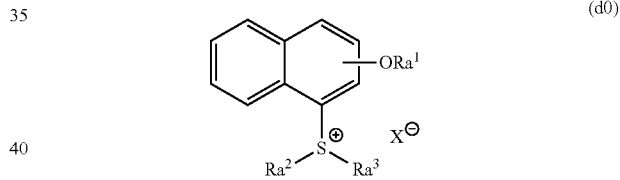

(d0)

In the formula, $Ra^1$ represents an alkyl group having 1 to 10 carbon atoms which may have a substituent, $Ra^2$ and $Ra^3$ each independently represent an alkyl group having 1 to 10 carbon atoms which may have a substituent. $X^-$ represents a counter anion.

[Chemical formula 53]

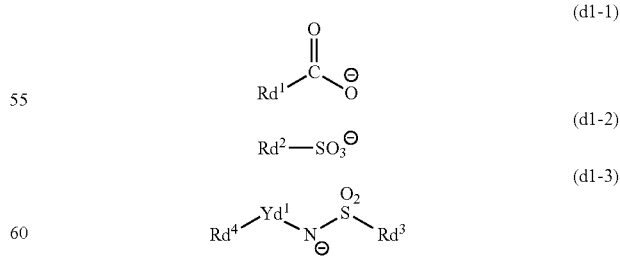

(d1-1)

(d1-2)

(d1-3)

In formulae (d1-1) to (d1-3), $Rd^1$ to $Rd^4$ represent a cyclic group which may have a substituent, a chain-like alkyl group which may have a substituent, or a chain-like alkenyl group which may have a substituent. However, a fluorine atom bonded to a carbon atom adjacent to a sulfur atom in $Rd^2$ of formula (d1-2) is no more than two. $Yd^1$ represents a single bond or a divalent linking group.

As the photo-reactive quencher of the present invention, the explanation of compound (D0-1) represented by general formula (d0) is the same as the explanation with regard to the compound (D0-1) represented by general formula (d0) described in the resist composition according to the first aspect of the present invention.

Compound

The fourth aspect of the present invention is a compound represented by general formula (d0) shown below.

[Chemical formula 54]

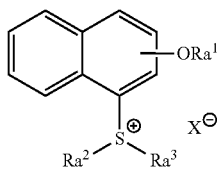

(d0)

In the formula, $Ra^1$ represents an alkyl group having 1 to 10 carbon atoms which may have a substituent, $Ra^2$ and $Ra^3$ each independently represent an alkyl group having 1 to 10 carbon atoms which may have a substituent. $X^-$ represents a counter anion.

[Chemical formula 55]

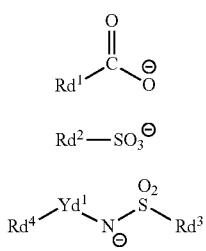

(d1-1)

(d1-2)

(d1-3)

In formulae (d1-1) to (d1-3), $Rd^1$ to $Rd^4$ represent a cyclic group which may have a substituent, a chain-like alkyl group which may have a substituent, or a chain-like alkenyl group which may have a substituent. However, a fluorine atom bonded to a carbon atom adjacent to a sulfur atom in $Rd^2$ of formula (d1-2) is no more than two. $Yd^1$ represent a single bond or a divalent linking group.

In the compound of the present invention, the explanation of the compound represented by general formula (d0) is the same as the explanation with regard to the compound represented by general formula (d0) described in the resist composition according to the first aspect of the present invention.

The compound of the present invention is suitable for a photo-reactive type quencher of the resist composition.

The compound of the present invention can be produced by the conventional method.

For example, a compound (D0-1) can be derived by exchanging salts between the compound represented by general formula (d0-0) shown below and a desired anion. As the desired anion, each anion represented by formulae (d1-1) to (d1-3) is particularly preferable. As the compound (d0-0), commercially available compounds may be used, or compounds synthesized by the conventional production method may be used.

[Chemical formula 56]

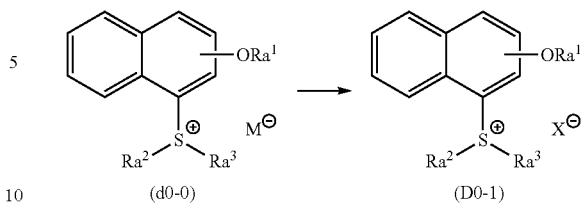

[In the formula, $Ra^1$ represents an alkyl group having 1 to 10 carbon atoms which may have a substituent, $Ra^2$ and $Ra^3$ each independently represent an alkyl group having 1 to 10 carbon atoms which may have a substituent. $M^-$ and $X^-$ represent a counter anion.]

After the reaction is completed, the compound in the reaction liquid may be isolated and purified. The conventional methods can be used for isolation and purification. Examples thereof include condensation, solvent extraction, distillation, crystallization, recrystallization, chromatography, and any one of these may be used alone or two or more thereof may be used in combination.

The structure of the compound obtained by the above methods can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis, and X-ray crystal diffraction.

EXAMPLES

Hereinafter, the present invention will be described in more detail using Examples, and the present invention is not limited to the following Examples.

Preparation of Resist Composition 1: Examples 1 to 11 and Comparative Examples 1 to 3

100 parts by mass of the following polymer compound (A)-1, 6 parts by mass of the following compound (B)-1, 5 parts by mass of a compound having an anion moiety and 3 parts by mass of a compound having a cation moiety as shown in the following Tables 1 to 4 as the component (D), the following polymer compound (F)-1, 0.2 parts by mass of salicylic acid, 100 parts by mass of γ-butyrolactone, and 4,000 parts by mass of a solvent (mixed solvent of PGMEA, PGME, and cyclohexanone (mass ratio 45/30/25)) are mixed to thereby prepare a resist composition of each of Examples 1 to 11 and Comparative Examples 1 to 3.

[Chemical formula 57]

(A)-1

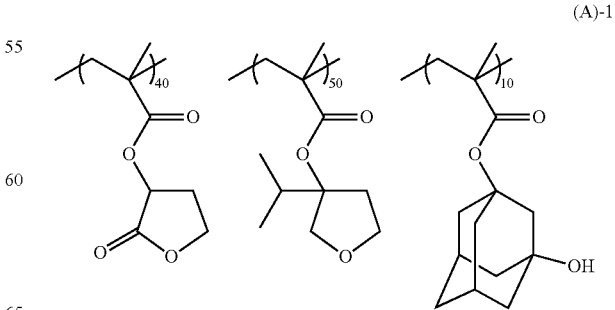

Mw: 7,000, PDI: 1.71

-continued (B)-1
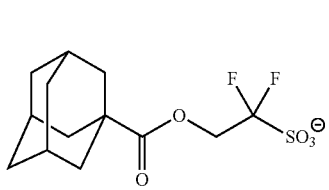 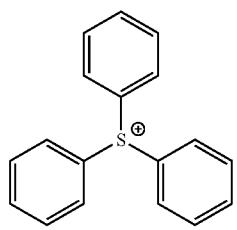 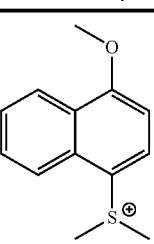

(F)-1
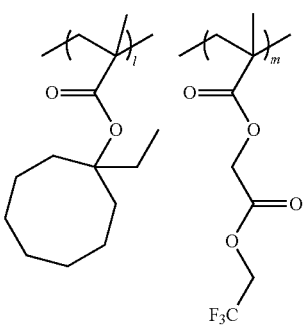
(Molar ratio: l/m = 77/23), Mw is 23,100, Mw/Mn is 1.78.

TABLE 1

| | Component (D) | |
|---|---|---|
| | Cation moiety | Anion moiety |
| Example 1 | 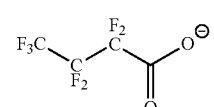 (naphthalene cation) | 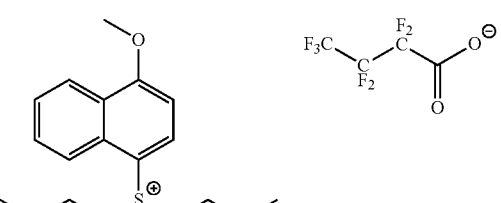 |

1H NMR
¹H NMR (DMSO-d6) δ (ppm) = 8.54 (d, 1H), 8.35 (m, 2H), 7.91-7.70 (m, 2H), 7.42 (d, 1H), 4.17 (s, 3H), 3.91 (d, 6H).
19F NMR
¹⁹F NMR (DMSO-d6) δ (ppm) = −78.3 (t, 3F), −114.5 (m, 2F), −124.7 (s, 2F)

| Example 2 | (naphthalene cation with dibutyl) | (anion) |

1H NMR
¹H NMR (DMSO-d6) δ (ppm) = 8.54 (d, 1H), 8.35 (m, 2H), 7.91-7.70 (m, 2H), 7.42 (d, 1H), 4.17 (s, 3H), 4.00-3.82 (m, 4H), 1.62-1.30 (m, 8H), 0.82 (t, 6H).
19F NMR
¹⁹F NMR (DMSO-d6) δ (ppm) = −78.3 (t, 3F), −114.5 (m, 2F), −124.7 (s, 2F)

TABLE 2

| | Component (D) | |
|---|---|---|
| | Cation moiety | Anion moiety |
| Example 3 | 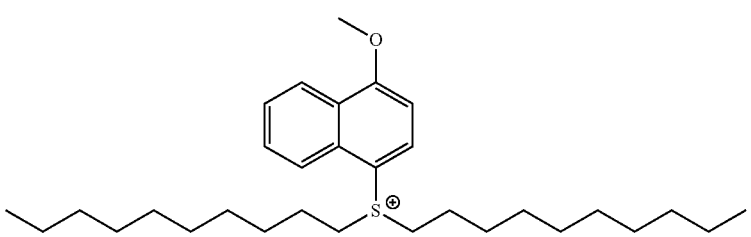 [SMILES: CCCCCCCCCC[S+](CCCCCCCCCC)c1ccc(OC)c2ccccc12] | 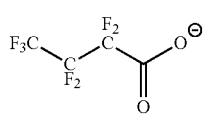 [SMILES: O=C([O-])C(F)(F)C(F)(F)C(F)(F)F] |

1H NMR
¹H NMR (DMSO-d6) δ (ppm) = 8.54 (d, 1H), 8.35 (m, 2H), 7.91-7.70 (m, 2H), 7.42 (d, 1H), 4.17 (s, 3H), 4.00-3.82 (m, 4H), 1.62-1.30 (m, 32H), 0.82 (t, 6H).
19F NMR
¹⁹F (DMSO-d6) δ (ppm) = −78.3 (t, 3F), −114.5 (m, 2F), −124.7 (s, 2F)

TABLE 2-continued

| Component (D) | |
|---|---|
| Cation moiety | Anion moiety |

Example 4

[Structure: 4-butoxy-naphthyl dibutylsulfonium cation] [Structure: F₃C–CF₂–CF₂–C(=O)–O⁻]

1H NMR
¹H NMR (DMSO-d6) δ (ppm) = 8.54 (d, 1H), 8.35 (m, 2H), 7.91-7.70 (m, 2H), 7.42 (d, 1H), 4.37 (t, 2H), 4.00-3.82 (m, 4H), 1.91 (m, 2H), 1.62-1.30 (m, 10H), 1.02 (t, 3H), 0.82 (t, 6H).
19F NMR
¹⁹F NMR (DMSO-d6) δ (ppm) = −78.3 (t, 3F), −114.5 (m, 2F), −124.7 (s, 2F)

TABLE 3

| Component (D) | |
|---|---|
| Cation moiety | Anion moiety |

Example 5

[Structure: 4-(decyloxy)naphthyl dibutylsulfonium cation] [Structure: F₃C–CF₂–CF₂–C(=O)–O⁻]

1H NMR
¹H NMR (DMSO-d6) δ (ppm) = 8.54 (d, 1H), 8.35 (m, 2H), 7.91-7.70 (m, 2H), 7.42 (d, 1H), 4.37 (m, 2H), 4.00-3.82 (m, 4H), 1.91 (m, 2H), 1.62-1.30 (m, 22H), 1.02 (t, 3H), 0.82 (t, 6H).
19F NMR
¹⁹F NMR (DMSO-d6) δ (ppm) = −78.3 (t, 3F), −114.5 (m, 2F), −124.7 (s, 2F)

Comparative Example 1

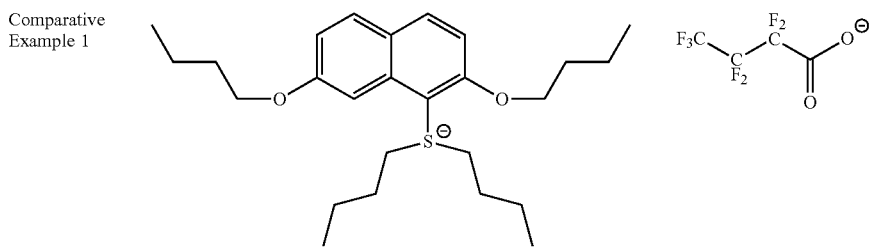

Comparative Example 2

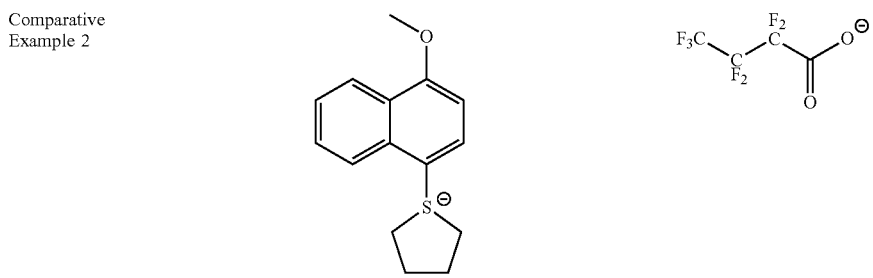

TABLE 4
| | Component (D) | |
|---|---|---|
| | Cation moiety | Anion moiety |
| Example 6 | 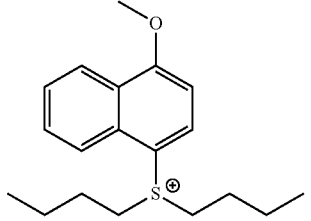 [SMILES: CCCC[S+](CCCC)c1ccc(OC)c2ccccc12] | 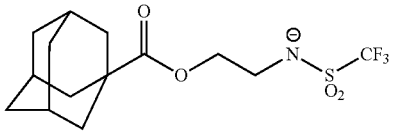 [SMILES: O=C(OCC[N-]S(=O)(=O)C(F)(F)F)C12CC3CC(CC(C3)C1)C2] |
1H NMR
1H NMR (DMSO-d6) δ (ppm) = 8.54 (d, 1H), 8.35 (m, 2H), 7.91-7.70 (m, 2H), 7.42 (d, 1H), 4.17 (s, 3H), 4.00-3.82 (m, 6H), 3.08-3.00 (t, 2H), 1.93-1.30 (m, 23H), 0.82 (t, 6H).
19F NMR
19F NMR (DMSO-d6) δ (ppm) = −73.2 (s, 2F).
| Example 7 | 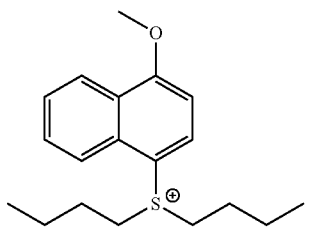 [SMILES: CCCC[S+](CCCC)c1ccc(OC)c2ccccc12] | |
1H NMR
1H NMR (DMSO-d6) δ (ppm) = 8.54 (d, 1H), 8.35 (m, 2H), 7.91-7.70 (m, 2H), 7.65 (m, 1H), 7.42 (d, 1H), 7.08 (m, 1H), 6.55 (m, 2H), 4.17 (s, 3H), 4.00-3.82 (m, 4H), 1.62-1.30 (m, 8H), 0.82 (t, 6H).
TABLE 5
| | Component (D) | |
|---|---|---|
| | Cation moiety | Anion moiety |
| Example 8 | 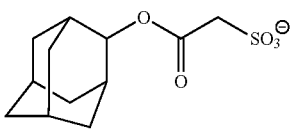 | 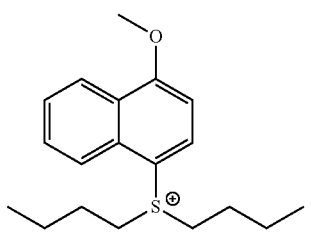 |
1H NMR
1H NMR (DMSO-d6) δ (ppm) = 8.54 (d, 1H), 8.35 (m, 2H), 7.91-7.70 (m, 2H), 7.42 (d, 1H), 4.73 (m, 1H), 4.17 (s, 3H), 4.00-3.82 (m, 4H), 3.44 (m, 2H), 2.10-1.30 (m, 22H), 0.82 (t, 6H).
| Example 9 | | 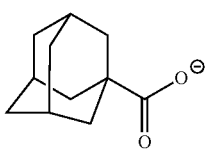 [SMILES: O=C([O-])C12CC3CC(CC(C3)C1)C2] |
1H NMR
1H NMR (DMSO-d6) δ (ppm) = 8.54 (d, 1H), 8.35 (m, 2H), 7.91-7.70 (m, 2H), 7.42 (d, 1H), 4.17 (s, 3H), 4.00-3.82 (m, 4H), 2.00-1.64 (m, 15H), 1.62-1.30 (m, 8H), 0.82 (t, 6H).

TABLE 6

| | Component (D) | |
|---|---|---|
| | Cation moiety | Anion moiety |
| Example 10 | [structure] 1H NMR (DMSO-d6) δ (ppm) = 8.54 (d, 1H), 8.35 (m, 2H), 7.91-7.70 (m, 2H), 7.42 (d, 1H), 4.44-4.30 (m, 2H), 4.17 (s, 3H), 4.00-3.82 (m, 4H), 2.79 (t, 2H), 2.40-2.33 (m, 1H), 1.99-1.86 (m, 2H), 1.62-1.30 (m, 9H), 1.00 (d, 6H), 0.84-0.75 (m, 9H). | [structure] |
| Example 11 | [structure] 1H NMR (DMSO-d6) δ (ppm) = 8.54 (d, 1H), 8.35 (m, 2H), 7.91-7.70 (m, 2H), 7.42 (d, 1H), 4.17 (s, 3H), 4.00-3.82 (m, 4H), 2.88 (d, 1H), 2.74-2.66 (m, 1H), 2.37 (d, 1H), 2.24-2.17 (m, 1H), 1.90 (t, 1H), 1.89-1.74 (m, 2H), 1.62-1.30 (m, 8H), 1.29-1.22 (m, 2H), 1.03 (s, 3H), 0.82 (t, 6H), 0.71 (s, 3H). | [structure] |
| Comparative Example 3 | [structure] | $CF_3SO_3^{\ominus}$ |

Formation of Solvent Developing Negative-type Resist Pattern: Examples 1 to 11 and Comparative Examples 1 to 3

An organic antireflection film composition "ARC29A" (trade name, Brewer Science, Inc.) was applied onto a 12 inch silicon wafer using a spinner, baked on a hot plate at a temperature of 205° C. for 60 seconds, and dried to form an organic antireflection film having a film thickness of 90 nm.

Next, the resist composition was applied onto the film using a spinner, subjected to a prebake (PAB) treatment on a hot plate under a condition of 110° C. for 60 seconds, and dried to form a resist film having a film thickness of 85 nm.

Next, the resist film was selectively irradiated with ArF excimer lasers (193 nm) using an exposure apparatus NSR-S609B (manufactured by Nikon Corporation NA=1.07 Annular 0.78/0.97 w/o P) via a mask pattern.

Next, a solvent development was conducted using butyl acetate for 13 seconds.

After that, a post exposure bake treatment was conducted at a temperature of 95° C. (PEB(° C.)) for 60 seconds.

As a result, the following line and space pattern (hereinafter, referred to as "LS pattern") was formed.
 LS pattern 1: 100 nm pitch/37 nm line, mask size: 50 nm
 Evaluation of Line Width Roughness (LWR)

With respect to the resist pattern formed as above, the space width of the LS pattern was measured using a measuring SEM (acceleration voltage 300 V) at 400 points in the lengthwise direction of the space. The scanning electron microscope manufactured by Hitachi High-Technologies Corporation (trade name: S-9380) was used as the measuring SEM.

Next, the value of 3 times the standard deviation(s) (3s) was determined from the measurement result of the space width of the each pattern, and the average of the 3s values at 400 points was calculated as a yardstick of LWR. The results are shown in Table 5 as "LWR".

The smaller this 3s value is, the lower the level of roughness of the space portion, indicating that an SL pattern having a space with a uniform width was obtained.

Temporal Stability

1) With respect to each of the resist compositions stored at room temperature and −20° C. for 1 month, a line and space pattern was formed by a method for forming a resist pattern with the optimal exposure amount Eop, and a space width (CD) was measured.

2) With respect to the resist composition of each example, with respect to each of the respective resist compositions stored at room temperature and −20° C. for 1 month, CD variation value; "ΔCD (nm)" was calculated.

With respect to the case where ΔCD is 2 nm or less, the storage stability of the resist composition is rated excellent and was designated as "A" and with respect to the case where ΔCD exceeds 2 nm, the storage stability was designated as "B".

TABLE 7

| | LWR | Evaluation of temporal stability |
|---|---|---|
| Example 1 | 4.7 | A |
| Example 2 | 4.4 | A |
| Example 3 | 4.6 | A |
| Example 4 | 4.5 | A |
| Example 5 | 4.7 | A |
| Example 6 | 4.5 | A |
| Example 7 | 4.4 | A |
| Example 8 | 4.4 | A |
| Example 9 | 4.5 | A |
| Example 10 | 4.7 | A |
| Example 11 | 4.6 | A |
| Comparative Example 1 | 5.5 | A |
| Comparative Example 2 | 4.8 | B |
| Comparative Example 3 | Unresolved | — |

Preparation of Resist Composition 2: Examples 12 and Comparative Examples 4 to 5

100 parts by mass of the following polymer compound (A)-2, 6 parts by mass of the following compound (B)-1, 5 parts by mass of a compound having an anion moiety and 3 parts by mass of a compound having a cation moiety as shown in the following Table 6 as the component (D), 3 parts by mass of the following polymer compound (F)-1, 0.2 parts by mass of salicylic acid, 100 parts by mass of γ-butyrolactone, and 4,000 parts by mass of a solvent (mixed solvent of PGMEA, PGME, and cyclohexanone (mass ratio 45/30/25)) to thereby prepare a resist composition of each Example 12 and Comparative Examples 4 and 5.

[Chemical formula 58]

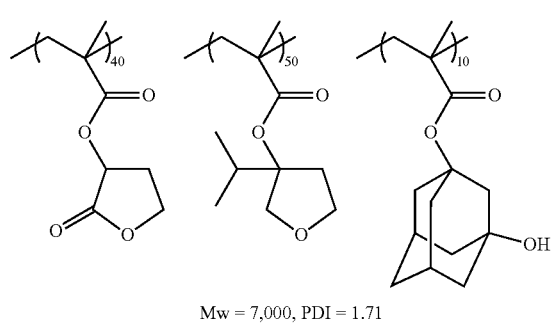

Mw = 7,000, PDI = 1.71

TABLE 8

| | Component (D) | |
|---|---|---|
| | Cation moiety | Anion moiety |
| Example 12 | (naphthalene with methoxy group and dibutyl sulfonium) | $F_3C-C(F_2)-C(F_2)-C(=O)-O^{\ominus}$ |
| Comparative Example 4 | (naphthalene with two butoxy groups and dibutyl sulfonium) | $F_3C-C(F_2)-C(F_2)-C(=O)-O^{\ominus}$ |
| Comparative Example 5 | (naphthalene with methoxy group and tetrahydrothiophenium) | $F_3C-C(F_2)-C(F_2)-C(=O)-O^{\ominus}$ | a hot plate under a condition of 110° C. for 60 seconds, and dried to thereby form a resist film having a film thickness of 90 nm.

Next, the resist film was selectively irradiated with ArF excimer lasers (193 nm) using an exposure apparatus NSR-S609B (manufactured by Nikon Corporation NA=1.07 Dipole 0.78/0.97 w/o P) via a mask pattern.

Next, alkali development was conducted at a temperature of 23° C. for 10 seconds using 2.38 mass % tetramethyl-ammonium hydroxide (TMAH) aqueous solution "NMD-3" (trade name, manufactured by TOKYO OHKA KOGYO CO., LTD.).

After that, a post exposure bake treatment was conducted at a temperature of 95° C. (PEB(° C.)) for 60 seconds.

As a result, the following line and space pattern (hereinafter, referred to as "LS pattern") was formed.

<Formation of Alkali Developing Positive-type Resist Pattern: Example 12 and Comparative Examples 4 to 5

An organic antireflection film composition "ARC29A" (trade name, Brewer Science, Inc.) was applied onto a 12 inch silicon wafer using a spinner, baked on a hot plate at a temperature of 205° C. for 60 seconds, and dried to thereby form an organic antireflection film having a film thickness of 90 nm.

Next, the resist composition was applied onto the film using a spinner, subjected to a prebake (PAB) treatment on Evaluation of Line Width Roughness (LWR)

With respect to the resist pattern formed as above (LS pattern 1: 100 nm pitch/50 nm line, mask size 50 nm), the space width of the LS pattern was measured using a measuring SEM (acceleration voltage 300 V) at 400 points in the lengthwise direction of the space. The scanning electron microscope manufactured by Hitachi High-Technologies Corporation (trade name: S-9380) was used as the measuring SEM.

Next, the value of 3 times the standard deviation (s) (3s) was determined from the measurement result of the space width of the each pattern, and the average of the 3s values at 400 points was calculated as a yardstick of LWR. The results are shown in Table 7 as "LWR".

The smaller this 3s value is, the lower the level of roughness of the space portion, indicating that an SL pattern having a space with a uniform width was obtained.

Temporal Stability

1) With respect to each of the resist compositions stored at room temperature and −20° C. for 1 month, a line and space pattern was formed by a method for forming a resist pattern with the optimal exposure amount Eop (LS pattern 2: 100 nm pitch/37 nm line, mask size 50 nm), and a space width (CD) was measured.

2) With respect to the resist composition of each example, with respect to each of the resist compositions stored at room temperature and −20° C. for 1 month, CD variation value; "ΔCD (nm)" was calculated.

With the case where ΔCD is 2 nm or less, the storage stability of the resist composition was rated excellent and was designated as "A", and with respect to the case where ΔCD exceeds 2 nm, the storage stability was designated as "B". The result thereof is shown in Table 9.

TABLE 9

|  | LWR | Evaluation of temporal stability |
|---|---|---|
| Example 12 | 3.9 | A |
| Comparative Example 4 | 4.4 | A |
| Comparative Example 5 | 4.7 | B |

As shown in the above result, the resist composition of the present invention including a quencher containing the compound (D0-1) represented by general formula (d0) is excellent in LWR and temporal stability.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates an acid upon exposure and whose solubility in a developing solution changes under the action of an acid, the composition comprising:
   a base material component (A) whose solubility in a developing solution changes under the action of an acid;
   an acid generator component (B) which generates an acid upon exposure; and
   a photo-reactive quencher (D0) which contains a compound (D0-1) represented by general formula (d0) shown below:

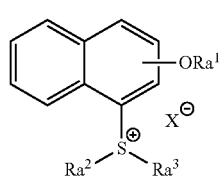

(d0)

wherein $Ra^1$ represents an alkyl group having 1 to 10 carbon atoms which may have a substituent, $Ra^2$ and $Ra^3$ each independently represent an alkyl group having 1 to 10 carbon atoms which may have a substituent, and $X^-$ represents a counter anion represented by any one of general formulae (d1-1) to (d1-3) shown below:

(d1-1)

(d1-2)

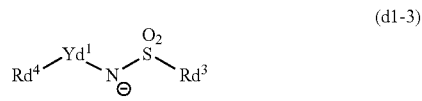

(d1-3)

wherein $Rd^1$ to $Rd^4$ each independently represents a cyclic group which may have a substituent, a chain-like alkyl group which may have a substituent, or a chain-like alkenyl group which may have a substituent, provided that two or more of fluorine atoms are not bonded to a carbon atom adjacent to an S atom in $Rd^2$ in formula (d1-2); and $Yd^1$ represents a single bond or a divalent linking group.

2. A method for forming a resist pattern, comprising:
   forming a resist film using the resist composition according to claim 1 on a support;
   exposing the resist film to light; and
   developing the resist film to form a resist pattern.

3. A photo-reactive quencher comprising a compound (D0-1) represented by general formula (d0) shown below:

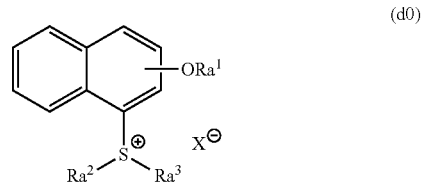

(d0)

wherein $Ra^1$ represents an alkyl group having 1 to 10 carbon atoms which may have a substituent, $Ra^2$ and $Ra^3$ each independently represent an alkyl group having 1 to 10 carbon atoms which may have a substituent, and $X^-$ represents a counter anion represented by any one of formulae (d1-1) to (d1-3) shown below;

(d1-2)

(d1-3)

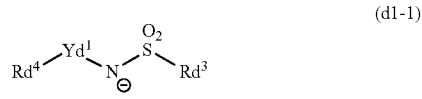

(d1-1)

wherein $Rd^1$ to $Rd^4$ represent a cyclic group which may have a substituent, a chain-like alkyl group which may have a substituent, or a chain-like alkenyl group which may have a substituent, provided that two or more of fluorine atoms are not bonded to a carbon atom adjacent to an S atom in $Rd^2$ in formula (d1-2); and $Yd^1$ represents a single bond or a divalent linking group.

4. A compound represented by general formula (d0) below:

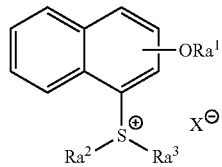
(d0)

wherein $Ra^1$ represents an alkyl group having 1 to 10 carbon atoms which may have a substituent, $Ra^2$ and $Ra^3$ each independently represent an alkyl group having 1 to 10 carbon atoms which may have a substituent, and $X^-$ represents a counter anion represented by any one of formulae (d1-1) to (d1-3) shown below:

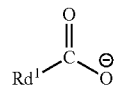
(d1-2)

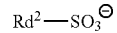
(d1-3)

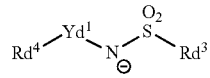
(d1-1)

wherein $Rd^1$ to $Rd^4$ represent a cyclic group which may have a substituent, a chain-like alkyl group which may have a substituent, or a chain-like alkenyl group which may have a substituent, provided that two or more of fluorine atoms are not bonded to a carbon atom adjacent to an S atom in $Rd^2$ in formula (d1-2); and $Yd^1$ represents a single bond or a divalent linking group.

* * * * *